United States Patent
Rao

(10) Patent No.: US 12,174,193 B2
(45) Date of Patent: Dec. 24, 2024

(54) AGENTS AND METHODS FOR PREDICTING RESPONSE TO THERAPY

(71) Applicant: EPIAXIS THERAPEUTICS PTY LTD, Herston (AU)

(72) Inventor: Sudha Rao, Red Hill (AU)

(73) Assignee: EPIAXIS THERAPEUTICS PTY LTD, Herston (AU)

( * ) Notice: Subject to any disclaimer, the term of this patent is extended or adjusted under 35 U.S.C. 154(b) by 1104 days.

(21) Appl. No.: 16/962,181

(22) PCT Filed: Jan. 15, 2019

(86) PCT No.: PCT/AU2019/050025
§ 371 (c)(1),
(2) Date: Jul. 14, 2020

(87) PCT Pub. No.: WO2019/136532
PCT Pub. Date: Jul. 18, 2019

(65) Prior Publication Data
US 2021/0055302 A1    Feb. 25, 2021

(30) Foreign Application Priority Data

Jan. 15, 2018  (AU) ................................ 2018900108
Feb. 8, 2018   (AU) ................................ 2018900392

(51) Int. Cl.
| | |
|---|---|
| C07K 14/705 | (2006.01) |
| A61P 35/00 | (2006.01) |
| C07K 16/28 | (2006.01) |
| G01N 33/574 | (2006.01) |

(52) U.S. Cl.
CPC ... *G01N 33/57492* (2013.01); *C07K 16/2827* (2013.01); *G01N 2333/70532* (2013.01); *G01N 2440/10* (2013.01); *G01N 2440/12* (2013.01)

(58) Field of Classification Search
None
See application file for complete search history.

(56) References Cited

U.S. PATENT DOCUMENTS

2016/0137725 A1   5/2016  Gu et al.
2020/0339691 A1*  10/2020  Rao .................. C07K 14/70532

FOREIGN PATENT DOCUMENTS

WO   WO 2016/160792 A1   10/2016
WO   WO 2019/136531 A1   7/2019

OTHER PUBLICATIONS

Aldous et al. (2018) Personalized neoantigen vaccines: A new approach to cancer immunotherapy. Bioorganic & Medicinal Chemistry 26: 2842-2849.*
Burugu et al. (2018) Emerging targets in cancer immunotherapy. Seminars in Cancer Biology 52: 39-52.*
Butterfield L.H. (2018) The Society for Immunotherapy of Cancer Biomarkers Task Force recommendations review. Seminars in Cancer Biology 52: 12-15.*
Chae et al. (2018) Molecular Biomarkers of Primary and Acquired Resistance to T-Cell-Mediated Immunotherapy in Cancer: Landscape, Clinical Implications, and Future Directions. The Oncologist 23: 410-421.*
Gao et al. (2020) Acetylation-dependent regulation of PD-L1 nuclear translocation dictates the efficacy of anti-PD-1 immunotherapy. Nature Cell Biology 22: 1064-1075.*
Huang et al. (2017) Interleukin-armed chimeric antigen receptor-modified T cells for cancer immunotherapy. Gene Therapy 25: 192-197.*
Rusch et al. (2018) Immunotherapy as an Option for Cancer Treatment. Arch. Immunol. Ther. Exp. 66: 89-96.*
Yuba E. (2018) Liposome-based immunity-inducing systems for cancer immunotherapy. Molecular Immunology 98: 8-12.*
International Preliminary Report on Patentability, mailed Jul. 30, 2020, in International Application No. PCT/AU2019/050025.
Ghebeh et al., Doxorubicin downregulates cell surface B7-H1 expression and upregulates its nuclear expression in breast cancer cells: role of B7-H1 as an anti-apoptotic molecule, Breast Cancer Research, 12:R48, 2010.
Goltz et al., Freie Vortrage: FV4—Prognostic significance and predictive value to anti-PD1 treatment of promoter methylation of PDCD1 (PD-1), CD274 (PD-L1) and PDCD1LG2 (PD-L2) for melanoma patients, Journal der Deutschen Dermatologieschen Gesellschaft, 1610-0379/2017/15 (Suppl. 3), 2017.
Extended European Search Report dated Sep. 29, 2021 in EP Application No. 20190738581.
Satelli, A., et al., Potential role of nuclear PD-LI expression in cell-surface vimentin positive circulating tumor cells as a prognostic marker in cancer patients, Scientific Reports, 6:28910, 2016.
Horita, H., et al., Identifying Regulatory Posttranslational Modifications of PD-L1: A Focus on Monoubiquitinaton, Neoplasia, vol. 19, No. 4, pp. 346-353, 2017.
Horita, H., et al., Utilizing a Comprehensive Immunoprecipitation Enrichment System to Identify an Endogenous Post-translational Modification Profile for Target Proteins, Journal of Visualized Experiments, vol. 131, No. e56912, 2018.
Huttlin, E.L., et al., The BioPlex Network: A Systematic Exploration of the Human Interactome, Cell, vol. 162, pp. 425-440, 2015.
Escors, D., et al., The intracellular signalosome of PD-L1 in cancer cells, Signal Transduction and Targeted Therapy, vol. 3, No. 26, 9 pages, 2018.
Gu, W., et al., Undo the brake of tumour immune tolerance with antibodies, peptide mimetics and small molecule compounds targeting PD-1/PD-L1 checkpoint at different locations for acceleration of cytotoxic immunity to cancer cells, Clinical and Experimental Pharmacology and Physiology, vol. 46, pp. 105-115, 2019.

(Continued)

*Primary Examiner* — Ilia I Ouspenski
(74) *Attorney, Agent, or Firm* — Knobbe, Martens, Olson & Bear, LLP

(57) ABSTRACT

Disclosed are methods and agents for predicting responses to therapy. More particularly, the present disclosure relates to methods and agents for detecting different forms of Programmed Death Ligand-1 (PD-L1) in cancer cells, which are useful for detecting location of PD-L1 in a cellular compartment (e.g., nucleus, cytoplasm, cell membrane) of a cancer cell, for predicting the likelihood of response of a cancer cell to therapy including immunotherapy, for stratifying a cancer patient as a likely responder or non-responder to a therapy, for managing treatment of a cancer patient, and for predicting clinical outcomes.

16 Claims, 19 Drawing Sheets

(56) References Cited

OTHER PUBLICATIONS

International Search Report and Written Opinion, mailed Mar. 28, 2019, in International Application No. PCT/AU2019/050025.
Phi et al., Cancer Stem Cells in Drug Resistance and their Therapeutic Implications in Cancer Treatment, Stem Cell International, vol. 2018, Article ID 5416923, 16 pages, 2018.
Sancho et al., Hallmarks of Cancer Stem Cell Metabolism, British Journal of Cancer, vol. 114, pp. 1305-1312, 2016.
Shibue et al., EMT, CSCs, and Drug Resistance: The Mechanistic Link and Clinical Implications, Nature Reviews Clinical Oncology, vol. 14, pp. 611-629, 2017.
Zheng H-C., The molecular mechanisms of Chemoresistance in Cancers, Oncotargert, vol. 8, No. 35, pp. 59950-59964, 2017.

\* cited by examiner

Potential PD-L1 signature gene targets

- Nodal *
- BMPR1B
- Smad3
- Inhibin beta A
- TGF beta 2
- CD11b
- TNF alpha
- C3
- Claudin 1
- Fibronectin
- DLL4
- Jagged1
- RANTES (CCL5)*
- Homeobox protein prospero
- FHL1
- Collagen I
- AMH
- CEACAM6

FIGURE 16

AGENTS AND METHODS FOR PREDICTING RESPONSE TO THERAPY

PRIORITY AND CROSS REFERENCE TO RELATED APPLICATIONS

This application is the U.S. National Stage Application under 35 U.S.C. § 371 of International Application No. PCT/AU2019/050025, filed Jan. 15, 2019, designating the U.S. and published in English as WO 2019/136532 A1 on Jul. 18, 2019, which claims the benefit of Australian Patent Application No. AU 2018900108, filed Jan. 15, 2018, and Australian Patent Application No. AU 2018900392, filed Feb. 8, 2018. Any and all applications for which a foreign or a domestic priority is claimed is/are identified in the Application Data Sheet filed herewith and is/are hereby incorporated by reference in their entirety under 37 C.F.R. § 1.57.

FIELD OF THE INVENTION

This application claims priority to Australian Provisional Application No. 2018900108 entitled "Proteinaceous molecules and uses therefor" filed 15 Jan. 2018, and to Australian Provisional Application No. 2018900392 entitled "Agents and methods for predicting response to therapy" filed 8 Feb. 2018, the contents of each of which are incorporated herein by reference in their entirety.

This invention relates generally to methods and agents for predicting responses to therapy. More particularly, the present invention relates to methods and agents for detecting different forms of Programmed Death Ligand-1 (PD-L1) in cancer cells, which are useful for detecting location of PD-L1 in a cellular compartment (e.g., nucleus, cytoplasm, cell membrane) of a cancer cell, for predicting the likelihood of response of a cancer cell to therapy including immunotherapy, for stratifying a cancer patient as a likely responder or non-responder to a therapy, for managing treatment of a cancer patient, and for predicting clinical outcomes.

BACKGROUND OF THE INVENTION

Cancer is a significant cause of morbidity and mortality worldwide. While the standards of care for many different cancer types have greatly improved over the years, current standards of care still fail to meet the need for effective therapies to improve treatment of cancer. The clinical use of immuno-oncology agents targeting cytotoxic T-lymphocyte-associated protein 4 (CTLA-4) and the programmed cell death receptor-1 (PD-1) and its ligand PD-L1, have resulted in improvements in the standard of care for treating many cancer types. While these checkpoint inhibitors have produced improved clinical responses in certain cancers, durable clinical responses only occur in approximately 10-45% of patients. Moreover, a significant number of tumors are either resistant or become refractory. For example, about 20-50% of melanoma and lung cancers will respond significantly to immunotherapies, while others will not. Thus, identifying which subjects are better candidates for immunotherapy is highly advantageous from a health care and patient quality of life perspective.

PD-L1 is a cell surface glycoprotein that is one of two known ligands for PD-1. Expression of PD-L1 has been observed on the surface of a variety of immune cells, and PD-L1 mRNA is expressed by non-lymphoid tissues including vascular endothelial cells, epithelial cells, muscle cells, and in tonsil and placental tissue. PD-L1 expression has also been observed in a variety of human cancers, and interaction of tumor-cell expressed PD-L1 with PD-1 can induce inhibition or apoptosis of tumor-specific T cells. In several cancers including for example ovarian, renal, colorectal, pancreatic and liver cancers as well as melanoma, it has been shown that PD-L1 expression correlated with poor prognosis and reduced overall survival irrespective of subsequent treatment. Anti-PD-1 monoclonal antibodies (mAbs) that block binding of PD-L1 to PD-1 have been shown to have anti-tumor activity against a variety of tumor types, with early human clinical data suggesting that patients whose tumors express PD-L1 are more likely to respond to anti-PD-1 therapy, as disclosed for example in International Patent Application Publication No. WO 2014/165422.

Although immunostaining for PD-L1 on tumor cells has been reported to be associated with response in clinical trials, the overall accuracy of PD-L1 staining is only about 62% in a clinical study (Topalian et al., 2012, *N Engl. J Med* 366(26):2443-2454), with imperfect negative and positive predictive value (Weber et al., 2013. *J Clin Oncol* 31(34): 4311-4318).

Accordingly, there remains a need in the art for methods and agents that aid in predicting response to therapy including immunotherapy, with improved accuracy.

SUMMARY OF THE INVENTION

The present invention arises in part from the determination that different post-translational modifications of PD-L1 in a cancer cell result in localization of this glycoprotein to different cellular compartments, which can significantly affect the sensitivity or resistance of the cancer cell to therapy, including cytotoxic therapy and immunotherapy. In particular, the present inventors have found that different post-translational modifications of a lysine (i.e., PD-L1-263K) in the nuclear localization sequence (NLS) of PD-L1 control whether PD-L1 is localized to the nucleus or to the cytoplasm/cell membrane. Notably, it was found that methylation of PD-L1-263K (i.e., PD-L1-263KMe) substantially localizes PD-L1 to the cytoplasm and/or cell membrane of the cancer cell, which correlates with sensitivity of the cancer cell to therapy. However, it was also found that acetylation of PD-L1-263K (i.e., PD-L1-263KAc) largely localizes PD-L1 to the nucleus, which associates with epithelial-to-mesenchymal transition (EMT) and/or stemness of the cancer cell and correlates with resistance to therapy. Indeed, it has been determined that expression of nuclear PD-L1 leads to significant upregulation of biomarkers of chemo-resistance, stemness and/or disease progression, including C—C motif chemokine ligand 5 (CCL5, also known as RANTES) and NODAL. Additionally, the present inventors have found that these PD-L1-263KAc and PD-L1-263KMe biomarkers (which are also referred to herein as "response to therapy" biomarkers) can optionally be used in combination with one or more mesenchymal and/or stemness biomarkers, which suitably associate with drug resistance and/or disease burden, such as prominin-1 (CD133), aldehyde dehydrogenase 1 family, member A1 (ALDH1A), E1A-binding protein 300 kDa (P300), DNA (cytosine-5)-methyltransferase 1 (DNMT1), SET Domain Bifurcated 1 (SETDB1) and ATP-binding cassette sub-family B member 5 (ABCB5), for monitoring response to therapy and for predicting treatment outcomes and clinical outcomes. These findings have been reduced to practice in methods and agents for determining location of PD-L1 in a cellular compartment of a cancer cell, for detecting different forms of PD-L1 in predicting and/or monitoring response to therapy, for stratifying patients according to the form of PD-L1 expressed in the cancer cell, for managing the treatment of patients according to the stratification, and for predicting clinical outcomes, as described hereafter.

Accordingly, in one aspect, the present invention provides methods for determining location of PD-L1 in a cellular compartment of a cancer cell. These methods generally comprise, consist or consist essentially of detecting in the cancer cell a post-translational modification in the nuclear localization sequence of PD-L1, thereby determining the cellular compartment of the cancer cell in which PD-L1 is located. In some embodiments, the methods comprise detecting acetylation of PD-L1-K263 (also referred to herein as "PD-L1-K263Ac") in the cancer cell, to thereby determine that the cellular compartment is the nucleus. In representative examples of this type, the methods comprise detecting an elevated level of PD-L1-K263Ac in the cancer cell relative to a suitable control (e.g., a normal cell or an epithelial cancer cell), which indicates that the cellular compartment is the nucleus. In some embodiments, the methods comprise detecting methylation of PD-L1-K263 (also referred to herein as "PD-L1-K263Me") in the cancer cell, to thereby determine that the cellular compartment is the cytoplasm and/or cell membrane. In illustrative examples of this type, the methods comprise detecting an elevated level of PD-L1-K263Me in the cancer cell relative to a suitable control (e.g., a mesenchymal cancer cell), which indicates that the cellular compartment is the cytoplasm and/or cell membrane.

Another aspect of the present invention provides methods for predicting the likelihood of response of a cancer cell to a therapy (e.g., cytotoxic therapy and/or immunotherapy). These methods generally comprise, consist or consist essentially of detecting in the cancer cell a post-translational modification in the nuclear localization sequence of PD-L1, thereby predicting the likelihood of response of the cancer cell to the therapy. In some embodiments, the methods comprise detecting acetylation of PD-L1-K263 (also referred to herein as "PD-L1-K263Ac") in the cancer cell to thereby determine that the cancer cell has increased likelihood of resistance to the therapy. In some embodiments, the methods comprise detecting methylation of PD-L1-K263 (also referred to herein as "PD-L1-K263Me") in the cancer cell to thereby determine that the cancer cell has increased likelihood of sensitivity to the therapy.

In related aspects, the present invention provides methods for determining likelihood of resistance of a cancer cell to a therapy (e.g., cytotoxic therapy and/or immunotherapy). These methods generally comprise, consist or consist essentially of detecting the presence of PD-L1-K263Ac in the cancer cell, to thereby determine that the cancer cell has increased likelihood of resistance to the therapy. In representative examples of this type, the methods comprise detecting an elevated level of PD-L1-K263Ac in the cancer cell relative to a suitable control (e.g., a normal cell or an epithelial cancer cell), which indicates that the cancer cell has increased likelihood of resistance to the therapy.

In some of the same and other embodiments, the methods comprise contacting a sample comprising the cancer cell with an antigen-binding molecule that binds specifically to PD-L1-K263Ac, and detecting in the sample a complex that comprises the antigen-binding molecule and PD-L1-K263Ac, to thereby determine that the cancer cell has increased likelihood of resistance to the therapy.

In other related aspects, the present invention provides methods for determining likelihood of sensitivity of a cancer cell to a therapy (e.g., cytotoxic therapy and/or immunotherapy). These methods generally comprise, consist or consist essentially of detecting the presence of PD-L1-K263Me in the cancer cell, to thereby determine that the cancer cell has increased likelihood of sensitivity to the therapy. In illustrative examples of this type, the methods comprise detecting an elevated level of PD-L1-K263Me in the cancer cell relative to a suitable control (e.g., a mesenchymal cancer cell), which indicates that the cancer cell has increased likelihood of sensitivity to the therapy.

In some of the same and other embodiments, the methods comprise contacting a sample comprising the cancer cell with an antigen-binding molecule that binds specifically to PD-L1-K263Me, and detecting in the sample a complex that comprises the antigen-binding molecule and the PD-L1-K263Me, to thereby determine that the cancer cell has increased likelihood of sensitivity to the therapy.

In still other related aspects, the present invention provides methods for predicting a likelihood of response of a cancer cell to a therapy (e.g., cytotoxic therapy and/or immunotherapy). These methods generally comprise, consist or consist essentially of: measuring the level of PD-L1-K263Ac in the cancer cell, measuring the level of PD-L1-K263Me in the cancer cell; comparing the level of PD-L1-K263Ac and PD-L1-K263Me in the cancer cell; and predicting the response of the cancer cell to the therapy based on the comparison, wherein a higher level of PD-L1-K263Ac than PD-L1-K263Me in the cancer cell indicates that the cancer cell has an increased likelihood of resistance to the therapy and wherein a higher level of PD-L1-K263Me than PD-L1-K263Ac in the cancer cell indicates that the cancer cell has an increased likelihood of sensitivity to the therapy.

In some embodiments, the methods comprise: contacting a sample comprising the cancer cell with a first antigen-binding molecule that binds specifically to PD-L1-K263Ac and a second antigen-binding molecule that binds specifically to PD-L1-K263Me; measuring in the sample the level of a first complex that comprises the first antigen-binding molecule and the PD-L1-K263Ac, and the level of a second complex that comprises the second antigen-binding molecule and the PD-L1-K263Me; and predicting the likelihood of response of the cancer cell to the therapy based on the comparison, wherein a higher level of the first complex than the second complex in the sample indicates that the cancer cell has an increased likelihood of resistance to the therapy and wherein a higher level of the second complex in the sample indicates that the cancer cell has an increased likelihood of sensitivity to the therapy.

In some embodiments of the methods for predicting the likelihood of response (e.g., sensitivity or resistance) of a cancer cell to a therapy (e.g., cytotoxic therapy and/or immunotherapy), the methods are suitably used for monitoring response to therapy. In non-limiting examples of this type, the methods comprise detecting in the cancer cell PD-L1-K263Ac and at least one mesenchymal and/or stemness biomarker, which suitably associates with drug resistance and/or disease burden (e.g., CD133, ALDH1A, P300, DNMT1, SETDB1 and ABCB5), to thereby monitor response to therapy and/or disease burden. Non-limiting examples of the at least one mesenchymal and/or sternness biomarker include: (a) CD133; (b) CD133:ALDH1A; (c) CD133:ALDH1A:P300; (d) CD133:ALDH1A:P300:DNMT1; (e) CD133:ALDH1A:P300:DNMT1:SETDB1; (f) CD133:ALDH1A:P300:DNMT1:SETDB1:ABCB5; (g) ALDH1A; (h) ALDH1A:P300; (i) ALDH1A:P300:DNMT1; (j) ALDH1A:P300:DNMT1:SETDB1; (k) ALDH1A:P300:DNMT1:SETDB1:ABCB5; (l) P300; (m) P300:DNMT1; (n) P300:DNMT1:SETDB1; (o) P300:

DNMT1:SETDB1:ABC135; (p) DNMT1; (q) DNMT1: SETDB1; (r) DNMT1:SETDB1:ABC35; (s) SETDB1; (t) SETDB1:ABCB5; and (u) ABCB5.

In some embodiments, the methods comprise detecting an unchanged level of PD-L1-K263Ac and optionally an unchanged level of the at least one mesenchymal and/or sternness biomarker in the cancer cell relative to a suitable control (e.g., a cancer cell not exposed to the therapy), which indicates that the cancer cell is likely not responding to the therapy. In some embodiments, the methods comprise detecting an elevated level of PD-L1-K263Ac and optionally an elevated level of the at least one mesenchymal and/or sternness biomarker in the cancer cell relative to a suitable control (e.g., a cancer cell not exposed to the therapy), which indicates that the cancer cell is likely not responding to the therapy. In other embodiments, the methods comprise detecting a decreased level of PD-L1-K263Ac and optionally a decreased level of the at least one mesenchymal and/or sternness biomarker in the cancer cell relative to a suitable control (e.g., a cancer cell not exposed to the therapy), which indicates that the cancer cell is likely responding to the therapy.

In some embodiments of the methods for predicting the likelihood of response (e.g., sensitivity or resistance) of a cancer cell to a therapy (e.g., cytotoxic therapy and/or immunotherapy), the methods are suitably used for monitoring response to therapy. In non-limiting examples of this type, the methods comprise detecting in the cancer cell PD-L1-K263Me and at least one mesenchymal and/or sternness biomarker, which suitably associates with drug resistance and/or disease burden (e.g., CD133, ALDH1A, P300, DNMT1, SETDB1 and ABCB5), to thereby monitor response to therapy and/or disease burden. Non-limiting examples of the at least one mesenchymal and/or stemness biomarker include: (a) CD133; (b) CD133:ALDH1A; (c) CD133:ALDH1A:P300; (d) CD133:ALDH1A:P300: DNMT1; (e) CD133:ALDH1A:P300:DNMT1:SETDB1; (f) CD133:ALDH1A:P300:DNMT1:SETDB1:ABCB5; (g) ALDH1A; (h) ALDH1A:P300; (i) ALDH1A:P300: DNMT1; (j) ALDH1A:P300:DNMT1:SETDB1; (k) ALDH1A:P300:DNMT1:SETDB1:ABC135; (l) P300; (m) P300:DNMT1; (n) P300:DNMT1:SETDB1; (o) P300: DNMT1:SETDB1:ABCB5; (p) DNMT1; (q) DNMT1: SETDB1; (r) DNMT1:SETDB1:ABCB5; (s) SETDB1; (t) SETDB1:ABCB5; and (u) ABCB5.

In some embodiments, the methods comprise detecting an unchanged level of PD-L1-K263Me and optionally an unchanged level of the at least one mesenchymal and/or sternness biomarker in the cancer cell relative to a suitable control (e.g., a cancer cell not exposed to the therapy), which indicates that the cancer cell is likely not responding to the therapy. In some embodiments, the methods comprise detecting an elevated level of PD-L1-K263Me and optionally a decreased level of the at least one mesenchymal and/or sternness biomarker in the cancer cell relative to a suitable control (e.g., a cancer cell not exposed to the therapy), which indicates that the cancer cell is likely responding to the therapy. In other embodiments, the methods comprise detecting a decreased level of PD-L1-K263Me and optionally an increased level of the at least one mesenchymal and/or sternness biomarker in the cancer cell relative to a suitable control (e.g., a cancer cell not exposed to the therapy), which indicates that the cancer cell is likely responding to the therapy.

In yet another aspect, the present invention provides methods for stratifying a cancer patient as a likely responder or non-responder to a therapy (e.g., cytotoxic therapy and/or immunotherapy). These methods generally comprise, consist or consist essentially of detecting in a sample taken from a patient a cancer cell that comprises a post-translational modification in the nuclear localization sequence of PD-L1, to thereby stratify the patient as a likely responder or non-responder to the therapy. In some embodiments, the methods comprise detecting PD-L1-K263Ac in the cancer cell and stratifying the patient as a likely non-responder to the therapy. In illustrative examples of this type, the methods comprise contacting the sample with an antigen-binding molecule that binds specifically to PD-L1-K263Ac, and detecting in the sample a complex that comprises the antigen-binding molecule and the PD-L1-K263Ac, to thereby stratify the patient as a likely non-responder to the therapy. In some embodiments, the methods comprise detecting PD-L1-K263Me in the cancer cell and stratifying the patient as a likely responder to the therapy. In non-limiting examples of this type, the methods comprise contacting the sample with an antigen-binding molecule that binds specifically to PD-L1-K263Me, and detecting in the sample a complex that comprises the antigen-binding molecule and the PD-L1-K263Me, to thereby stratify the patient as a likely responder to the therapy. In still other embodiments, the methods comprise: contacting the sample with a first antigen-binding molecule that binds specifically to PD-L1-K263Ac and a second antigen-binding molecule that binds specifically to PD-L1-K263Me; measuring in the sample the level of a first complex that comprises the first antigen-binding molecule and PD-L1-K263Ac, and the level of a second complex that comprises the second antigen-binding molecule and PD-L1-K263Me; and stratifying the patient as a likely responder or non-responder based on the comparison, wherein the patient is stratified as a likely non-responder if the level of the first complex is higher than the second complex in the sample and wherein the patient is stratified as a likely responder if the level of the second complex is higher than the first complex.

The prediction and stratification methods broadly described above and elsewhere herein provide a clinician or physician with information about the likelihood of response to treatment with a cancer therapy. On the basis of the results of these methods, the clinician or physician can: (i) treat a subject with a therapy (e.g., cytotoxic therapy and/or immunotherapy) on the basis that the subject is likely to respond to the therapy; (ii) avoid treating a subject with a therapy (e.g., cytotoxic therapy and/or immunotherapy) on the basis that the subject is unlikely to respond to the therapy; (iii) enroll the subject in clinical trials for a new therapy; (iv) treat a subject that is unlikely to respond to a therapy (e.g., cytotoxic therapy and/or immunotherapy) with an alternative therapy, such as a therapy that stimulates mesenchymal-to-epithelial transition of a cancer cell; and/or (v) discuss the likely treatment and outcome scenarios with the subject. Accordingly, a further aspect of the present invention provides methods for managing treatment of a cancer patient with a therapy (e.g., cytotoxic therapy and/or immunotherapy). These methods generally comprise, consist or consist essentially of: selecting a cancer patient for treating with the therapy on the basis that the patient is a likely responder to the therapy, or selecting a cancer patient for not treating with the therapy on the basis that the patient is a likely non-responder to the therapy and treating or not treating the patient with the therapy based on the selection, wherein the selection is based on a stratification method that comprises detecting in a sample taken from the patient a cancer cell that comprises a post-translational modification in the nuclear localization sequence of PD-L1, to thereby stratify the patient as a likely responder or non-responder to the therapy. In some embodiments, the stratification method comprises detecting PD-L1-K263Me in the cancer cell and stratifying the patient as a likely responder to the therapy. In non-limiting examples of this type, the method comprises contacting the sample with an antigen-binding molecule that binds specifically to PD-L1-K263Me, and detecting in the sample a complex that comprises the antigen-binding molecule and the PD-L1-K263Me, to thereby stratify the patient as a likely responder to the therapy. In some embodiments, the stratification method comprises detecting PD-L1-K263Ac in the cancer cell and stratifying the patient as a likely non-responder to the therapy. In illustrative examples of this type, the method comprises contacting the sample with an antigen-binding molecule that binds specifically to PD-L1-K263Ac, and detecting in the sample a complex that comprises the antigen-binding molecule and the PD-L1-K263Ac, to thereby stratify the patient as a likely non-responder to the therapy. In still other embodiments, the method comprises: contacting the sample with a first antigen-binding molecule that binds specifically to PD-L1-K263Ac and a second antigen-binding molecule that binds specifically to PD-L1-K263Me; measuring in the sample the level of a first complex that comprises the first antigen-binding molecule and PD-L1-K263Ac, and the level of a second complex that comprises the second antigen-binding molecule and PD-L1-K263Me; and stratifying the patient as a likely responder or non-responder based on the comparison, wherein the patient is stratified as a likely non-responder if the level of the first complex is higher than the second complex in the sample and wherein the patient is stratified as a likely responder if the level of the second complex is higher than the first complex.

In some embodiments of the methods for stratifying a cancer patient as a likely responder or non-responder to a therapy (e.g., cytotoxic therapy and/or immunotherapy) and for managing treatment of a cancer patient with a therapy (e.g., cytotoxic therapy and/or immunotherapy), the methods further comprise detecting in the cancer cell PD-L1-K263Ac and at least one mesenchymal and/or sternness biomarker, which suitably associates with drug resistance and/or disease burden (e.g., CD133, ALDH1A, P300, DNMT1, SETDB1 and ABCB5), to thereby monitor the patient's response to the therapy and/or disease burden. Non-limiting examples of the at least one mesenchymal and/or sternness biomarker include: (a) CD133; (b) CD133: ALDH1A; (c) CD133:ALDH1A:P300; (d) CD133: ALDH1A:P300:DNMT1; (e) CD133:ALDH1A:P300: DNMT1:SETDB1; (f) CD133:ALDH1A:P300:DNMT1: SETDB1:ABC135; (g) ALDH1A; (h) ALDH1A:P300; (i) ALDH1A:P300:DNMT1; (j) ALDH1A:P300:DNMT1: SETDB1; (k) ALDH1A:P300:DNMT1:SETDB1:ABCB5; (l) P300; (m) P300:DNMT1; (n) P300:DNMT1:SETDB1; (o) P300:DNMT1:SETDB1:ABCB5; (p) DNMT1; (q) DNMT1:SETDB1; (r) DNMT1:SETDB1:ABCB5; (s) SETDB1; (t) SETDB1:ABCB5; and (u) ABCB5.

In some embodiments, these methods comprise detecting an unchanged level of PD-L1-K263Ac and optionally an unchanged level of the at least one mesenchymal and/or sternness biomarker in the cancer cell relative to a suitable control (e.g., a cancer cell of the patient, which expresses PD-L1-K263Ac, before exposure to the therapy), which indicates that the patient is likely not responding to the therapy and/or that the patient's disease burden is likely unchanged. In other embodiments, these methods comprise detecting an elevated level of PD-L1-K263Ac and optionally an elevated level of the at least one mesenchymal and/or sternness biomarker in the cancer cell relative to a suitable control (e.g., a cancer cell of the patient before exposure to the therapy), which indicates that the patient is likely not responding to the therapy and/or that the patient's disease burden has likely increased. In other embodiments, the methods comprise detecting a decreased level of PD-L1-K263Ac and optionally a decreased level of the at least one mesenchymal and/or sternness biomarker in the cancer cell relative to a suitable control (e.g., a cancer cell of the patient before exposure to the therapy), which indicates that the patient is likely responding to the therapy and/or that the patient's disease burden has likely decreased.

In some embodiments of the methods for stratifying a cancer patient as a likely responder or non-responder to a therapy (e.g., cytotoxic therapy and/or immunotherapy) and for managing treatment of a cancer patient with a therapy (e.g., cytotoxic therapy and/or immunotherapy), the methods further comprise detecting in the cancer cell PD-L1-K263Me and at least one mesenchymal and/or sternness biomarker, which suitably associates with drug resistance and/or disease burden (e.g., CD133, ALDH1A, P300, DNMT1, SETDB1 and ABCB5), to thereby monitor the patient's response to the therapy and/or disease burden. Non-limiting examples of the at least one mesenchymal and/or sternness biomarker include: (a) CD133; (b) CD133: ALDH1A; (c) CD133:ALDH1A: P300; (d) CD133: ALDH1A: P300: DNMT1; (e) CD133:ALDH1A: P300: DNMT1:SETDB1; (f) CD133:ALDH1A: P300:DNMT1: SETDB1:ABCB5; (g) ALDH1A; (h) ALDH1A:P300; (i) ALDH1A:P300:DNMT1; (j) ALDH1A:P300:DNMT1: SETDB1; (k) ALDH1A:P300:DNMT1:SETDB1:ABCB5; (l) P300; (m) P300:DNMT1; (n) P300:DNMT1:SETDB1; (o) P300:DNMT1:SETDB1:ABCB5; (p) DNMT1; (q) DNMT1:SETDB1; (r) DNMT1:SETDB1:ABCB5; (s) SETDB1; (t) SETDB1:ABC135; and (u) ABC55.

In some embodiments, these methods comprise detecting an elevated level of PD-L1-K263Me and optionally a decreased level of the at least one mesenchymal and/or sternness biomarker in the cancer cell relative to a suitable control (e.g., a cancer cell of the patient before exposure to the therapy), which indicates that the patient is likely responding to the therapy and/or that the patient's disease burden has likely decreased. In other embodiments, the methods comprise detecting a decreased level of PD-L1-K263Me and optionally an increased level of the at least one mesenchymal and/or sternness biomarker in the cancer cell relative to a suitable control (e.g., a cancer cell of the patient before exposure to the therapy), which indicates that the patient is likely not responding to the therapy and/or that the patient's disease burden has likely increased.

Still a further aspect of the present invention provides methods for predicting treatment outcome for a cancer patient treated with a therapy (e.g., cytotoxic therapy and/or immunotherapy). These methods generally comprise, consist or consist essentially of detecting in a sample taken from the patient a cancer cell that comprises a post-translational modification in the nuclear localization sequence of PD-L1, to thereby predict the treatment outcome for the patient. In some embodiments, the methods comprise detecting PD-L1-K263Ac in the cancer cell and predicting a negative treatment outcome. In illustrative examples of this type, the negative treatment outcome is progressive disease. In some of the same and other embodiments, the methods comprise contacting the sample with an antigen-binding molecule that binds specifically to PD-L1-K263Ac, and detecting in the sample a complex that comprises the antigen-binding molecule and the PD-L1-K263Ac, to thereby predict a negative treatment outcome for the patient. In some embodiments, the methods comprise detecting PD-L1-K263Me in the cancer cell and predicting a positive treatment outcome. In illustrative examples of this type, the positive treatment outcome is selected from a partial or complete response to the therapy and stable disease. In some of the same and other embodiments, the methods comprise contacting the sample with an antigen-binding molecule that binds specifically to PD-L1-K263Me, and detecting in the sample a complex that comprises the antigen-binding molecule and the PD-L1-K263Me, to thereby predict a positive treatment outcome for the patient. In still other embodiments, the methods comprise: contacting the sample with a first antigen-binding molecule that binds specifically to PD-L1-K263Ac and a second antigen-binding molecule that binds specifically to PD-L1-K263Me; measuring in the sample the level of a first complex that comprises the first antigen-binding molecule and PD-L1-K263Ac, and the level of a second complex that comprises the second antigen-binding molecule and PD-L1-K263Me; and predicting the treatment outcome for the patient based on the comparison, wherein the treatment outcome is predicted as a negative treatment outcome if the level of the first complex is higher than the second complex in the sample and wherein the treatment outcome is predicted as a positive treatment outcome if the level of the second complex is higher than the first complex.

In some embodiments of the methods for predicting treatment outcome for a cancer patient treated with a therapy (e.g., cytotoxic therapy and/or immunotherapy), the methods further comprise detecting in the cancer cell PD-L1-K263Ac and at least one mesenchymal and/or sternness biomarker, which suitably associates with drug resistance and/or disease burden (e.g., CD133, ALDH1A, P300, DNMT1, SETDB1 and ABCB5), to thereby predict the treatment outcome for the patient. Non-limiting examples of the at least one mesenchymal and/or sternness biomarker include: (a) CD133; (b) CD133:ALDH1A; (c) CD133:ALDH1A:P300; (d) CD133:ALDH1A:P300:DNMT1; (e) CD133:ALDH1A:P300:DNMT1:SETDB1; (f) CD133:ALDH1A:P300:DNMT1:SETDB1:ABCB5; (g) ALDH1A; (h) ALDH1A:P300; (i) ALDH1A:P300:DNMT1; (j) ALDH1A:P300:DNMT1:SETDB1; (k) ALDH1A:P300:DNMT1:SETDB1:ABCB5; (l) P300; (m) P300:DNMT1; (n) P300:DNMT1:SETDB1; (o) P300:DNMT1:SETDB1:ABCB5; (p) DNMT1; (q) DNMT1:SETDB1; (r) DNMT1:SETDB1:ABCB5; (s) SETDB1; (t) SETDB1:ABC135; and (u) ABCB5.

In some embodiments, these methods comprise detecting an unchanged level of PD-L1-K263Ac and optionally an unchanged or elevated level of the at least one mesenchymal and/or sternness biomarker in the cancer cell relative to a suitable control (e.g., a cancer cell of the patient, expresses PD-L1-K263Ac, before exposure to the therapy), which is indicative of a negative treatment outcome for the patient. In other embodiments, the methods comprise detecting a decreased level of PD-L1-K263Ac and optionally a decreased level of the at least one mesenchymal and/or sternness biomarker in the cancer cell relative to a suitable control (e.g., a cancer cell of the patient before exposure to the therapy), which is indicative of a positive treatment outcome for the patient.

In some embodiments of the methods for stratifying a cancer patient as a likely responder or non-responder to a therapy (e.g., cytotoxic therapy and/or immunotherapy) and for managing treatment of a cancer patient with a therapy (e.g., cytotoxic therapy and/or immunotherapy), the methods further comprise detecting in the cancer cell PD-L1-K263Me and at least one mesenchymal and/or sternness biomarker, which suitably associates with drug resistance and/or disease burden (e.g., CD133, ALDH1A, P300, DNMT1, SETDB1 and ABCB5), to thereby monitor the patient's response to the therapy and/or disease burden. Non-limiting examples of the at least one mesenchymal and/or sternness biomarker include: (a) CD133; (b) CD133:ALDH1A; (c) CD133:ALDH1A:P300; (d) CD133:ALDH1A:P300:DNMT1; (e) CD133:ALDH1A:P300:DNMT1:SETDB1; (f) CD133:ALDH1A:P300:DNMT1:SETDB1:ABCB5; (g) ALDH1A; (h) ALDH1A:P300; (i) ALDH1A:P300:DNMT1; (j) ALDH1A:P300:DNMT1:SETDB1; (k) ALDH1A:P300:DNMT1:SETDB1:ABCB5; (l) P300; (m) P300:DNMT1; (n) P300:DNMT1:SETDB1; (o) P300:DNMT1:SETDB1:ABCB5; (p) DNMT1; (q) DNMT1:SETDB1; (r) DNMT1:SETDB1:ABCB5; (s) SETDB1; (t) SETDB1:ABCB5; and (u) ABCB5.

In some embodiments, these methods comprise detecting an elevated level of PD-L1-K263Me and optionally a decreased level of the at least one mesenchymal and/or sternness biomarker in the cancer cell relative to a suitable control (e.g., a cancer cell of the patient before exposure to the therapy), which is indicative of a positive treatment outcome for the patient. In other embodiments, the methods comprise detecting a decreased level of PD-L1-K263Me and optionally an increased level of the at least one mesenchymal and/or sternness biomarker in the cancer cell relative to a suitable control (e.g., a cancer cell of the patient before exposure to the therapy), which is indicative of a negative treatment outcome for the patient.

In some embodiments of the methods for predicting treatment outcome, the methods further comprise predicting a clinical outcome for the cancer patient based on the predicted treatment outcome. Non-limiting examples of clinical outcomes include tumor response (TR), overall survival (OS), progression free survival (PFS), disease free survival, time to tumor recurrence (TTR), time to tumor progression (TTP), relative risk (RR), toxicity or side effect.

Another aspect of the present invention provides methods for treating a cancer patient. These methods generally comprise, consist or consist essentially of administering an effective amount of a therapeutic agent (e.g., a cytotoxic agent or an immunotherapeutic agent) to the cancer patient on the basis that the cancer patient is stratified as a likely responder to the therapeutic agent, wherein the stratification is carried out by a stratification method broadly described above and elsewhere herein.

In another aspect, the present invention provides an antigen-binding molecule that binds specifically to PD-L1-K263Ac, suitably for detecting location of PD-L1 in a cellular compartment (e.g., nucleus) of a cancer cell, for predicting the likelihood of response of a cancer cell to a therapy (e.g., cytotoxic therapy and/or immunotherapy), for determining likelihood of resistance of a cancer cell to a therapy (e.g., cytotoxic therapy and/or immunotherapy), for determining likelihood of sensitivity of a cancer cell to a therapy (e.g., cytotoxic therapy and/or immunotherapy), for stratifying a cancer patient as a likely responder or non-responder to a therapy (e.g., cytotoxic therapy and/or immunotherapy), and/or for managing treatment of a cancer patient with a therapy (e.g., cytotoxic therapy and/or immunotherapy).

In related aspects, the present invention provides a complex comprising PD-L1-K263Ac and an antigen-binding molecule that binds specifically to the PD-L1-K263Ac.

In still another aspect, the present invention provides an antigen-binding molecule that binds specifically to PD-L1-

K263Me, suitably for detecting location of PD-L1 in a cellular compartment (e.g., cytoplasm and/or cell membrane) of a cancer cell, for predicting the likelihood of response of a cancer cell to a therapy (e.g., cytotoxic therapy and/or immunotherapy), for determining likelihood of resistance of a cancer cell to a therapy (e.g., cytotoxic therapy and/or immunotherapy), for determining likelihood of sensitivity of a cancer cell to a therapy (e.g., cytotoxic therapy and/or immunotherapy), for stratifying a cancer patient as a likely responder or non-responder to a therapy (e.g., cytotoxic therapy and/or immunotherapy), and/or for managing treatment of a cancer patient with a therapy (e.g., cytotoxic therapy and/or immunotherapy).

In related aspects, the present invention provides a complex comprising PD-L1-K263Me and an antigen-binding molecule that binds specifically to the PD-L1-K263Me.

In related aspects, the present invention provides kits for detecting location of PD-L1 in a cellular compartment (e.g., nucleus, cytoplasm and/or cell membrane) of a cancer cell, for predicting the likelihood of response of a cancer cell to a therapy (e.g., cytotoxic therapy and/or immunotherapy), for determining likelihood of resistance of a cancer cell to a therapy (e.g., cytotoxic therapy and/or immunotherapy), for determining likelihood of sensitivity of a cancer cell to a therapy (e.g., cytotoxic therapy and/or immunotherapy), for stratifying a cancer patient as a likely responder or non-responder to a therapy (e.g., cytotoxic therapy and/or immunotherapy), and/or for managing treatment of a cancer patient with a therapy (e.g., cytotoxic therapy and/or immunotherapy), which kits include an antigen-binding molecule that binds specifically to PD-L1-K263Ac and/or an antigen-binding molecule that binds specifically to PD-L1-K263Me. Optionally, the kits may comprise one or more controls including positive and negative controls. In illustrative examples of this type, a positive control may be selected from a PD-L1-K263Ac polypeptide or a PD-L1-K263Me polypeptide. In some embodiments, the kits contain instructional material for performing one or more of the methods broadly described above and elsewhere herein.

In specific embodiments of any of the aspects disclosed above and elsewhere herein, the antigen-binding molecule (e.g., the anti-PD-L1-K263Ac antigen-binding molecule and/or the anti-PD-L1-K263Me antigen-binding molecule) is associated directly or indirectly with a detectable label or reporter molecule.

The present invention also discloses that PD-L1 binds to the lysine acetyltransferase, P300, and to the methyltransferases DNMT1 and SETDB1, which are biomarkers of chemo-resistance, stemness and/or disease progression, to form complexes that stimulate or are otherwise associated with development of EMT and/or stemness of the cancer cell as well as resistance to therapy. The inventors propose that complexes of PD-L1 and these binding partners can also be used in the methods described above and elsewhere herein. Accordingly, a further aspect of the present invention provides methods for determining location of PD-L1 in a cellular compartment of a cancer cell, predicting the likelihood of response of a cancer cell to a therapy (e.g., cytotoxic therapy and/or immunotherapy), stratifying a cancer patient as a likely responder or non-responder to a therapy (e.g., cytotoxic therapy and/or immunotherapy), managing treatment of a cancer patient with a therapy (e.g., cytotoxic therapy and/or immunotherapy), and/or predicting treatment outcome for a cancer patient treated with a therapy (e.g., cytotoxic therapy and/or immunotherapy). These methods generally comprise, consist or consist essentially of: (i) obtaining a sample from a cancer patient, wherein the sample comprises a cancer cell; (ii) contacting the sample with a first antigen-binding molecule that binds specifically to PD-L1 in the sample and a second antigen-binding molecule that binds specifically to a PD-L1-binding partner selected from P300, DNMT1 and SETDB1 in the sample; and (iii) detecting the first and second binding antigen-binding molecules when bound to a complex comprising PD-L1 and the PD-L1-binding partner in the sample, wherein an elevated level of the complex detected in the sample relative to a level of the complex detected in a control sample (e.g., one comprising a normal cell or an epithelial cancer cell) indicates that the cellular compartment of PD-L1 is the nucleus, that the cancer cell has increased likelihood of resistance to the therapy, that the cancer patient is a likely non-responder to the therapy, that the cancer patient is selected for not treating with the therapy, and/or that the treatment outcome for the patient is predicted to be a likely negative treatment outcome.

In yet another aspect, the present invention provides methods for determining location of PD-L1 in a cellular compartment of a cancer cell, predicting the likelihood of response of a cancer cell to a therapy (e.g., cytotoxic therapy and/or immunotherapy), stratifying a cancer patient as a likely responder or non-responder to a therapy (e.g., cytotoxic therapy and/or immunotherapy), managing treatment of a cancer patient with a therapy (e.g., cytotoxic therapy and/or immunotherapy), and/or predicting treatment outcome for a cancer patient treated with a therapy (e.g., cytotoxic therapy and/or immunotherapy). These methods generally comprise, consist or consist essentially of: (i) obtaining a sample from a cancer patient, wherein the sample comprises a cancer cell; (ii) contacting the sample with a first antigen-binding molecule that binds specifically to PD-L1 in the sample and a second antigen-binding molecule that binds specifically to a PD-L1-binding partner selected from P300, DNMT1 and SETDB1 in the sample; and (iii) detecting the first and second binding antigen-binding molecules when bound to a complex comprising PD-L1 and the PD-L1-binding partner in the sample, wherein an unchanged or lower level of the complex detected in the sample relative to a level of the complex detected in a control sample (e.g., one comprising a normal cell or an epithelial cancer cell) indicates that the cellular compartment of PD-L1 is the cytoplasm and/or cell membrane, that the cancer cell has increased likelihood of sensitivity to the therapy, that the cancer patient is a likely responder to the therapy, that the cancer patient is selected for treatment with the therapy, and/or that the treatment outcome is predicted to be a likely positive treatment outcome.

In related aspects, the present invention provides kits for detecting location of PD-L1 in a cellular compartment (e.g., nucleus) of a cancer cell, for predicting the likelihood of response of a cancer cell to a therapy (e.g., cytotoxic therapy and/or immunotherapy), for determining likelihood of resistance of a cancer cell to a therapy (e.g., cytotoxic therapy and/or immunotherapy), for determining likelihood of sensitivity of a cancer cell to a therapy (e.g., cytotoxic therapy and/or immunotherapy), for stratifying a cancer patient as a likely responder or non-responder to a therapy (e.g., cytotoxic therapy and/or immunotherapy), and/or for managing treatment of a cancer patient with a therapy (e.g., cytotoxic therapy and/or immunotherapy), which kits include (i) a first antigen-binding molecule that binds specifically to PD-L1, (ii) a second antigen-binding molecule that binds specifically to a PD-L1-binding partner selected from P300, DNMT1 and SETDB1; and (iii) a third antigen-binding molecule that binds to the first and second antigen-binding molecules. In specific embodiments, the third antigen-binding molecule comprises a detectable label.

In a related aspect, the present invention provides a complex comprising PD-L1 and a PD-L1-binding partner selected from P300, DNMT1 and SETDB1, a first antigen-binding molecule that is bound specifically to PD-L1 of the complex, a second antigen-binding molecule bound to the PD-L1-binding partner of the complex; and (iii) a third antigen-binding molecule that binds to each of the first and second antigen-binding molecules of the complex. In some embodiments, the PD-L1-PD-L1-binding partner complex is located in a cancer cell. In specific embodiments, the third antigen-binding molecule comprises a detectable label.

In still another aspect, the present invention provides a cancer cell that comprises a complex comprising PD-L1 and a PD-L1-binding partner selected from P300, DNMT1 and SETDB1, a first antigen-binding molecule that is bound specifically to PD-L1 of the complex, a second antigen-binding molecule bound to the PD-L1-binding partner of the complex; and (iii) a third antigen-binding molecule that binds to each of the first and second antigen-binding molecules of the complex. In specific embodiments, the third antigen-binding molecule comprises a detectable label.

In any of the aspects and embodiments described above and elsewhere herein the therapy is suitably an immunotherapy such as but not limited to an immune checkpoint inhibitor, including antagonist antigen-binding molecules (e.g., antibodies) that bind specifically to an immune checkpoint molecule. In representative examples of this type, the antagonist antigen-binding molecules (e.g., antibodies) bind specifically to an immune checkpoint molecule selected from PD-1 and CTLA4. In other embodiments, the therapy is a cytotoxic therapy, suitably a cytotoxic therapy that employs a chemotherapeutic agent.

BRIEF DESCRIPTION OF THE DRAWINGS

FIG. 16 is a list of potential PD-L1 signature gene targets. Key proteins from the above signature marked with an * have also been validated in samples from metastatic melanoma patients. Strikingly almost all of the gene targets are involved with metastasis, recurrence and drug resistance.

Figure 1:
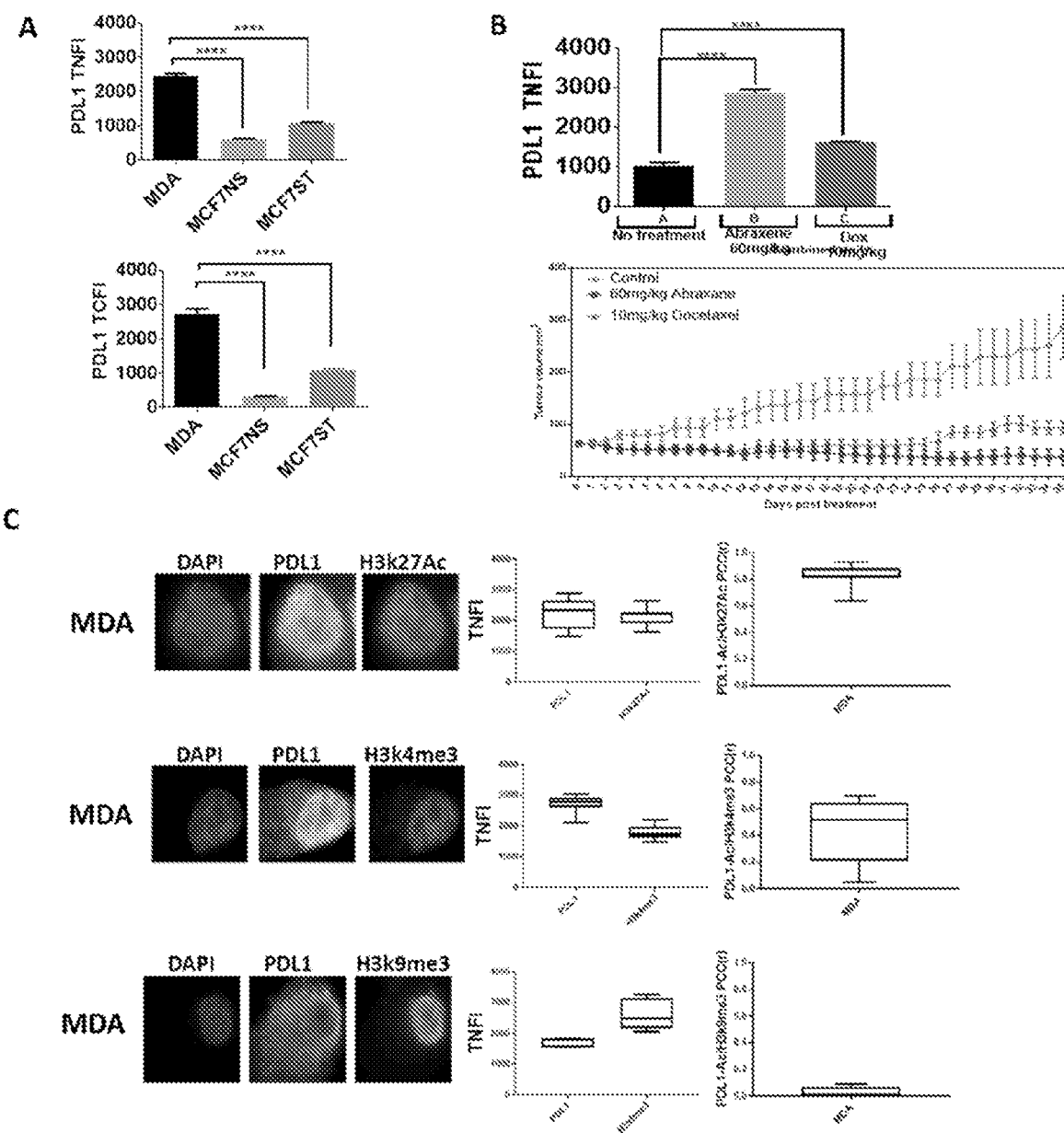
FIG. 1 is a graphical and photographic representation showing prevalence of PD-L1 in mesenchymal CTCs isolated from several metastatic cancers and in chemo-resistant cancer cells, as well as co-localization of PD-L1 with active marks H3k27ac and H3k4me3. (A) MDA-MB-231 or MCF7 cells were probed with a rabbit anti-PD-L1 antibody and digital images were analyzed using ImageJ software (ImageJ, NIH, Bethesda, MD, USA) to determine Total Nuclear Fluorescent Intensity (TNFI) or Total Cytoplasmic Fluorescent Intensity (TCFI) (n>20 cells/sample). (B) Abraxane/Docetaxel xenograft model isolated cancer cells from a primary tumor were probed with a rabbit anti-PD-L1 antibody and Digital images were analyzed using ImageJ software (ImageJ, NIH, Bethesda, MD, USA) to determine TNFI and TCFI (n>20 cells/sample). Depicted in addition is the change in tumor volume in each of the treatment groups. (C) MDA-MB-231 or MCF7 cells were probed with a rabbit anti-PD-L1 antibody and a mouse-anti H3K27ac antibody, H3k4me3 antibody or H3k9me3 antibody and labeled with either a donkey anti-rabbit secondary antibody conjugated to Alexa Fluor 488 or a donkey anti-mouse secondary conjugated to Alexa Fluor 568. ImageJ software with automatic thresholding and manual selection of regions of interest (ROIs) specific for cell nuclei was used to calculate the Pearson's co-efficient correlation (PCC) for each pair of antibodies (n>20 cells/sample).

Some figures and text contain color representations or entities. Color illustrations are available from the Applicant upon request or from an appropriate Patent Office. A fee may be imposed if obtained from a Patent Office.

DETAILED DESCRIPTION OF THE INVENTION

1. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

The term "about" as used herein refers to the usual error range for the respective value readily known to the skilled person in this technical field. Reference to "about" a value or parameter herein includes (and describes) embodiments that are directed to that value or parameter per se.

The terms "administration concurrently" or "administering concurrently" or "co-administering" and the like refer to the administration of a single composition containing two or more actives, or the administration of each active as separate compositions and/or delivered by separate routes either contemporaneously or simultaneously or sequentially within a short enough period of time that the effective result is equivalent to that obtained when all such actives are administered as a single composition. By "simultaneously" is meant that the active agents are administered at substantially the same time, and desirably together in the same formulation. By "contemporaneously" it is meant that the active agents are administered closely in time, e.g., one agent is administered within from about one minute to within about one day before or after another. Any contemporaneous time is useful. However, it will often be the case that when not administered simultaneously, the agents will be administered within about one minute to within about eight hours and suitably within less than about one to about four hours. When administered contemporaneously, the agents are suitably administered at the same site on the subject. The term "same site" includes the exact location, but can be within about 0.5 to about 15 centimeters, preferably from within about 0.5 to about 5 centimeters. The term "separately" as used herein means that the agents are administered at an interval, for example at an interval of about a day to several weeks or months. The active agents may be administered in either order. The term "sequentially" as used herein means that the agents are administered in sequence, for example at an interval or intervals of minutes, hours, days or weeks. If appropriate the active agents may be administered in a regular repeating cycle.

The term "agent" refers to any diagnostic, therapeutic, or preventative agents. The term "agent" is not to be construed narrowly but extends to small molecules, proteinaceous molecules such as peptides, polypeptides and proteins as well as genetic molecules such as RNA, DNA and mimetics and chemical analogs thereof as well as cellular agents. The term "agent" includes a cell that is capable of producing and secreting a polypeptide referred to herein as well as a polynucleotide comprising a nucleotide sequence that encodes that polypeptide. The term "agent" also extends to nucleic acid constructs including vectors such as viral or non-viral vectors, expression vectors and plasmids for expression in and secretion in a range of cells.

"Amplification," as used herein generally refers to the process of producing multiple copies of a desired sequence. "Multiple copies" mean at least two copies. A "copy" does not necessarily mean perfect sequence complementarity or identity to the template sequence. For example, copies can include nucleotide analogs such as deoxyinosine, intentional sequence alterations (such as sequence alterations introduced through a primer comprising a sequence that is hybridizable, but not complementary, to the template), and/or sequence errors that occur during amplification.

The "amount" or "level" of a biomarker is a detectable level or amount in a sample. These can be measured by methods known to one skilled in the art and also disclosed herein. These terms encompass a quantitative amount or level (e.g., weight or moles), a semi-quantitative amount or level, a relative amount or level (e.g., weight % or mole % within class), a concentration, and the like. Thus, these terms encompass absolute or relative amounts or levels or concentrations of a biomarker in a sample. The expression level or amount of biomarker assessed can be used to determine the response to treatment.

As used herein, "and/or" refers to and encompasses any and all possible combinations of one or more of the associated listed items, as well as the lack of combinations when interpreted in the alternative (or).

The term "antagonist" or "inhibitor" refers to a substance that prevents, blocks, inhibits, neutralizes, or reduces a biological activity or effect of another molecule, such as a receptor.

The term "antagonist antibody" refers to an antibody that binds to a target and prevents or reduces the biological effect of that target. In some embodiments, the term can denote an antibody that prevents the target, e.g., PD-1. CTLA4 etc., to which it is bound from performing a biological function.

As used herein, an "anti-immune check point molecule antagonist antibody" refers to an antibody that is able to inhibit the biological activity and/or downstream events(s) mediated by an immune check point molecule. Anti-immune check point molecule antagonist antibodies encompass antibodies that block, antagonize, suppress or reduce (to any degree including significantly) immune check point molecule biological activity, including inhibitory signal transduction through the immune check point molecule and downstream events mediated by the immune check point molecule, such as binding and downstream signaling of an immune check point molecule binding partner to the immune check point molecule, inhibition of cell proliferation, including tumor proliferation, inhibition of T cell proliferation, inhibition of T cell activation, inhibition of cytokine secretion and inhibition of anti-tumor immune responses. For purposes of the present invention, it will be explicitly understood that the term "anti-immune check point molecule antagonist antibody" (interchangeably termed "antagonist immune check point molecule antibody", "antagonist anti-immune check point molecule antibody" or "immune check point molecule antagonist antibody") encompasses all the previously identified terms, titles, and functional states and characteristics whereby the immune check point molecule itself, a biological activity of the immune check point molecule, or the consequences of the biological activity, are substantially nullified, decreased, or neutralized in any meaningful degree.

The term "antibody" herein is used in the broadest sense and specifically covers monoclonal antibodies (including full length monoclonal antibodies), polyclonal antibodies, chimeric antibodies, humanized antibodies, human antibodies, multispecific antibodies (e.g., bispecific antibodies), and single variable domain antibodies so long as they exhibit the desired biological activity. The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (which may be abbreviated as HCVR or $V_H$) and a heavy chain constant region. The heavy chain constant region comprises three domains, $C_{H1}$, $C_{H2}$ and $C_{H3}$. Each light chain comprises a light chain variable region (which may be abbreviated as LCVR or $V_L$) and a light chain constant region. The light chain constant region comprises one domain ($C_{L1}$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of an antibody (or antigen-binding portion thereof) may be identical to the human germline sequences, or may be naturally or artificially modified. An amino acid consensus sequence may be defined based on a side-by-side analysis of two or more CDRs. Included within the scope of the term "antibody" is an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant regions that correspond to the different classes of immunoglobulins are called α, δ, ε, γ, and μ, respectively. The subunit structures and three-dimensional configurations of different classes of immunoglobulins are well known.

An "antigen-binding fragment" may be provided by means of arrangement of one or more CDRs on non-antibody protein scaffolds. "Protein Scaffold" as used herein includes but is not limited to an immunoglobulin (Ig) scaffold, for example an IgG scaffold, which may be a four chain or two chain antibody, or which may comprise only the Fc region of an antibody, or which may comprise one or more constant regions from an antibody, which constant regions may be of human or primate origin, or which may be an artificial chimera of human and primate constant regions. The protein scaffold may be an Ig scaffold, for example an IgG, or IgA scaffold. The IgG scaffold may comprise some or all the domains of an antibody (i.e. CH1, CH2, CH3, $V_H$, $V_L$). The antigen binding protein may comprise an IgG scaffold selected from IgG1, IgG2, IgG3, IgG4 or IgG4PE. For example, the scaffold may be IgG1. The scaffold may consist of, or comprise, the Fc region of an antibody, or is a part thereof. Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g., monovalent nanobodies, bivalent nanobodies, etc.), small modular immunopharmaceuticals (SMIPs), and shark variable IgNAR domains, are also encompassed within the expression "antigen-binding fragment," as used herein. An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain. In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_{H1}$; (ii) $V_H$-$C_{H2}$; (iii) $V_H$-$C_{H3}$; (iv) $V_H$-$C_{H1}$-$C_{H2}$; (v) $V_H$-$C_{H1}$-$C_{H2}$-$C_{H3}$/$V_H$-$C_{H2}$-$C_{H3}$; $V_H$—$C_L$; (viii) $V_L$-$C_{H1}$; (ix) $V_L$-$C_{H2}$; (X) $V_L$-$C_{H3}$; (Xi) $V_L$-$C_{H1}$-$C_{H2}$; (XII) $V_L$-$C_{H1}$-$C_{H2}$-$C_{H3}$; (XIII) $V_L$-$C_{H2}$-$C_{H3}$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)). As with full antibody molecules, antigen-binding fragments may be monospecific or multi-specific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antigen-binding molecule format, including the exemplary bispecific antigen-binding molecule formats disclosed herein, may be adapted for use in the context of an antigen-binding fragment of an antibody of the present invention using routine techniques available in the art.

As used herein, the term "antigen" and its grammatically equivalents expressions (e.g., "antigenic") refer to a compound, composition, or substance that may be specifically bound by the products of specific humoral or cellular immunity, such as an antibody molecule or T-cell receptor. Antigens can be any type of molecule including, for example, haptens, simple intermediary metabolites, sugars (e.g., oligosaccharides), lipids, and hormones as well as macromolecules such as complex carbohydrates (e.g., polysaccharides), phospholipids, and proteins. Common categories of antigens include, but are not limited to, viral antigens, bacterial antigens, fungal antigens, protozoa and other parasitic antigens, tumor antigens, antigens involved in autoimmune disease, allergy and graft rejection, toxins, and other miscellaneous antigens.

By "antigen-binding molecule" is meant a molecule that has binding affinity for a target antigen. It will be understood that this term extends to immunoglobulins, immunoglobulin fragments and non-immunoglobulin derived protein frameworks that exhibit antigen-binding activity. Representative antigen-binding molecules that are useful in the practice of the present invention include antibodies and antigen-binding fragments.

The term "antigen-presenting cell" or "APC" refers to refers to a class of cells capable of presenting one or more antigens in the form of peptide-MHC complex recognizable by specific effector cells of the immune system (also referred to herein as "immune effector cells"), and thereby modulating (e.g., stimulating/enhancing or reducing/tolerizing/anergizing) an immune response to the antigen or antigens being presented. In specific embodiments of the present invention, the APCs are capable of activating immune effector cells such as T lymphocytes, including $CD8^+$ and/or $CD4^+$ lymphocytes. Cells that have in vivo the potential to act as APC include, for example, not only professional APCs such as dendritic cells, macrophages, Langerhans cell, monocytes and B cells but also non-professional APCs illustrative examples of which include activated epithelial cells, fibroblasts, glial cells, pancreatic beta cells and vascular endothelial cells, as well as cancer cells. Many types of cells are capable of presenting antigens on their cell surface for immune effector cell, including T cell, recognition.

As used herein, the term "antigen-specific" refers to a property of a cell population such that supply of a particular antigen, or a fragment of the antigen, results in specific cell proliferation, suitably T-cell proliferation characterized for example by activation of the T-cells (e.g., CTLs and/or helper T cells) that are suitably directed against a damaged cell, malignancy or infection.

As use herein, the term "binds", "specifically binds to" or is "specific for" refers to measurable and reproducible interactions such as binding between a target and an antibody, which is determinative of the presence of the target in the presence of a heterogeneous population of molecules including biological molecules. For example, an antibody that binds to or specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to a target has a dissociation constant (Kd) of ≤1 μM, ≤100 nM, ≤10 nM, ≤1 nM, or ≤0.1 nM. In certain embodiments, an antibody specifically binds to an epitope on a protein that is conserved among the protein from different species. In another embodiment, specific binding can include, but does not require exclusive binding.

The term "biomarker" as used herein refers to an indicator, e.g., predictive, diagnostic, and/or prognostic, which can be detected in a sample. The biomarker may serve as an indicator of a particular subtype of a disease or disorder (e.g., cancer), characterized by certain, molecular, pathological, histological, and/or clinical features, and/or may serve as an indicator of a particular cell type or state (e.g., epithelial, mesenchymal etc.) and/or or response to therapy. Biomarkers include, but are not limited to, polynucleotides (e.g., DNA, and/or RNA), polynucleotide copy number alterations (e.g., DNA copy numbers), polypeptides, polypeptide and polynucleotide modifications (e.g., posttranslational modifications), carbohydrates, and/or glycolipid-based molecular markers. A biomarker may be present in a sample obtained from a subject before the onset of a physiological or pathophysiological state (e.g., primary cancer, metastatic cancer, etc.), including a symptom, thereof (e.g., response to therapy). Thus, the presence of the biomarker in a sample obtained from the subject can be indicative of an increased risk that the subject will develop the physiological or pathophysiological state or symptom thereof. Alternatively, or in addition, the biomarker may be normally expressed in an individual, but its expression may change (i.e., it is increased (upregulated; over-expressed) or decreased (downregulated; under-expressed) before the onset of a physiological or pathophysiological state, including a symptom thereof. Thus, a change in the level of the biomarker may be indicative of an increased risk that the subject will develop the physiological or pathophysiological state or symptom thereof. Alternatively, or in addition, a change in the level of a biomarker may reflect a change in a particular physiological or pathophysiological state, or symptom thereof, in a subject, thereby allowing the nature (e.g., severity) of the physiological or pathophysiological state, or symptom thereof, to be tracked over a period of time. This approach may be useful in, for example, monitoring a treatment regimen for the purpose of assessing its effectiveness (or otherwise) in a subject. As herein described, reference to the level of a biomarker includes the concentration of a biomarker, or the level of expression of a biomarker, or the activity of the biomarker.

The terms "biomarker signature", "signature", "biomarker expression signature", or "expression signature" are used interchangeably herein and refer to one or a combination of biomarkers whose expression is an indicator, e.g., predictive, diagnostic, and/or prognostic. The biomarker signature may serve as an indicator of a particular subtype of a disease or disorder (e.g., primary cancer, metastatic cancer, etc.) or symptom thereof (e.g., response to therapy, drug resistance, and/or disease burden) characterized by certain molecular, pathological, histological, and/or clinical features. In some embodiments, the biomarker signature is a "gene signature." The term "gene signature" is used interchangeably with "gene expression signature" and refers to one or a combination of polynucleotides whose expression is an indicator, e.g., predictive, diagnostic, and/or prognostic. In some embodiments, the biomarker signature is a "protein signature." The term "protein signature" is used interchangeably with "protein expression signature" and refers to one or a combination of polypeptides whose expression is an indicator, e.g., predictive, diagnostic, and/or prognostic. A biomarker signature may comprise at least 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 or more biomarkers.

The terms "cancer" and "cancerous" refer to or describe the physiological condition in subjects that is typically characterized by unregulated cell growth, with potential to invade locally and/or spread to other parts of the body (metastasize). The term "cancer" is generally used interchangeably with "tumor" herein (unless a tumor is specifically referred to as a "benign" tumor, which is an abnormal mass of cells that lacks the ability to invade neighboring tissue or metastasize), and encompasses malignant solid tumors (e.g., carcinomas, sarcomas) and malignant growths in which there may be no detectable solid tumor mass (e.g., certain hematologic malignancies). Non-limiting examples of cancers include but are not limited to, carcinoma, lymphoma, blastoma, sarcoma, and leukemia or lymphoid malignancies. More particular examples of such cancers include, but not limited to, squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer and gastrointestinal stromal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, superficial spreading melanoma, lentigo maligna melanoma, acral lentiginous melanomas, nodular melanomas, multiple myeloma and B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); hairy cell leukemia; chronic myeloblastic leukemia; and post-transplant lymphoproliferative disorder (PTLD), as well as abnormal vascular proliferation associated with phacomatoses, edema (such as that associated with brain tumors), Meigs' syndrome, brain, as well as head and neck cancer, and associated metastases. In certain embodiments, cancers that are amenable to treatment by the antibodies of the invention include breast cancer, colorectal cancer, rectal cancer, non-small cell lung cancer, glioblastoma, non-Hodgkin's lymphoma (NHL), renal cell cancer, prostate cancer, liver cancer, pancreatic cancer, soft-tissue sarcoma, Kaposi's sarcoma, carcinoid carcinoma, head and neck cancer, ovarian cancer, mesothelioma, and multiple myeloma. In some embodiments, the cancer is selected from: small cell lung cancer, glioblastoma, neuroblastomas, melanoma, breast carcinoma, gastric cancer, colorectal cancer (CRC), and hepatocellular carcinoma. Yet in some embodiments, the cancer is selected from: non-small cell lung cancer, colorectal cancer, glioblastoma and breast carcinoma, including metastatic forms of those cancers. In specific embodiments, the cancer is melanoma or lung cancer, suitably metastatic melanoma or metastatic lung cancer.

The term "cellular compartment" includes a part of a cell including organelles (such as mitochondria, Golgi apparatus, endoplasmic reticulum, ribosomes, etc.), the nucleus, the cytoplasm (optionally including the organelles), the nuclear membrane, the cell membrane and other cellular regions.

The term "chemotherapy" refers to a therapy of a human or animal with one or more chemotherapeutic agents, which inhibit or abrogate cell growth and cell division, namely, the therapy is taken as a cell proliferation inhibitor or is used for inducing cell death (cell apoptosis). Compared with normal cells, cancer cells grow and divide uncontrollably so that the chemotherapy should be more effective to the cancer cells.

The term "chemotherapeutic agent" refers to chemical compounds that are effective in inhibiting tumor growth. Examples of chemotherapeutic agents include erlotinib (TARCEVA®, Genentech/OSI Pharm.), bortezomib (VELCADE®, Millennium Pharm.), disulfiram, epigallocatechin gallate, salinosporamide A, carfilzomib, 17-AAG (geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (*Angew Chem. Intl. Ed. Engl.* 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Chemotherapeutic agent also includes (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifine citrate); (H) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) antiandrogens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-α, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; and (ix) pharmaceutically acceptable salts, acids and derivatives of any of the above.

Chemotherapeutic agent also includes antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizunnab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length $IgG_1$ λ antibody genetically modified to recognize interleukin-12 p40 protein.

Chemotherapeutic agent also includes "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL H68507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al., Eur. J. Cancer 32A:636-640 (1996)); EMD7200 (matuzumab) a humanized EGFR antibody directed against EGFR that competes with both EGF and TGF-α for EGFR binding (EMD/Merck); human EGFR antibody, HuMax-EGFR (GenMab); fully human antibodies known as E1.1, E2.4, E2.5, E6.2, E6.4, E2.11, E6. 3 and E7.6. 3 and described in U.S. Pat. No. 6,235,883; MDX-447 (Medarex Inc); and mAb 806 or humanized mAb 806 (Johns et al., J. Biol. Chem. 279(29): 30375-30384 (2004)). The anti-EGFR antibody may be conjugated with a cytotoxic agent, thus generating an immunoconjugate (see, e.g., EP659439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl) propoxy]-6-quin-azolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol)-; (R)-6-(4-hydroxyphenyl)-4-[(1-phenylethypamino]-7H-pyrrolo[2,3-d]pyrimi-dine); CL-387785

(N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(–dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3 fluorophenyl)methoxy]phenyl]-6[5[[[2methylsulfonyl)ethyl]amino]methyl]-2--furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitor such as TAK165 available from Takeda; CP-724,714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from GlaxoSmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035, 4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d] pyrimidines; curcumin (diferuloyl methane, 4,5-bis (4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804,396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); innatinib mesylate (GLEEVEC®); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca).

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN Bio-Therapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor α (TNF-α) blockers such as etanercept (Enbrel), infliximab (Remicade), adalimumab (Humira), certolizumab pegol (Cimzia), golimumab (Simponi), Interleukin 1 (IL-1) blockers such as anakinra (Kineret), T-cell costimulation blockers such as abatacept (Orencia), Interleukin 6 (IL-6) blockers such as tocilizumab (ACTEMERA®); Interleukin 13 (IL-13) blockers such as lebrikizumab; Interferon α (IFN) blockers such as Rontalizumab; Beta 7 integrin blockers such as rhuMAb Beta7; IgE pathway blockers such as Anti-M1 prime; Secreted homotrimeric LTa3 and membrane bound heterotrimer LTa1/132 blockers such as Anti-lymphotoxin α (LTa); radioactive isotopes (e.g., At211, I131, I125, Y90, Re186, Re188, Sm153, Bi212, P32, Pb212 and radioactive isotopes of Lu); miscellaneous investigational agents such as thioplatin, PS-341, phenylbutyrate, ET-18-OCH3, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g. celecoxib or etoricoxib), proteosome inhibitor (e.g. PS341); CCI-779; tipifarnib (R11577); orafenib, ABT510; Bcl-2 inhibitor such as oblimersen sodium (GENASENSE®); pixantrone; farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATINT™) combined with 5-FU and leucovorin.

Chemotherapeutic agents also include non-steroidal anti-inflammatory drugs with analgesic, antipyretic and anti-inflammatory effects. NSAIDs include non-selective inhibitors of the enzyme cyclooxygenase. Specific examples of NSAIDs include aspirin, propionic acid derivatives such as ibuprofen, fenoprofen, ketoprofen, flurbiprofen, oxaprozin and naproxen, acetic acid derivatives such as indomethacin, sulindac, etodolac, diclofenac, enolic acid derivatives such as piroxicam, meloxicam, tenoxicam, droxicam, lornoxicam and isoxicam, fenamic acid derivatives such as mefenamic acid, meclofenamic acid, flufenamic acid, tolfenamic acid, and COX-2 inhibitors such as celecoxib, etoricoxib, lumiracoxib, parecoxib, rofecoxib, rofecoxib, and valdecoxib. NSAIDs can be indicated for the symptomatic relief of conditions such as rheumatoid arthritis, osteoarthritis, inflammatory arthropathies, ankylosing spondylitis, psoriatic arthritis, Reiter's syndrome, acute gout, dysmenorrhea, metastatic bone pain, headache and migraine, postoperative pain, mild-to-moderate pain due to inflammation and tissue injury, pyrexia, ileus, and renal colic.

The term "clinical outcome" or "clinical endpoint" refers to any clinical observation or measurement relating to a patient's reaction to a therapy. Non-limiting examples of clinical outcomes include tumor response (TR), overall survival (OS), progression free survival (PFS), disease free survival (DFS), time to tumor recurrence (TTR), time to tumor progression (TTP), relative risk (RR), toxicity or side effect. "Overall Survival" (OS) intends a prolongation in life expectancy as compared to naive or untreated individuals or patients. "Progression free survival" (PFS) or "Time to tumor progression" (TTP) indicates the length of time during and after treatment that the cancer does not grow. Progression-free survival includes the amount of time patients have experienced a complete response or a partial response, as well as the amount of time patients have experienced stable disease. "Tumor recurrence" as used herein and as defined by the National Cancer Institute is cancer that has recurred (come back), usually after a period of time during which the cancer could not be detected. The cancer may come back to the same place as the original (primary) tumor or to another place in the body. It is also called recurrent cancer. "Time to tumor recurrence" (TTR) is defined as the time from the date of diagnosis of the cancer to the date of first recurrence, death, or until last contact if the patient was free of any tumor recurrence at the time of last contact. If a patient had not recurred, then TTR was censored at the time of death or at the last follow-up. "Relative risk" (RR), in statistics and mathematical epidemiology, refers to the risk of an event (or of developing a disease) relative to exposure. Relative risk is a ratio of the probability of the event occurring in the exposed group versus a non-exposed group.

As used herein, the term "complex" refers to an assemblage or aggregate of molecules (e.g., peptides, polypeptides, etc.) in direct and/or indirect contact with one another. In specific embodiments, "contact", or more particularly, "direct contact" means two or more molecules are close enough so that attractive noncovalent interactions, such as Van der Waal forces, hydrogen bonding, ionic and hydrophobic interactions, and the like, dominate the interaction of the molecules. In such embodiments, a complex of molecules (e.g., a peptide and polypeptide) is formed under conditions such that the complex is thermodynamically favored (e.g., compared to a non-aggregated, or non-complexed, state of its component molecules). The term "polypeptide complex" or "protein complex," as used herein, refers to a trimer, tetramer, pentamer, hexamer, heptamer, octamer, nonamer, decamer, undecamer, dodecamer, or higher order oligomer. In specific embodiments, the polypeptide complexes are formed by binding of PD-L1 with one or more of the lysine acetyltransferase, P300, and the methyltransferases DNMT1 and SETDB1.

Throughout this specification, unless the context requires otherwise, the words "comprise," "comprises" and "comprising" will be understood to imply the inclusion of a stated step or element or group of steps or elements but not the exclusion of any other step or element or group of steps or elements. Thus, use of the term "comprising" and the like indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

As used herein, the term "correlates" or "correlates with" and like terms, refers to a statistical association between two or more things, such as events, characteristics, outcomes, numbers, data sets, etc., which may be referred to as "variables". It will be understood that the things may be of different types. Often the variables are expressed as numbers (e.g., measurements, values, likelihood, risk), wherein a positive correlation means that as one variable increases, the other also increases, and a negative correlation (also called anti-correlation) means that as one variable increases, the other variable decreases.

By "corresponds to" or "corresponding to" is meant an amino acid sequence that displays substantial sequence similarity or identity to a reference amino acid sequence. In general the amino acid sequence will display at least about 70, 71, 72, 73, 74, 75, 76, 77, 78, 79, 80, 81, 82, 83, 84, 85, 86, 97, 88, 89, 90, 91, 92, 93, 94, 95, 96, 97, 98, 99% or even up to 100% sequence similarity or identity to at least a portion of the reference amino acid sequence.

The term "cytotoxic agent" as used herein refers to any agent that is detrimental to cells (e.g., causes cell death, inhibits proliferation, or otherwise hinders a cellular function). Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents; growth inhibitory agents; enzymes and fragments thereof such as nucleolytic enzymes; and toxins such as small molecule toxins or enzymatically active toxins of bacterial, fungal, plant or animal origin, including fragments and/or variants thereof. Exemplary cytotoxic agents can be selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A, inhibitors of fatty acid biosynthesis, cell cycle signaling inhibitors, HDAC inhibitors, proteasome inhibitors, and inhibitors of cancer metabolism. In some embodiments, the cytotoxic agent is a taxane. In representative examples of this type, the taxane is paclitaxel or docetaxel. In some embodiments, the cytotoxic agent is a platinum agent. In some embodiments, the cytotoxic agent is an antagonist of EGFR. In representative examples of this type, the antagonist of EGFR is N-(3-ethynylphenyl)-6,7-bis(2- methoxyethoxy)quinazolin-4-amine (e.g., erlotinib). In some embodiments, the cytotoxic agent is a RAF inhibitor. In non-limiting examples of this type, the RAF inhibitor is a BRAF and/or CRAF inhibitor. In other non-limiting examples, the RAF inhibitor is vemurafenib. In one embodiment the cytotoxic agent is a PI3K inhibitor.

As used herein, the term "cytotoxic therapy" refers to therapies that induce cellular damage including but not limited to radiation, chemotherapy, photodynamic therapy, radiofrequency ablation, anti-angiogenic therapy, and combinations thereof. A cytotoxic therapeutic may induce DNA damage when applied to a cell.

As used herein, "delaying progression of a disease" or "decreasing the rate of progression of a disease" means to defer, hinder, slow, retard, stabilize, and/or postpone development of the disease (such as a cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

The term "detection" includes any means of detecting, including direct and indirect detection.

The term "drug" as used herein refers to any substance having biological or detectable activity in vivo. The term drug is meant to encompass cytotoxic agents, cytostatic agents, anti-angiogenic agents, debulking agents, chemotherapeutic agents, radiotherapeutic agents, targeted anticancer agents, biological response modifiers, cancer vaccines, cytokines, hormone therapies, anti-metastatic agents and immunotherapeutic agents.

The term "drug resistance" refers to the condition when a disease does not respond to the treatment of a drug or drugs. Drug resistance can be either intrinsic (or primary resistance), which means the disease has never been responsive to the drug or drugs, or it can be acquired, which means the disease ceases responding to a drug or drugs that the disease had previously responded to (secondary resistance). In certain embodiments, drug resistance is intrinsic. In certain embodiments, the drug resistance is acquired.

An "effective amount" is at least the minimum amount required to effect a measurable improvement or prevention of a particular disorder. An effective amount herein may vary according to factors such as the disease state, age, sex, and weight of the patient, and the ability of the antibody to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of cancer or tumor, an effective amount of the drug may have the effect in reducing the number of cancer cells; reducing the tumor size; inhibiting (i.e., slow to some extent or desirably stop) cancer cell infiltration into peripheral organs; inhibit (i.e., slow to some extent and desirably stop) tumor metastasis; inhibiting to some extent tumor growth; and/or relieving to some extent one or more of the symptoms associated with the cancer or tumor. An effective amount can be administered in one or more administrations. For purposes of this invention, an effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved. The effective amount of a treatment can be measured by various endpoints commonly used in evaluating cancer treatments, including, but not limited to: extending survival (including overall survival (OS) and progression free survival (PFS)); resulting in an objective response (including a complete response (CR) or a partial response (PR)); tumor regression, tumor weight or size shrinkage, longer time to disease progression, increased duration of survival, longer PFS, improved OS rate, increased duration of response, and improved quality of life and/or improving signs or symptoms of cancer. As used herein, the term "progressive disease" (PD) refers to least a 20% increase in the sum of diameters of target lesions, taking as reference the smallest sum on study (this includes the baseline sum if that is the smallest on study). In addition to the relative increase of 20%, the sum must also demonstrate an absolute increase of at least 5 mm The appearance of one or more new lesions is also considered progression. As used herein, the term "partial response" (PR) refers to at least a 30% decrease in the sum of diameters of target lesions, taking as reference the baseline sum diameters. As used herein, the term "complete response" (CR) refers to the disappearance of all non-nodal target lesions with the short axes of any target lymph nodes reduced to <10 mm. As used herein, the term "stable disease" (SD) refers to neither sufficient shrinkage for PR nor sufficient increase to qualify for PD, taking as reference the smallest sum of diameters while on study.

The terms "epithelial", "epithelial phenotype" and the like are understood in the art, and can be identified by morphological, molecular and/or functional characteristics. For example, epithelial cells generally have a rounded or cobblestone appearance, express the epithelial marker E-cadherin, are rapidly dividing and/or have relatively low levels of motility, invasiveness and/or anchorage-independent growth as compared with mesenchymal cells.

As used herein, the term "epithelial-to-mesenchymal transition" (EMT) refers to the conversion from an epithelial to a mesenchymal phenotype, which is a normal process of embryonic development. EMT is also the process whereby injured epithelial cells that function as ion and fluid transporters become matrix remodeling mesenchymal cells. In carcinomas, this transformation typically results in altered cell morphology, the expression of mesenchymal proteins and increased invasiveness. The criteria for defining EMT in vitro involve the loss of epithelial cell polarity, the separation into individual cells and subsequent dispersion after the acquisition of cell motility (see, Vincent-Salomon et al., *Breast Cancer Res.* 2003; 5(2): 101-106). Classes of molecules that change in expression, distribution, and/or function during EMT, and that are causally involved, include growth factors (e.g., transforming growth factor-β (TGF-β), wnts), transcription factors (e.g., Snail, SMAD, LEF, and nuclear β-catenin), molecules of the cell-to-cell adhesion axis (cadherins, catenins), cytoskeletal modulators (Rho family), and extracellular proteases (matrix metalloproteinases, plasminogen activators) (see, Thompson et al., *Cancer Research* 65, 5991-5995, Jul. 15, 2005). In specific embodiments, EMT refers to a process whereby epithelial cancer cells take on a mesenchymal phenotype, which may be associated with metastasis. These mesenchymal cells may display reduced adhesiveness, increased motility and invasiveness and are relatively resistant to immunotherapeutic agents, chemotherapeutic agents and/or radiation (e.g., treatments that target rapidly dividing cells).

The term "epitope" refers to that portion of a molecule capable of being recognized by and bound by an antibody at one or more of the antibody's antigen-binding portions. Epitopes often consist of a surface grouping of molecules such as amino acids or sugar side chains and have specific three-dimensional structural characteristics as well as specific charge characteristics. In some embodiments, the epitope can be a protein epitope. Protein epitopes can be linear or conformational. In a linear epitope, all of the points of interaction between the protein and the interacting molecule (such as an antibody) occur linearly along the primary amino acid sequence of the protein. A "non-linear epitope" or "conformational epitope" comprises non-contiguous polypeptides (or amino acids) within the antigenic protein to which an antibody specific to the epitope binds. Once a desired epitope on an antigen is determined, it is possible to generate antibodies to that epitope, e.g., using the techniques described in the present specification. Alternatively, during the discovery process, the generation and characterization of antibodies may elucidate information about desirable epitopes. From this information, it is then possible to competitively screen antibodies for binding to the same epitope. An approach to achieve this is to conduct competition and cross-competition studies to find antibodies that compete or cross-compete with one another for binding to a target antigen (e.g., PD-L1-K263Ac, PD-L1-K263Me, etc.), e.g., the antibodies compete for binding to the antigen.

The term "expression" with respect to a gene sequence refers to transcription of the gene to produce a RNA transcript (e.g., mRNA, antisense RNA, siRNA, shRNA, miRNA, etc.) and, as appropriate, translation of a resulting mRNA transcript to a protein. Thus, as will be clear from the context, expression of a coding sequence results from transcription and translation of the coding sequence. Conversely, expression of a non-coding sequence results from the transcription of the non-coding sequence.

As used herein, the term "increase" or "increased" with reference to a biomarker or biomarker complex level refers to a statistically significant and measurable increase in the biomarker or biomarker complex level compared to the level of another biomarker or biomarker complex or to a control level. The increase is preferably an increase of at least about 10%, or an increase of at least about 20%, or an increase of at least about 30%, or an increase of at least about 40%, or an increase of at least about 50%.

As used herein, the term "higher" with reference to a biomarker or biomarker complex measurement refers to a statistically significant and measurable difference in the level of a biomarker or biomarker complex measurement compared to the level of another biomarker or biomarker complex or to a control level where the biomarker or biomarker complex measurement is greater than the level of the other biomarker or biomarker complex or the control level. The difference is preferably at least about 10%, or at least about 20%, or of at least about 30%, or of at least about 40%, or at least about 50%.

As used herein, the term "reduce" or "reduced" with reference to a biomarker or biomarker complex level refers to a statistically significant and measurable reduction in the biomarker or biomarker complex level compared to the level of another biomarker or biomarker complex or to a control level. The reduction is preferably a reduction of at least about 10%, or a reduction of at least about 20%, or a reduction of at least about 30%, or a reduction of at least about 40%, or a reduction of at least about 50%.

As used herein, the term "lower" with reference to a biomarker or biomarker complex measurement refers to a statistically significant and measurable difference in the level of a biomarker or biomarker complex measurement compared to the level of another biomarker or biomarker complex or to a control level where the biomarker or biomarker complex measurement is less than the level of the other biomarker or biomarker complex or the control level. The difference is preferably at least about 10%, or at least about 20%, or of at least about 30%, or of at least about 40%, or at least about 50%.

The terms "level of expression" or "expression level" in general are used interchangeably and generally refer to the amount of a biomarker in a sample. "Expression" generally refers to the process by which information (e.g., gene-encoded and/or epigenetic) is converted into the structures present and operating in the cell. Therefore, as used herein, "expression" may refer to transcription into a polynucleotide, translation into a polypeptide, or even polynucleotide and/or polypeptide modifications (e.g., posttranslational modification of a polypeptide). Fragments of the transcribed polynucleotide, the translated polypeptide, or polynucleotide and/or polypeptide modifications (e.g., post-translational modification of a polypeptide) shall also be regarded as expressed whether they originate from a transcript generated by alternative splicing or a degraded transcript, or from a post-translational processing of the polypeptide, e.g., by proteolysis. "Expressed genes" include those that are transcribed into a polynucleotide as mRNA and then translated into a polypeptide, and also those that are transcribed into RNA but not translated into a polypeptide (e.g., transfer and ribosomal RNAs). Thus, "elevated expression", "elevated expression levels", or "elevated levels" refers to an increased expression or increased levels of a biomarker in a cell or individual relative to a control, such as a cell or cells that are responding or not responding to a therapy, or an individual or individuals who are responding or not responding to a therapy, or an internal control (e.g., housekeeping biomarker). "Reduced expression", "reduced expression levels", or "reduced levels" refers to a decreased expression or decreased levels of a biomarker in an individual relative to a control, such as a cell or cells that are responding or not responding to a therapy, or an individual or individuals who are responding or not responding to a therapy, an internal control (e.g., housekeeping biomarker). In some embodiments, reduced expression is little or no expression. In specific embodiments, an elevated level of PD-L1-K263Ac refers to a level that correlates with a largely nuclear localization of PD-L1 or a localization that is higher in the nucleus than in the cytoplasm and/or cell membrane. In other embodiments, an elevated level of PD-L1-K263Me refers to a level that correlates with a largely cytoplasmic and/or cell membrane localization of PD-L1 or a localization that is higher in the cytoplasm and/or cell membrane than in the nucleus.

The term "housekeeping biomarker" refers to a biomarker or group of biomarkers (e.g., polynucleotides and/or polypeptides) which are typically similarly present in all cell types. In some embodiments, the housekeeping biomarker is a "housekeeping gene." A "housekeeping gene" refers herein to a gene or group of genes which encode proteins whose activities are essential for the maintenance of cell function and which are typically similarly present in all cell types.

A "growth inhibitory agent" when used herein refers to a compound or composition which inhibits growth of a cell either in vitro or in vivo. In one embodiment, growth inhibitory agent is growth inhibitory antibody that prevents or reduces proliferation of a cell expressing an antigen to which the antibody binds. In another embodiment, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn and Israel, eds., The Molecular Basis of Cancer, Chapter 1, entitled "Cell cycle regulation, oncogenes, and antineoplastic drugs" by Murakami et al. (W.B. Saunders, Philadelphia, 1995), e.g., p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

The term "immune checkpoint molecule" includes both receptors and ligands that function as an immune checkpoint. Immune checkpoints represent immune escape mechanisms to prevent the immune system from attacking its own body. Immune checkpoint receptors are present on T cells, and interact with immune checkpoint ligands expressed on antigen-presenting cells, including cancer cells. T cells recognize an antigen presented on the MHC molecule and are activated to generate an immune reaction, whereas an interaction between immune checkpoint receptor and ligand that occurs in parallel with the above controls the activation of T cells. Immune checkpoint receptors include co-stimulatory receptors and inhibitory receptors, and the T cell activation and the immune reaction are controlled by a balance between both receptors. Illustrative immune checkpoint molecules that may be targeted for blocking or inhibition include, but are not limited to, CTLA-4, 4-1BB (CD137), 4-1BBL (CD137L), PD-L1, PD-L2, PD-1, B7-H3, B7-H4, BTLA, HVEM, TIM3, GAL9, LAG3, TIM3, B7H3, B7H4, VISTA, KIR, 2B4 (belongs to the CD2 family of molecules and is expressed on all NK, γδ, and memory CD8+ (αβ) T cells), CD160 (also referred to as BY55) and CGEN-15049.

As used herein, the term "immune checkpoint inhibitor" or "checkpoint inhibitor" refers to any agent, molecule, compound, chemical, protein, polypeptide, macromolecule, etc. that totally or partially reduce, inhibit, interfere with or modulate one or more immune checkpoint molecules. Such inhibitors may include small molecule inhibitors or may include antigen-binding molecules that bind to and block or inhibit immune checkpoint receptors or antibodies that bind to and block or inhibit immune checkpoint receptor ligands. Illustrative immune checkpoint inhibitors include anti-immune checkpoint molecule antagonist antibodies such as, but not limited to, durvalumab (anti-PD-L1 antibody; MEDI4736), pembrolizumab (anti-PD-1 monoclonal antibody), nivolumab (anti-PD-1 antibody), pidilizumab (CT-011; humanized anti-PD-1 monoclonal antibody), AMP224 (recombinant B7-DC-Fc fusion protein), BMS-936559 (anti-PD-L1 antibody), atezolizumab (MPLDL3280A; human Fc-optimized anti-PD-L1 monoclonal antibody), avuelumab (MSB0010718C; human anti-PD-L1 antibody), ipilimumab (anti-CTLA-4 checkpoint inhibitor), tremelimumab (CTLA-4 blocking antibody), and anti-OX40.

The term "immune effector cells" in the context of the present invention relates to cells which exert effector functions during an immune reaction. For example, such cells secrete cytokines and/or chemokines, kill microbes, secrete antibodies, recognize infected or cancerous cells, and optionally eliminate such cells. For example, immune effector cells comprise T-cells (cytotoxic T-cells, helper T-cells, tumor infiltrating T-cells), B-cells, natural killer (NK) cells, lymphokine-activated killer (LAK) cells, neutrophils, macrophages, and dendritic cells.

The term "immune response" refers to any detectable response to a particular substance (such as an antigen or immunogen) by the immune system of a host mammal, such as innate immune responses (e.g., activation of Toll receptor signaling cascade), cell-mediated immune responses (e.g., responses mediated by T cells, such as antigen-specific T cells, and non-specific cells of the immune system), and humoral immune responses (e.g., responses mediated by B cells, such as generation and secretion of antibodies into the plasma, lymph, and/or tissue fluids).

The term "immunotherapy" refers to any therapy in which one or more components of a human's or animal's immune system is deliberately modulated in order to directly or indirectly achieve some therapeutic benefit, including systemic and/or local effects, and preventative and/or curative effects. Immunotherapy can involve administering one or more immunotherapeutic agents, either alone or in any combination, to a human or animal subject by any route (e.g., orally, intravenously, dermally, by injection, by inhalation, etc.), whether systemically, locally or both. Immunotherapy can involve provoking, increasing, decreasing, halting, preventing, blocking or otherwise modulating the production of cytokines, and/or activating or deactivating cytokines or immune cells, and/or modulating the levels of immune cells, and/or delivering one or more therapeutic or diagnostic substances to a particular location in the body or to a particular type of cell or tissue, and/or destroying particular cells or tissue. Immunotherapy can be used to achieve local effects, systemic effects or a combination of both.

The term "immunotherapeutic agent" as used herein refers to any agent, compound, or biologic that indirectly or directly restores, enhances, stimulates or increases the body's immune response against cancer cells and/or that decreases the side effects of other anticancer therapies. Immunotherapy is thus a therapy that directly or indirectly stimulates or enhances the immune system's responses to cancer cells and/or lessens the side effects that may have been caused by other anti-cancer agents. Immunotherapy is also referred to in the art as immunologic therapy, biological therapy biological response modifier therapy and biotherapy.

Examples of common immunotherapeutic agents known in the art include, but are not limited to, cytokines, cancer vaccines, monoclonal antibodies and non-cytokine adjuvants. Alternatively, the immunotherapeutic treatment may consist of administering the subject with an amount of immune cells (T cells, NK, cells, dendritic cells, B cells, etc.). Immunotherapeutic agents can be non-specific, i.e., boost the immune system generally so that the human body becomes more effective in fighting the growth and/or spread of cancer cells, or they can be specific, i.e., targeted to the cancer cells themselves. Immunotherapy regimens may combine the use of non-specific and specific immunotherapeutic agents. Non-specific immunotherapeutic agents are substances that stimulate or indirectly improve the immune system. Non-specific immunotherapeutic agents have been used alone as a main therapy for the treatment of cancer, as well as in addition to a main therapy, in which case the non-specific immunotherapeutic agent functions as an adjuvant to enhance the effectiveness of other therapies (e.g., cancer vaccines). Non-specific immunotherapeutic agents can also function in this latter context to reduce the side effects of other therapies, for example, bone marrow suppression induced by certain chemotherapeutic agents. Non-specific immunotherapeutic agents can act on key immune system cells and cause secondary responses, such as increased production of cytokines and immunoglobulins. Alternatively, the agents can themselves comprise cytokines. Non-specific immunotherapeutic agents are generally classified as cytokines or non-cytokine adjuvants. A number of cytokines have found application in the treatment of cancer either as general non-specific immunotherapies designed to boost the immune system, or as adjuvants provided with other therapies. Suitable cytokines include, but are not limited to, interferons, interleukins and colony-stimulating factors. Interferons (IFNs) contemplated by the present invention include the common types of IFNs, IFN-alpha (IFN-α), IFN-beta (IFN-β) and IFN-gamma (IFN-γ). IFNs can act directly on cancer cells, for example, by slowing their growth, promoting their development into cells with more normal behaviour and/or increasing their production of antigens thus making the cancer cells easier for the immune system to recognise and destroy. IFNs can also act indirectly on cancer cells, for example, by slowing down angiogenesis, boosting the immune system and/or stimulating natural killer (NK) cells, T cells and macrophages. Recombinant IFN-alpha is available commercially as Roferon (Roche Pharmaceuticals) and Intron A (Schering Corporation). Interleukins contemplated by the present invention include IL-2, IL-4, IL-11 and IL-12. Examples of commercially available recombinant interleukins include Proleukin® (IL-2; Chiron Corporation) and Neumega® (IL-12; Wyeth Pharmaceuticals). Zymogenetics, Inc. (Seattle, Wash.) is currently testing a recombinant form of IL-21, which is also contemplated for use in the combinations of the present invention. Colony-stimulating factors (CSFs) contemplated by the present invention include granulocyte colony stimulating factor (G-CSF or filgrastim), granulocyte-macrophage colony stimulating factor (GM-CSF or sargramostim) and erythropoietin (epoetin alfa, darbopoietin). Treatment with one or more growth factors can help to stimulate the generation of new blood cells in subjects undergoing traditional chemotherapy. Accordingly, treatment with CSFs can be helpful in decreasing the side effects associated with chemotherapy and can allow for higher doses of chemotherapeutic agents to be used. Various-recombinant colony stimulating factors are available commercially, for example, Neupogen® (G-CSF; Amgen), Neulasta (pelfilgrastim; Amgen), Leukine (GM-CSF; Berlex), Procrit (erythropoietin; Ortho Biotech), Epogen (erythropoietin; Amgen), Aranesp (erythropoietin). In addition to having specific or non-specific targets, immunotherapeutic agents can be active, i.e., stimulate the body's own immune response including humoral and cellular immune responses, or they can be passive, i.e., comprise immune system components such as antibodies, effector immune cells, antigen-presenting cells etc. that were generated external to the body. In specific embodiments, passive immunotherapy involves the use of one or more monoclonal antibodies that are specific for a particular antigen found on the surface of a cancer cell or immune cell or that are specific for a particular cell growth factor. Monoclonal antibodies may be used in the treatment of cancer in a number of ways, for example, to enhance a subject's immune response to a specific type of cancer, to interfere with the growth of cancer cells by targeting specific cell growth factors, such as those involved in angiogenesis, or by enhancing the delivery of other anticancer agents to cancer cells when linked or conjugated to agents such as chemotherapeutic agents, radioactive particles or toxins. Monoclonal antibodies currently used as cancer immunotherapeutic agents include, but are not limited to, alemtuzumab (LEMTRADA®), bevacizumab (AVASTIN®), cetuximab (ERBITUX®), panitumumab (VECTIBIX®), pertuzumab (OMNITARG®, 2C4), trastuzumab (HERCEPTIN®), tositumomab (Bexxar®), abciximab (REOPRO®), adalimumab (HUMIRA®), apolizumab, aselizumab, atlizumab, bapineuzumab, basiliximab (SIMULECT®), bavituximab, belimumab (BENLYSTA®) briankinumab, canakinumab (ILARIS®), cedelizumab, certolizumab pegol (CIMZIA®), cidfusituzumab, cidtuzumab, cixutumumab, clazakizumab, crenezumab, daclizumab (ZENAPAX®), dalotuzumab, denosumab (PROLIA®, XGEVA®), eculizumab (SOLIRIS®), efalizumab, epratuzumab, erlizumab, felvizumab, fontolizumab, golimumab (SIMPONI®), ipilimumab, imgatuzumab, infliximab (REMICADE®), labetuzumab, lebrikizumab, lexatumumab, lintuzumab, lucatumumab, lulizumab pegol, lumretuzumab, mapatumumab, matuzumab, mepolizumab, mogamulizumab, motavizumab, motovizumab, muronomab, natalizumab (TYSABRI®), necitumumab (PORTRAZZA®), nimotuzumab (THERACIM®), nolovizumab, numavizumab, olokizumab, omalizumab (XOLAIR®), onartuzumab (also known as MetMAb), palivizumab (SYNAGIS®), pascolizumab, pecfusituzumab, pectuzumab, pembrolizumab (KEYTRUDA®), pexelizumab, priliximab, ralvizumab, ranibizumab, (LUCENTIS®), reslivizumab, reslizumab, resyvizumab, robatumumab, rontalizumab, rovelizumab, ruplizmnab, sarilumab, secukinumab, seribantumab, sifalimumab, sibrotuzumab, siltuximab (SYLVANT®) siplizumab, sontuzumab, tadocizumab, talizumab, tefibazumab, tocilizumab (ACTEMRA®), toralizumab, tucusituzumab, umavizmab, urtoxazumab, ustekinumab (STELARA®), vedolizumab (ENTYVIO®), visilizumab, zanolimumab, zalutumumab.

As used herein, "instructional material" includes a publication, a recording, a diagram, or any other medium of expression which can be used to communicate the usefulness of the compositions and methods of the invention. The instructional material of the kit of the invention may, for example, be affixed to a container which contains the therapeutic or diagnostic agents of the invention or be shipped together with a container which contains the therapeutic or diagnostic agents of the invention.

The term "label" when used herein refers to a detectable compound or composition. The label is typically conjugated or fused directly or indirectly to a reagent, such as a polynucleotide probe or an antibody, and facilitates detection of the reagent to which it is conjugated or fused. The label may itself be detectable (e.g., radioisotope labels or fluorescent labels) or, in the case of an enzymatic label, may catalyze chemical alteration of a substrate compound or composition which results in a detectable product.

The term "leukocytes" or "white blood cell" as used herein refers to any immune cell, including monocytes, neutrophils, eosinophils, basophils, and lymphocytes.

As used herein, the term "localize" and its grammatical equivalent mean to accumulate in, or be restricted to, a specific or limited space or area, for example a specific cell, tissue, organelle, or intracellular region such as a cellular compartment (e.g., nucleus, cytoplasm, nuclear membrane, cell membrane, etc.).

The term "lymphocytes" as used herein refers to cells of the immune system which are a type of white blood cell. Lymphocytes include, but are not limited to, T-cells (cytotoxic and helper T-cells), B-cells and natural killer cells (NK cells). The term "tumor infiltrating lymphocyte" as used herein refers to lymphocytes that are present in a solid tumor. The term "circulating lymphocyte" as used herein refers to lymphocytes that are present in the circulation (e.g., present in blood).

The terms "mesenchymal", "mesenchymal phenotype" and the like are understood in the art, and can be identified by morphological, molecular and/or functional characteristics. For example, mesenchymal cells generally have an elongated or spindle-shaped appearance, express the mesenchymal markers vimentin, fibronectin and N-cadherin, divide slowly or are non-dividing and/or have relatively high levels of motility, invasiveness and/or anchorage-independent growth as compared with epithelial cells.

As used herein, the term "mesenchymal-to-epithelial transition" (MET) is a reversible biological process that involves the transition from motile, multipolar or spindle-shaped mesenchymal cells to planar arrays of polarized cells called epithelia. MET is the reverse process of EMT. METs occur in normal development, cancer metastasis, and induced pluripotent stem cell reprogramming. In specific embodiments, MET refers to the reprogramming of cells that have undergone EMT to regain one or more epithelial characteristics (e.g., as described above). For example, such cells typically exhibit reduced motility and/or invasiveness and/or are rapidly dividing, and may thereby regain sensitivity to immunotherapeutics and/or cytotoxic agents.

The term "multiplex-PCR" refers to a single PCR reaction carried out on nucleic acid obtained from a single source (e.g., an individual) using more than one primer set for the purpose of amplifying two or more DNA sequences in a single reaction.

The terms "patient", "subject", "host" or "individual" used interchangeably herein, refer to any subject, particularly a vertebrate subject, and even more particularly a mammalian subject, for whom therapy or prophylaxis is desired. Suitable vertebrate animals that fall within the scope of the invention include, but are not restricted to, any member of the subphylum Chordata including primates (e.g., humans, monkeys and apes, and includes species of monkeys such from the genus *Macaca* (e.g., cynomologus monkeys such as *Macaca fascicularis*, and/or rhesus monkeys (*Macaca mulatta*)) and baboon (*Paolo ursinus*), as well as marmosets (species from the genus *Callithrix*), squirrel monkeys (species from the genus *Saimiri*) and tamarins (species from the genus *Saguinus*), as well as species of apes such as chimpanzees (Pan troglodytes)), rodents (e.g., mice rats, guinea pigs), lagomorphs (e.g., rabbits, hares), bovines (e.g., cattle), ovines (e.g., sheep), caprines (e.g., goats), porcines (e.g., pigs), equines (e.g., horses), canines (e.g., dogs), felines (e.g., cats), avians (e.g., chickens, turkeys, ducks, geese, companion birds such as *canaries*, budgerigars etc.), marine mammals (e.g., dolphins, whales), reptiles (snakes, frogs, lizards etc.), and fish. A preferred subject is a human in need of treatment of cancer, including through inhibiting the proliferation or viability of cancer cells and/or elicitation of an immune response (e.g., an immune response with enhanced T-cell activation) to cancer cells. However, it will be understood that the aforementioned terms do not imply that symptoms are present.

The term "pharmaceutical composition" or "pharmaceutical formulation" refers to a preparation which is in such form as to permit the biological activity of the active ingredient(s) to be effective, and which contains no additional components which are unacceptably toxic to a subject to which the composition or formulation would be administered. Such formulations are sterile. "Pharmaceutically acceptable" excipients (vehicles, additives) are those which can reasonably be administered to a subject mammal to provide an effective dose of the active ingredient employed.

As used herein, "pharmacodynamic (PD) activity" may refer to an effect of a therapy (e.g., a cytotoxic therapy or an immunotherapy) to the subject. An example of a PD activity may include modulation of the localization of at least one response to therapy biomarker and optionally expression of at least one mesenchymal and/or sternness biomarker, as described herein. Without wishing to be bound to theory, it is thought that monitoring PD activity, such as by determining localization of the at least one response to therapy biomarker and optionally expression of the at least one mesenchymal and/or sternness biomarker, may be advantageous during a clinical trial examining a therapy. Monitoring PD activity may be used, for example, to monitor response to treatment, toxicity, and the like.

The term "predictive" and grammatical forms thereof, generally refer to a biomarker or biomarker signature that provides a means of identifying, directly or indirectly, a likelihood of a patient responding to a therapy or obtaining a clinical outcome in response to therapy.

The term "prognostic" and grammatical forms thereof, generally refer to an agent or method that provides information regarding the likely progression or severity of a disease or condition in an individual. In some embodiments, prognosis also refers to the ability to demonstrate a positive or negative response to therapy or other treatment regimens, for the disease or condition in the subject. In some embodiments, prognosis refers to the ability to predict the presence or diminishment of disease/condition associated symptoms. A prognostic agent or method may comprise classifying a subject or sample obtained from a subject into one of multiple categories, wherein the categories correlate with different likelihoods that a subject will experience a particular outcome. For example, categories can be low risk and high risk, wherein subjects in the low risk category have a lower likelihood of experiencing a poor outcome (e.g., within a given time period such as 5 years or 10 years) than do subjects in the high risk category. A poor outcome could be, for example, disease progression, disease recurrence, or death attributable to the disease.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one-time administration and typical dosages range from 10 to 200 units (Grays) per day.

As used herein, a cancer patient who has been treated with a therapy is considered to "respond", have a "response", have "a positive response" or be "responsive" to the therapy if the subject shows evidence of an anti-cancer effect according to an art-accepted set of objective criteria or reasonable modification thereof, including a clinically significant benefit, such as the prevention, or reduction of severity, of symptoms, or a slowing of the progression of the cancer. It will be understood that the aforementioned terms may also be used in regard to the cancer. A variety of different objective criteria for assessing the effect of anti-cancer treatments on cancers are known in the art. The World Health Organization (WHO) criteria (Miller, A B, et al., Cancer 1981; 47(1):207-14) and modified versions thereof, the Response Evaluation Criteria in Solid Tumors (RECIST) (Therasse P, et al., *J Natl Cancer Inst* 2000; 92:205-16), and revised version thereof (Eisenhauer E A, New response evaluation criteria in solid tumors: revised RECIST guideline (version 1.1). *Eur J Cancer* 2009; 45(2):228-47) are sets of objective criteria, based on imaging measurements of the size and number of tumor lesions and detection of new lesions, e.g., from computed tomography (CT), magnetic resonance imaging (MRI), or conventional radiographs. Dimensions of selected lesions (referred to as target lesions) are used to calculate the change in tumor burden between images from different time points. The calculated response is then categorized as complete response (CR), partial response (PR), stable disease (SD), or progressive disease (PD). CR is complete disappearance of tumor (−100%), and PD is an increase of about 20%-25% or greater (depending on the particular criteria) and/or the appearance of new lesions. PR is a significant reduction (of at least about 30%) in size of tumor lesions (without emergence of new lesions) but less than a complete response. SD is in between PR and PD. (See Tables 1 and 2 for details.) These criteria are widely used as a primary endpoint in Phase II trials evaluating the efficacy of anti-cancer agents, e.g., as a surrogate for overall survival. However, anatomic imaging alone using WHO, RECIST, and RECIST 1.1 criteria were designed to detect early effects of cytotoxic agents and have certain limitations, particularly in assessing the activity of newer cancer therapies that stabilize disease. Clinical response patterns in patients treated with immunotherapeutic anti-cancer agents or molecularly targeted anti-cancer agents may extend beyond those of cytotoxic agents and can manifest after an initial increase in tumor burden or the appearance of new lesions. For example, meaningful tumor responses to immune checkpoint inhibitor may occur after a delay, in some cases following WHO- or RECIST-defined PD. Criteria designated immune-related response criteria (irRC) were defined in an attempt to capture additional favorable response patterns observed with immune therapies (Wolchok, J D, et al. (2009) Guidelines for the evaluation of immune therapy activity in solid tumors: immune-related response criteria. *Clin. Care Res.* 15, 7412-7420.). Four patterns associated with favorable survival were identified, i.e., decreased baseline lesions without new lesions; durable stable disease; initial increase in total tumor burden but eventual response; and a reduction in total tumor burden during or after the appearance of new lesion(s), of which the latter two are distinct from the response patterns considered favorable according to WHO or RECIST criteria. The irRC include criteria for complete response (irCR), partial response (irPR), stable disease (irSD), and progressive disease (irPD). Among other things, the irRC incorporates measurable new lesions into "total tumor burden" and compares this variable to baseline measurements rather than assuming that new lesions necessarily represent progressive disease. In summary, according to the immune-related response criteria, irCR is complete disappearance of all lesions whether measurable or not, and no new lesions; irPR is a decrease in tumor burden ≥50% relative to baseline; irSD is disease not meeting criteria for irCR or irPR, in absence of it progressive disease (irPD); irPD is an increase in tumor burden .gtoreq.25% relative to nadir (the minimum recorded tumor burden) (Wolchok, supra). IrCR, irPR and irPD require confirmation by a repeat, consecutive assessment at least 4 weeks from the date of first documentation. IrCR, irPR, and irSD include all patients with CR, PR, or SD by WHO criteria as well as those patients that shift to these irRC categories from WHO PD. However, some patients who would be classified as having PD according to WHO or RECIST criteria are instead classified as having PR or SD according to the irRC, identifying them as likely to have favorable survival. The irRC are applicable to immune checkpoint inhibitors and other immunotherapeutic agents. One of ordinary skill in the art will appreciate that additional response criteria are known in the art, which take into consideration various factors such as changes in the degree of tumor arterial enhancement and/or tumor density as indicators of tumor viable tissue, with decreased arterial enhancement and decreased tumor density being indicators of reduced viable tumor tissue (e.g., due to tumor necrosis). For example, modified RECIST criteria (mRECIST) take into consideration changes in the degree of tumor arterial enhancement (Lencioni R and Llovet J M. Semin Liver Dis 30: 52-60, 2010). Choi criteria and modified Choi criteria take into consideration decrease in tumor density on C T. Choi H, et al., *J Clin Oncol* 25: 1753-1759, 2007; Nathan P D, et al., *Cancer Biol Ther* 9: 15-19, 2010; Smith A D, et al., *Am J Roentgenol* 194: 157-165, 2010. Such criteria may be particularly useful in certain cancer types and/or with certain classes of therapeutic agents. For example, changes in tumor size can be minimal in tumors such as lymphomas, sarcoma, hepatomas, mesothelioma, and gastrointestinal stromal tumor despite effective treatment. CT tumor density, contrast enhancement, or MRI characteristics appear more informative than size. In certain embodiments functional imaging, e.g., using positron emission tomography (PET) may be used. For example, PET response criteria in solid tumors (PERCIST) may be used, in which the treatment response is evaluated by metabolic changes assessed with (18) F-FDG PET imaging, with decreased uptake of the tracer being indicative of (Wahl R L, et al., *J Nucl Med* 2009; 50, Suppl 1:122S-50S). It will also be understood that response criteria developed for various specific cancer types such as melanoma, breast cancer and lung cancer, are known in the art. By contrast, a cancer patient who has been treated with a therapy is considered "not to respond", "to lack a response", to have "a negative response" or be "non-responsive" to the therapy if the therapy provides no clinically significant benefit, such as the prevention, or reduction of severity, of symptoms, or increases the rate of progression of the cancer.

For purposes of the present disclosure, a cancer patient treated with an immunotherapy (e.g., an immune checkpoint inhibitor) as monotherapy or in combination with one or more other active agents (e.g., a complement inhibitor, an additional anti-cancer agent, or both) is considered to "respond", have a "response", or be "responsive" to the treatment if the patient has a complete response, partial response, or stable disease according at least to the immune-related response criteria. (The cancer patient may also respond according to RECIST, RECIST 1.1, WHO, and/or other criteria such as those mentioned above.) Likewise, the cancer in such cases is said to "respond", be "responsive", or be "sensitive" to the treatment. The cancer patient is considered to "not respond", not have a "response", or to be "nonresponsive" to the treatment if the patient has progressive disease according to the immune-related response criteria. (The cancer patient may also not respond according to RECIST, RECIST 1.1, WHO, and/or other criteria such as those mentioned above). Likewise, the cancer in such cases said to "not respond", or to be "nonresponsive", "insensitive" or "resistant" to the treatment. (A cancer is also considered to have become resistant to treatment if it initially responds but the patient subsequently exhibits progressive disease in the presence of treatment.) Thus, for example, for methods and products described herein that relate to response to treatment for cancer (e.g., methods of predicting likelihood of response, methods of classifying patients according to predicted response, methods of increasing the likelihood of response) a response is defined as irCR, irPR, or irSD, and lack of response is defined as irPD unless otherwise specified. In certain embodiments any useful response criteria may be specified. The response criteria may have been shown to correlate with a benefit such as increased overall survival or other clinically significant benefit. It will be appreciated that refinements or revisions of existing response criteria that, e.g., encompass additional favorable patterns of clinical activity (e.g., correlating with increased overall survival) applicable to immune checkpoint inhibitors or are otherwise useful may be developed in the future. In certain embodiments any such response criteria may be specified for use in methods described herein.

The term "sample" as used herein includes any biological specimen that may be extracted, untreated, treated, diluted or concentrated from a subject. A sample includes within its scope a collection of similar fluids, cells, or tissues (e.g., surgically resected tumor tissue, biopsies, including fine needle aspiration), isolated from a subject, as well as fluids, cells, or tissues present within a subject. In some embodiments the sample is a biological fluid. Biological fluids are typically liquids at physiological temperatures and may include naturally occurring fluids present in, withdrawn from, expressed or otherwise extracted from a subject or biological source. Certain biological fluids derive from particular tissues, organs or localized regions and certain other biological fluids may be more globally or systemically situated in a subject or biological source. Examples of biological fluids include blood, serum and serosal fluids, plasma, lymph, urine, saliva, cystic fluid, tear drops, feces, sputum, mucosal secretions of the secretory tissues and organs, vaginal secretions, ascites fluids such as those associated with non-solid tumors, fluids of the pleural, pericardial, peritoneal, abdominal and other body cavities, fluids collected by bronchial lavage and the like. Biological fluids may also include liquid solutions contacted with a subject or biological source, for example, cell and organ culture medium including cell or organ conditioned medium, lavage fluids and the like. The term "sample" as used herein encompasses materials removed from a subject or materials present in a subject.

A "reference sample", "reference cell", "reference tissue", "control sample", "control cell", or "control tissue", as used herein, refers to a sample, cell, tissue, standard, or level that is used for comparison purposes. In one embodiment, a reference sample, reference cell, reference tissue, control sample, control cell, or control tissue is obtained from a healthy and/or non-diseased part of the body (e.g., tissue or cells) of the same subject or individual. For example, healthy and/or non-diseased cells or tissue adjacent to the diseased cells or tissue (e.g., cells or tissue adjacent to a tumor). In another embodiment, a reference sample is obtained from an untreated tissue and/or cell of the body of the same subject or individual. In yet another embodiment, a reference sample, reference cell, reference tissue, control sample, control cell, or control tissue is obtained from a healthy and/or non-diseased part of the body (e.g., tissues or cells) of an individual who is not the subject or individual. In even another embodiment, a reference sample, reference cell, reference tissue, control sample, control cell, or control tissue is obtained from an untreated tissue and/or cell of the body of an individual who is not the subject or individual.

As used herein a "small molecule" refers to a compound that has a molecular weight of less than 3 kilodalton (kDa), and typically less than 1.5 kilodalton, and more preferably less than about 1 kilodalton. Small molecules may be nucleic acids, peptides, polypeptides, peptidomimetics, carbohydrates, lipids or other organic (carbon-containing) or inorganic molecules. As those skilled in the art will appreciate, based on the present description, extensive libraries of chemical and/or biological mixtures, often fungal, bacterial, or algal extracts, may be screened with any of the assays of the invention to identify compounds that modulate a bioactivity. A "small organic molecule" is an organic compound (or organic compound complexed with an inorganic compound (e.g., metal)) that has a molecular weight of less than 3 kilodalton, less than 1.5 kilodalton, or even less than about 1 kDa.

Various methodologies of the instant invention include a step that involves comparing a value, level, feature, characteristic, property, etc. to a "suitable control," referred to interchangeably herein as an "appropriate control," a "control sample" or a "reference." A "suitable control", "appropriate control", "control sample" or a "reference" is any control or standard familiar to one of ordinary skill in the art useful for comparison purposes. In some embodiments, a "suitable control" or "appropriate control" is a value, level, feature, characteristic, property, etc., determined in a cell, organ, or patient, e.g., a control cell, cell population, organ, or patient, exhibiting, for example, a particular biomarker profile (e.g., an epithelial cell biomarker profile, a mesenchymal cell biomarker profile, a therapy resistant cancer cell biomarker profile, a therapy sensitive cancer cell biomarker profile, a normal and/or non cancer cell biomarker profile). In other embodiments, a "suitable control" or "appropriate control" is a value, level, feature, characteristic, property, ratio, etc. (e.g., biomarker levels that correlate to a particular biomarker profile) determined prior to exposing a cancer cell or cell population comprising cancer cells to a therapy. In some embodiments, a transcription rate, mRNA level, translation rate, protein level/ratio, biological activity, cellular characteristic or property, genotype, phenotype, etc., can be determined prior to, during, or after to exposing a cancer cell or cell population comprising cancer cells to a therapy. A "suitable control" can be a pattern of levels/ratios of one or more biomarkers of the present invention that correlates to a particular biomarker profile (e.g., an epithelial cell biomarker profile, a mesenchymal cell biomarker profile, a therapy resistant cancer cell biomarker profile, a therapy sensitive cancer cell biomarker profile, a normal and/or non cancer cell biomarker profile), to which a cancer cell sample can be compared. The cancer cell sample can also be compared to a negative control. Such reference levels may also be tailored to specific techniques that are used to measure levels of biomarkers in biological samples (e.g., LC-MS, GC-MS, ELISA, PCR, etc.), where the levels of biomarkers may differ based on the specific technique that is used.

As used herein, the terms "stratifying" and "classifying" are used interchangeably herein to refer to sorting of subjects into different strata or classes based on the features of a particular physiological or pathophysiological state or condition. For example, stratifying a population of subjects according to whether they are likely to respond to a therapy (e.g., chemotherapy or immunotherapy) involves assigning the subjects based on levels of response to therapy biomarkers including PD-L1-263KMe and PD-L1-263KAc, in cancer cells optionally in combination with at least one mesenchymal and/or sternness biomarker, which suitably associates with drug resistance and/or disease burden (e.g., CD133, ALDH1A, P300, DNMT1, SETDB1 and ABCB5).

As used herein, the term "treatment" refers to clinical intervention designed to alter the natural course of the individual or cell being treated during the course of clinical pathology. Desirable effects of treatment include decreasing the rate of disease progression, ameliorating or palliating the disease state, and remission or improved prognosis. For example, an individual is successfully "treated" if one or more symptoms associated with a cancer are mitigated or eliminated, including, but are not limited to, reducing the proliferation of (or destroying) cancerous cells, reducing pathogen infection, decreasing symptoms resulting from the disease, increasing the quality of life of those suffering from the disease, decreasing the dose of other medications required to treat the disease, and/or prolonging survival of individuals. The phrase "treatment with a therapy", "treating with a therapy", "treatment with an agent", "treating with an agent" and the like refers to the administration of an effective amount of a therapy or agent, including a cancer therapy or agent, (e.g., a cytotoxic agent or an immunotherapeutic agent) to a patient, or the concurrent administration of two or more therapies or agents, including cancer therapies or agents, (e.g., two or more agents selected from cytotoxic agents and immunotherapeutic agents) in effective amounts to a patient.

As used herein, "treatment outcome" refers to predicting the response of a cancer patient to a selected therapy or treatment, including the likelihood that a patient will experience a positive or negative outcome with a particular treatment. As used herein, "indicative of a positive treatment outcome" or the like refers to an increased likelihood that the patient will experience beneficial results from the selected treatment (e.g., complete or partial response, complete or partial remission, reduced tumor size, stable disease, etc.). By contrast, "indicative of a negative treatment outcome" or the like is intended to mean an increased likelihood that the patient will not benefit from the selected treatment with respect to the progression of the underlying cancer (e.g., progressive disease, disease recurrence, increased tumor size, etc.).

"Tumor," as used herein, refers to all neoplastic cell growth and proliferation, whether malignant or benign, and all pre-cancerous and cancerous cells and tissues. The terms "cancer", "cancerous", "cell proliferative disorder", "proliferative disorder" "hyperproliferative disorder" and "tumor" are not mutually exclusive as referred to herein.

As used herein, underscoring or italicizing the name of a gene shall indicate the gene, in contrast to its protein product, which is indicated by the name of the gene in the absence of any underscoring or italicizing. For example, "PD-L1" shall mean the PD-L1 gene, whereas "PD-L1" shall indicate the protein product or products generated from transcription and translation and/or alternative splicing of the PD-L1 gene.

Each embodiment described herein is to be applied mutatis mutandis to each and every embodiment unless specifically stated otherwise.

2. Methods of Detection, Diagnosis and Prognosis

The present invention discloses that different post-translational modifications of a lysine at position 263 of the PD-L1 polypeptide sequence, which overlaps or is contained within the NLS of PD-L1, stimulate or enhance localization of PD-L1 to the nucleus or to the cytoplasm/cell membrane. A representative PD-L1 polypeptide comprises the following amino acid sequence:

MRIFAVFIFMTYWHLLNAFTVTVPKDLYVVEYG-SNMTIECKFPVEKQLDLAALIVYWEME DKNIIQFVH-GEEDLKVQHSSYRQRARLLKDQLSLG-NAALQITDVKLQDAGVYRCMISYGGADYKRITV-KVNAPY NKINQRILVVDPVTSEHELTCQAEGYP-KAEVIWTSSDHQVLSGKTTTTNSKREEKLFNVTSTL-RINTTTNEIFYCT FRRLDPEENHTAELVIPELPLAHPP-NERTHLVILGAILLCLGVALTFIFRLRKGRMMDV-KKCGIQDTNSKKQSDTH LEET [SEQ ID NO: 1], wherein the lysine at position 263 (i.e., 263K) is highlighted in bold typeface.

The present inventors have found that methylation of this lysine (i.e., PD-L1-263KMe), including trimethylation (Me3), substantially localizes PD-L1 to the cytoplasm and/or cell membrane of a cancer cell, and that acetylation of the lysine (i.e., PD-L1-263KAc) largely localizes PD-L1 to the nucleus of a cancer cell. Notably, localization of PD-L1 to the cytoplasm and/or cell membrane of the cancer cell was found to correlate with sensitivity of the cancer cell to therapy and localization of PD-L1 to the nucleus of a cancer cell was found to correlate with EMT and/or stemness of the cancer cell as well as resistance to therapy (e.g., chemotherapy and/or immunotherapy).

It has also been found that these biomarkers of PD-L1 post translational modification (PTM) (i.e., PD-L1-263KAc and PD-L1-263KMe), which are also referred to herein as "response to therapy" biomarkers) can optionally be used in combination with one or more mesenchymal and/or sternness biomarkers, which suitably associate with drug resistance and/or disease burden, such as CD133, ALDH1A, P300, DNMT1, SETDB1 and ABCB5, for monitoring response to therapy and for predicting treatment outcomes.

Thus, in accordance with the present invention, PD-L1-263KAc and PD-L1-263KMe can be employed as biomarkers for determining cellular localization of PD-L1, for predicting the likelihood of response of a cancer cell to a therapy (e.g., chemotherapy and/or immunotherapy), including likelihood of resistance or sensitivity of a cancer cell to therapy, stratifying cancer patients as likely responders or non-responders to a therapy, managing treatment of cancer patients with a therapy, and predicting treatment outcomes for cancer patients treated with a therapy.

Cancer cells for the practice of the present invention can be obtained from any suitable cancer-cell containing patient samples, illustrative examples of which include tumor biopsies, circulating tumor cells, primary cell cultures or cell lines derived from tumors or exhibiting tumor-like properties, as well as preserved tumor samples, such as formalin-fixed, paraffin-embedded tumor samples or frozen tumor samples. In some embodiments, the sample is obtained prior to treatment with a therapy. In other embodiments, the sample is obtained after treatment with a therapy. In some embodiments, the sample comprises a tissue sample, which can be formalin fixed and paraffin embedded, archival, fresh or frozen. In some embodiments, the sample is whole blood. In some embodiments, the whole blood comprises immune cells, circulating tumor cells and any combinations thereof.

Presence and/or levels/amount of a biomarker (e.g., any one or more of PD-L1-263KAc, PD-L1-263KMe and optionally PD-L1-WT, CD133, ALDH1A, P300, DNMT1, SETDB1 and ABCB5) can be determined qualitatively and/or quantitatively based on any suitable criterion known in the art, including but not limited to proteins and protein fragments. In certain embodiments, presence and/or expression levels/amount of a biomarker in a first sample is increased or elevated as compared to presence/absence and/or expression levels/amount in a second sample (e.g., before treatment with a therapy). In certain embodiments, presence/absence and/or levels/amount of a biomarker in a first sample is decreased or reduced as compared to presence and/or levels/amount in a second sample. In certain embodiments, the second sample is a reference sample, reference cell, reference tissue, control sample, control cell, or control tissue. Additional disclosures for determining presence/absence and/or levels/amount of a gene are described herein.

In some embodiments of any of the methods, an elevated level refers to an overall increase of about any of 10%, 20%, 30%, 40%, 50%, 60%, 70%, 80%, 90%, 95%, 96%, 97%, 98%, 99% or greater, in the level of biomarker (e.g., protein or nucleic acid), detected by standard art known methods such as those described herein, as compared to a reference sample, reference cell, reference tissue, control sample, control cell, or control tissue. In certain embodiments, an elevated level refers to the increase in level/amount of a biomarker in the sample wherein the increase is at least about any of 1.5×, 1.75×, 2×, 3×, 4×, 5×, 6×, 7×, 8×, 9×, 10×, 25×, 50×, 75×, or 100× the level/amount of the respective biomarker in a reference sample, reference cell, reference tissue, control sample, control cell, or control tissue. In some embodiments, an elevated level refers to an overall increase of greater than about 1.5-fold, about 1.75-fold, about-2 fold, about 2.25-fold, about 2.5-fold, about 2.75-fold, about 3.0-fold, or about 3.25-fold as compared to a reference sample, reference cell, reference tissue, control sample, control cell, control tissue, or internal control (e.g., housekeeping gene).

In some embodiments of any of the methods, a reduced level refers to an overall reduction of about any of 10%, 20%, 30%, 40%, 50%, 60%, 70%, 80%, 90%, 95%, 96%, 97%, 98%, 99% or greater, in the level of biomarker (e.g., protein or nucleic acid (e.g., gene or mRNA)), detected by standard art known methods such as those described herein, as compared to a reference sample, reference cell, reference tissue, control sample, control cell, or control tissue. In certain embodiments, reduced level refers to a decrease in level/amount of a biomarker in the sample wherein the decrease is at least about any of 0.9×, 0.8×, 0.7×, 0.6×, 0.5×, 0.4×, 0.3×, 0.2×, 0.1×, 0.05×, or 0.01× the level/amount of the respective biomarker in a reference sample, reference cell, reference tissue, control sample, control cell, or control tissue.

Presence and/or level/amount of various biomarkers in a sample can be analyzed by a number of methodologies, many of which are known in the art and understood by the skilled artisan, including, but not limited to, immunohistochemistry ("IHC"), Western blot analysis, immunoprecipitation, molecular binding assays, ELISA, ELIFA, fluorescence activated cell sorting ("FACS"), MassARRAY, proteomics, quantitative blood based assays (as for example Serum ELISA), biochemical enzymatic activity assays, in situ hybridization, Southern analysis, Northern analysis, whole genome sequencing, polymerase chain reaction ("PCR") including quantitative real time PCR ("qRT-PCR") and other amplification type detection methods, such as, for example, branched DNA, SISBA, TMA and the like), RNA-Seq, FISH, microarray analysis, gene expression profiling, and/or serial analysis of gene expression ("SAGE"), as well as any one of the wide variety of assays that can be performed by protein, gene, and/or tissue array analysis. Typical protocols for evaluating the status of genes and gene products are found, for example in Ausubel et al., eds., 1995, Current Protocols In Molecular Biology, Units 2 (Northern Blotting), 4 (Southern Blotting), 15 (Immunoblotting) and 18 (PCR Analysis). Multiplexed immunoassays such as those available from Rules Based Medicine or Meso Scale Discovery ("MSD") may also be used.

In some embodiments, presence and/or level/amount of a biomarker, particularly for non-PTM biomarkers such as the mesenchymal and/or sternness biomarkers disclosed herein, is determined using a method comprising: (a) performing gene expression profiling, PCR (such as RT-PCR or qRT-PCR), RNA-seq, microarray analysis, SAGE, MassARRAY technique, or FISH on a sample (such as a subject cancer sample); and b) determining presence and/or expression level/amount of a biomarker in the sample. In some embodiments, the microarray method comprises the use of a microarray chip having one or more nucleic acid molecules that can hybridize under stringent conditions to a nucleic acid molecule encoding a gene mentioned above or having one or more polypeptides (such as peptides or antibodies) that can bind to one or more of the proteins encoded by the genes mentioned above. In one embodiment, the PCR method is qRT-PCR. In one embodiment, the PCR method is multiplex-PCR. In some embodiments, gene expression is measured by microarray. In some embodiments, gene expression is measured by qRT-PCR. In some embodiments, expression is measured by multiplex-PCR.

Methods for the evaluation of mRNAs in cells are well known and include, for example, hybridization assays using complementary DNA probes (such as in situ hybridization using labeled riboprobes specific for the one or more genes, Northern blot and related techniques) and various nucleic acid amplification assays (such as RT-PCR using complementary primers specific for one or more of the genes, and other amplification type detection methods, such as, for example, branched DNA, SISBA, TMA and the like).

Samples from mammals can be conveniently assayed for mRNAs using Northern, dot blot or PCR analysis. In addition, such methods can include one or more steps that allow one to determine the levels of target mRNA in a biological sample (e.g., by simultaneously examining the levels a comparative control mRNA sequence of a "housekeeping" gene such as an actin family member). Optionally, the sequence of the amplified target cDNA can be determined.

Optional methods include protocols which examine or detect mRNAs, such as target mRNAs, in a tissue or cell sample by microarray technologies. Using nucleic acid microarrays, test and control mRNA samples from test and control tissue samples are reverse transcribed and labeled to generate cDNA probes. The probes are then hybridized to an array of nucleic acids immobilized on a solid support. The array is configured such that the sequence and position of each member of the array is known. For example, a selection of genes whose expression correlates with increased or reduced clinical benefit of a therapy may be arrayed on a solid support. Hybridization of a labeled probe with a particular array member indicates that the sample from which the probe was derived expresses that gene.

In preferred embodiments, presence and/or level/amount is measured by observing protein levels. In certain embodiments, the method comprises contacting the biological sample with an antibody to at least one response to therapy biomarker (e.g., PD-L1-263KAc and/or PD-L1-263KMe), optionally in combination with an antibody to at least one mesenchymal and/or sternness biomarker (e.g., CD133, ALDH1A, P300, DNMT1, SETDB1 and/or ABCB5) under conditions permissive for binding of the biomarker(s), and detecting whether a complex is formed between the antibody or antibodies and the biomarker(s). Such method may be an in vitro or in vivo method. In some embodiments, one or more anti-biomarker antibodies are used to select subjects eligible for a therapy e.g., a cytotoxic therapy or an immunotherapy.

In certain embodiments, the presence and/or expression level/amount of biomarker proteins in a sample is examined using IHC and staining protocols. IHC staining of tissue sections has been shown to be a reliable method of determining or detecting presence of proteins in a sample. In some embodiments, the level of a response to therapy biomarker (e.g., PD-L1-263KAc and/or PD-L1-263KMe) and/or mesenchymal and/or sternness biomarker in a sample from an individual is an elevated level and, in further embodiments, is determined using IHC. In one embodiment, the level of biomarker is determined using a method comprising: (a) performing IHC analysis of a sample (such as a subject cancer sample) with an antibody; and b) determining the level of a biomarker in the sample. In some embodiments, IHC staining intensity is determined relative to a reference. In some embodiments, the reference is a reference value. In some embodiments, the reference is a reference sample (e.g., control cell line staining sample or tissue sample from non-cancerous patient).

In some embodiments, expression of at least one response to therapy biomarker (e.g., PD-L1-263KAc and/or PD-L1-263KMe) and optionally at least one mesenchymal and/or sternness biomarker (e.g., CD133, ALDH1A, P300, DNMT1, SETDB1 and/or ABCB5) is evaluated on a tumor or tumor sample. As used herein, a tumor or tumor sample may encompass part or all of the tumor area occupied by tumor cells. In some embodiments, a tumor or tumor sample may further encompass tumor area occupied by tumor associated intratumoral cells and/or tumor associated stroma (e.g., contiguous peri-tumoral desmoplastic stroma). Tumor associated intratumoral cells and/or tumor associated stroma may include areas of immune infiltrates (e.g., tumor infiltrating immune cells as described herein) immediately adjacent to and/or contiguous with the main tumor mass. In some embodiments, response to therapy biomarker expression and optionally mesenchymal and/or sternness biomarker expression is evaluated on tumor cells.

In alternative methods, the sample may be contacted with an antibody specific for said biomarker under conditions sufficient for an antibody-biomarker complex to form, and then detecting said complex. The presence of the biomarker may be detected in a number of ways, such as by Western blotting and ELISA procedures for assaying a wide variety of tissues and samples, including plasma or serum. A wide range of immunoassay techniques using such an assay format are available, see, e.g., U.S. Pat. Nos. 4,016,043, 4,424,279 and 4,018,653. These include both single-site and two-site or "sandwich" assays of the non-competitive types, as well as in the traditional competitive binding assays. These assays also include direct binding of a labeled antibody to a target biomarker.

In certain embodiments, the samples are normalized for both differences in the amount of the biomarker assayed and variability in the quality of the samples used, and variability between assay runs. Such normalization may be accomplished by detecting and incorporating the expression of certain normalizing biomarkers, including expression products of well-known housekeeping genes. Alternatively, normalization can be based on the mean or median signal of all of the assayed genes or a large subset thereof (global normalization approach). On a gene-by-gene basis, measured normalized amount of a subject tumor mRNA or protein is compared to the amount found in a reference set. Normalized expression levels for each mRNA or protein per tested tumor per subject can be expressed as a percentage of the expression level measured in the reference set. The presence and/or expression level/amount measured in a particular subject sample to be analyzed will fall at some percentile within this range, which can be determined by methods well known in the art.

In some embodiments, the sample is a clinical sample. In some embodiments, the sample is obtained from a primary or metastatic tumor. Tissue biopsy is often used to obtain a representative piece of tumor tissue. Alternatively, tumor cells can be obtained indirectly in the form of tissues or fluids that are known or thought to contain the tumor cells of interest. For instance, samples of lung cancer lesions may be obtained by resection, bronchoscopy, fine needle aspiration, bronchial brushings, or from sputum, pleural fluid or blood. Genes or gene products can be detected from cancer or tumor tissue or from other body samples such as urine, sputum, serum or plasma. The same techniques discussed above for detection of target genes or gene products in cancerous samples can be applied to other body samples. Cancer cells may be sloughed off from cancer lesions and appear in such body samples. By screening such body samples, a simple early diagnosis can be achieved for these cancers. In addition, the progress of therapy can be monitored more easily by testing such body samples for target genes or gene products.

In certain embodiments, a reference sample, reference cell, reference tissue, control sample, control cell, or control tissue is a single sample or combined multiple samples from the same subject or individual that are obtained at one or more different time points than when the test sample is obtained. For example, a reference sample, reference cell, reference tissue, control sample, control cell, or control tissue is obtained at an earlier time point from the same subject or individual than when the test sample is obtained. Such reference sample, reference cell, reference tissue, control sample, control cell, or control tissue may be useful if the reference sample is obtained during initial diagnosis of cancer and the test sample is later obtained when the cancer becomes metastatic.

In certain embodiments, a reference sample, reference cell, reference tissue, control sample, control cell, or control tissue is a combination of multiple samples from one or more healthy individuals who are not the subject or individual. In certain embodiments, a reference sample, reference cell, reference tissue, control sample, control cell, or control tissue is a combination of multiple samples from one or more individuals with a disease or disorder (e.g., cancer) who are not the subject or individual. In certain embodiments, a reference sample, reference cell, reference tissue, control sample, control cell, or control tissue is pooled RNA samples from normal tissues or pooled plasma or serum samples from one or more individuals who are not the subject or individual. In certain embodiments, a reference sample, reference cell, reference tissue, control sample, control cell, or control tissue is pooled RNA samples from tumor tissues or pooled plasma or serum samples from one or more individuals with a disease or disorder (e.g., cancer) who are not the subject or individual.

In some embodiments, the sample is a tissue sample from the individual. In some embodiments, the tissue sample is a tumor tissue sample (e.g., biopsy tissue). In some embodiments, the tissue sample is lung tissue. In some embodiments, the tissue sample is renal tissue. In some embodiments, the tissue sample is skin tissue. In some embodiments, the tissue sample is pancreatic tissue. In some embodiments, the tissue sample is gastric tissue. In some embodiments, the tissue sample is bladder tissue. In some embodiments, the tissue sample is esophageal tissue. In some embodiments, the tissue sample is mesothelial tissue. In some embodiments, the tissue sample is breast tissue. In some embodiments, the tissue sample is thyroid tissue. In some embodiments, the tissue sample is colorectal tissue. In some embodiments, the tissue sample is head and neck tissue. In some embodiments, the tissue sample is osteosarcoma tissue. In some embodiments, the tissue sample is prostate tissue. In some embodiments, the tissue sample is ovarian tissue, HCC (liver), blood cells, lymph nodes, and/or bone/bone marrow tissue. In some embodiments, the tissue sample is colon tissue. In some embodiments, the tissue sample is endometrial tissue. In some embodiments, the tissue sample is brain tissue (e.g., glioblastoma, neuroblastoma, and so forth).

In some embodiments, a tumor tissue sample (the term "tumor sample" is used interchangeably herein) may encompass part or all of the tumor area occupied by tumor cells. In some embodiments, a tumor or tumor sample may further encompass tumor area occupied by tumor associated intratumoral cells and/or tumor associated stroma (e.g., contiguous peri-tumoral desmoplastic stroma). Tumor associated intratumoral cells and/or tumor associated stroma may include areas of immune infiltrates immediately adjacent to and/or contiguous with the main tumor mass.

In some embodiments, tumor cell staining is expressed as the percent of all tumor cells showing staining (e.g., membranous, cytoplasmic or nuclear staining) of any intensity. Infiltrating immune cell staining may be expressed as the percent of the total tumor area occupied by immune cells that show staining of any intensity. The total tumor area encompasses the malignant cells as well as tumor-associated stroma, including areas of immune infiltrates immediately adjacent to and contiguous with the main tumor mass. In addition, infiltrating immune cell staining may be expressed as the percent of all tumor infiltrating immune cells.

In some embodiments, the tumor is a malignant cancerous tumor (i.e., cancer).

In some embodiments, the tumor and/or cancer is a solid tumor or a non-solid or soft tissue tumor. Examples of soft tissue tumors include leukemia (e.g., chronic myelogenous leukemia, acute myelogenous leukemia, adult acute lymphoblastic leukemia, acute myelogenous leukemia, mature B-cell acute lymphoblastic leukemia, chronic lymphocytic leukemia, prolymphocytic leukemia, or hairy cell leukemia) or lymphoma (e.g., non-Hodgkin's lymphoma, cutaneous T-cell lymphoma, or Hodgkin's disease). A solid tumor includes any cancer of body tissues other than blood, bone marrow, or the lymphatic system. Solid tumors can be further divided into those of epithelial cell origin and those of non-epithelial cell origin. Examples of epithelial cell solid tumors include tumors of the gastrointestinal tract, colon, colorectal (e.g., basaloid colorectal carcinoma), breast, prostate, lung, kidney, liver, pancreas, ovary (e.g., endometrioid ovarian carcinoma), head and neck, oral cavity, stomach, duodenum, small intestine, large intestine, anus, gall bladder, labium, nasopharynx, skin, uterus, male genital organ, urinary organs (e.g., urothelium carcinoma, dysplastic urothelium carcinoma, transitional cell carcinoma), bladder, and skin. Solid tumors of non-epithelial origin include sarcomas, brain tumors, and bone tumors. In some embodiments, the cancer is non-small cell lung cancer (NSCLC). In some embodiments, the cancer is second-line or third-line locally advanced or metastatic non-small cell lung cancer. In some embodiments, the cancer is adenocarcinoma. In some embodiments, the cancer is squamous cell carcinoma. In some embodiments, the cancer is non-small cell lung cancer (NSCLC), glioblastoma, neuroblastoma, melanoma, breast carcinoma (e.g. triple-negative breast cancer), gastric cancer, colorectal cancer (CRC), or hepatocellular carcinoma. In some embodiments, the cancer is a primary tumor. In some embodiments, the cancer is a metastatic tumor at a second site derived from any of the above types of cancer.

In some embodiments, the at least one response to therapy biomarker and optionally the at least one mesenchymal and/or sternness biomarker is/are detected in the sample using a method selected from the group consisting of FACS, Western blot, ELISA, immunoprecipitation, immunohistochemistry, immunofluorescence, radioimmunoassay, dot blotting, immunodetection methods, HPLC, surface plasmon resonance, optical spectroscopy, mass spectrometry, HPLC, qPCR, RT-qPCR, multiplex qPCR or RT-qPCR, RNA-seq, microarray analysis, SAGE, MassARRAY technique, and FISH, and combinations thereof. In some embodiments, the at least one response to therapy biomarker and optionally the at least one mesenchymal and/or sternness biomarker is/are detected using FACS analysis. In some embodiments, the at least one response to therapy biomarker and optionally the at least one mesenchymal and/or sternness biomarker is detected in blood samples. In some embodiments, the at least one response to therapy biomarker and optionally the at least one mesenchymal and/or sternness biomarker is detected in circulating tumor cells in blood samples. Any suitable method to isolate/enrich such population of cells may be used including, but not limited to, cell sorting. In some embodiments, PD-L1-263KAc expression is reduced in samples from individuals that respond to treatment with a therapy, suitably an immunotherapy (e.g., one that comprises an anti-immune checkpoint molecule antibody, illustrative examples of which include an anti-PD-1 antibody and an anti-CTLA4 antibody). In some embodiments, PD-L1-263KAc expression is elevated in samples from individuals that do not respond or respond weakly to treatment with a therapy, suitably an immunotherapy (e.g., one that comprises an anti-immune checkpoint molecule antibody, illustrative examples of which include an anti-PD-1 antibody and an anti-CTLA4 antibody). In some embodiments, PD-L1-263Me expression is reduced in samples from individuals that do not respond or weakly respond to treatment with a therapy, suitably an immunotherapy (e.g., one that comprises an anti-immune checkpoint molecule antibody, illustrative examples of which include an anti-PD-1 antibody and an anti-CTLA4 antibody). In some embodiments, PD-L1-263KMe expression is elevated in samples from individuals that respond to treatment with a therapy, suitably an immunotherapy (e.g., one that comprises an anti-immune checkpoint molecule antibody, illustrative examples of which include an anti-PD-1 antibody and an anti-CTLA4 antibody).

Also provided herein are predictive/prognostic methods and kits that are based on the determination that PD-L1-263KAc co-localizes in the nucleus with a PD-L1-binding partner selected from P300, DNMT1 and SETDB1 and that this co-localization contributes at least in part to EMT of the cancer cells and resistance or non-responsiveness to therapy. The diagnostic methods suitably comprise: (i) obtaining a sample from a subject, wherein the sample comprises a cancer cell (e.g., a CTC); (ii) contacting the sample with a first antigen-binding molecule that binds to PD-L1-263KAc in the sample and a second antigen-binding molecule that binds to the PD-L1-binding partner in the sample; and (iii) detecting localization of the first and second antigen-binding molecule(s) in the nucleus of the cancer cell, wherein localization of the first and second antigen-binding molecules in the nucleus of the cancer cell is indicative that the cancer cell has increased likelihood of resistance to the therapy, that the cancer patient is a likely non-responder to the therapy, that the cancer patient is selected for not treating with the therapy, and/or that the treatment outcome for the patient is predicted to be a likely negative treatment outcome.

Localization of PD-L1-263KAc and the PD-L1-binding partner in the nucleus of a cancer cell may be performed using any suitable localization technique, e.g., by IHC, typically using an anti-PD-L1-263KAc antibody that has a different detectable moiety or label than an anti-PD-L1-binding partner antibody. In some embodiments, spatial proximity assays (also referred to as "proximity assays") are employed, which can be used to assess the formation of a complex between the PD-L1-263KAc and the PD-L1-binding partner. Proximity assays rely on the principle of "proximity probing", wherein an analyte, typically an antigen, is detected by the coincident binding of multiple (i.e., two or more, generally two, three or four) binding agents or probes, which when brought into proximity by binding to the analyte (hence "proximity probes") allow a signal to be generated.

In some embodiments, at least one of the proximity probes comprises a nucleic acid domain (or moiety) linked to the analyte-binding domain (or moiety) of the probe, and generation of the signal involves an interaction between the nucleic acid moieties and/or a further functional moiety which is carried by the other probe(s). Thus signal generation is dependent on an interaction between the probes (more particularly by the nucleic acid or other functional moieties/domains carried by them) and hence only occurs when both the necessary two (or more) probes have bound to the analyte, thereby lending improved specificity to the detection system. The concept of proximity probing has been developed in recent years and many assays based on this principle are now well known in the art.

Proximity assays are typically used to assess whether two particular proteins or portions thereof are in close proximity, e.g., proteins that are bound to each other, fusion proteins, and/or proteins that are positioned in close proximity. One such assay, known as proximity ligation assay (PLA), and which is used in some embodiments of the present invention, features two antibodies (raised in different species) bound to the targets of interest (see Nature Methods 3, 995-1000 (2006)). PLA probes, which are species-specific secondary antibodies with a unique oligonucleotide strand attached, are then bound to the appropriate primary antibodies. In the case of the targets being in close proximity, the oligonucleotide strands of the PLA probes can interact with additional ssDNA and DNA ligase such they can be circulated and amplified via rolling circle amplification (RCA). When highly processive DNA polymerases such as Phi29 DNA polymerase is used, the circular DNA template can be replicated hundreds to thousands of times longer and as a result producing ssDNA molecules from hundreds of nanometers to microns in length (see, Angewandte Chemie International Edition, 2008, 47, 6330-6337). After the amplification, the replicated DNA can be detected via detection systems. Thus, a visible signal is indicative that the targets of interest are in close proximity. These assays feature the use of several DNA-antibody conjugates as well as enzymes such as DNA ligase and DNA polymerase.

In other embodiments, a dual binders (DB) assay is employed, which utilizes a bi-specific detection agent consisting of two Fab fragments with fast off-rate kinetics joined by a flexible linker (Van dieck et al., 2014 *Chemistry & Biology* Vol. 21(3):357-368). In principle, because the dual binders comprise Fab fragments with fast off-rate kinetics, the dual binders are washed off if only one of the Fab fragments is bound to its epitope (simultaneous cooperative binding of both Fab fragments of the dual binder prevents dissociation of the dual binder and leads to positive staining/visibility).

According to another approach disclosed in International Publication WO2014/139980, which is encompassed in the practice of the present invention, proximity assays and tools are described, which employ a biotin ligase substrate and an enzyme to perform a proximity assay. The method provides detection of target molecules and proximity while maintaining the cellular context of the sample. The use of biotin ligase such as an enzyme from *E. coli* and peptide substrate such as amino-acid substrate for that enzyme provides for a sensitive and specific detection of protein-protein interactions in FFPE samples. Because biotin ligase can efficiently biotinylate appropriate peptide substrate in the presence of biotin and the reaction can only occur when the enzyme makes physical contact with the peptide substrate, biotin ligase and the substrate can be separately conjugated to two antibodies that recognize targets of interest respectively.

Also provided herein are methods for monitoring pharmacodynamic activity of a therapy (e.g., a cytotoxic therapy or an immunotherapy) by determining the compartmental location of PD-L1 and/or determining the level or amount of at least one response to therapy biomarker (e.g., PD-L1-K263Ac and/or PD-L1-K263Me) and optional at least one mesenchymal and/or sternness biomarker (e.g., CD133, ALDH1A, P300, DNMT1, SETDB1 and ABCB5) as described herein in a sample comprising cancer cells obtained from a subject, where the subject has been treated with the therapy, and determining the treatment as demonstrating pharmacodynamic activity based on the expression level of the at least one response to therapy biomarker and optionally the at least one mesenchymal and/or sternness biomarker in the sample obtained from the subject, as compared with a reference, where: (1) an unchanged level of PD-L1-K263Ac and an unchanged level of the at least one mesenchymal and/or sternness biomarker in the cancer cell relative to a suitable control (e.g., a cancer cell of the patient, which expresses PD-L1-K263Ac, before exposure to the therapy) indicates no or weak pharmacodynamic activity to the therapy, (2) an elevated level of PD-L1-K263Ac and an elevated level of the at least one mesenchymal and/or sternness biomarker in the cancer cell relative to a suitable control (e.g., a cancer cell of the patient before exposure to the therapy) indicates no or weak pharmacodynamic activity to the therapy, (3) a decreased level of PD-L1-K263Ac and a decreased level of the at least one mesenchymal and/or sternness biomarker in the cancer cell relative to a suitable control (e.g., a cancer cell of the patient before exposure to the therapy) indicates significant or strong pharmacodynamic activity to the therapy, (4) an elevated level of PD-L1-K263Me and a decreased level of the at least one mesenchymal and/or sternness biomarker in the cancer cell relative to a suitable control (e.g., a cancer cell of the patient before exposure to the therapy) indicates significant or strong pharmacodynamic activity to the therapy, and (5) a decreased level of PD-L1-K263Me and an increased level of the at least one mesenchymal and/or sternness biomarker in the cancer cell relative to a suitable control (e.g., a cancer cell of the patient before exposure to the therapy) indicates no or weak pharmacodynamic activity to the therapy. Expression level of the biomarker(s) and/or cellular composition may be measured by one or more methods as described herein.

In some embodiments, the expression level of one or more biomarker genes, proteins and/or cellular composition may be compared to a reference which may include a sample from a subject not receiving a therapy (e.g., a cytotoxic therapy or an immunotherapy). In some embodiments, a reference may include a sample from the same subject before receiving a therapy (e.g., a cytotoxic therapy or an immunotherapy). In some embodiments, a reference may include a reference value from one or more samples of other subjects receiving a therapy (e.g., a cytotoxic therapy or an immunotherapy). For example, a population of patients may be treated, and a mean, average, or median value for expression level of the at least one response to therapy biomarker and optionally the at least one mesenchymal and/or sternness biomarker may be generated from the population as a whole. A set of samples obtained from cancers having a shared characteristic (e.g., the same cancer type and/or stage, or exposure to a common therapy) may be studied from a population, such as with a clinical outcome study. This set may be used to derive a reference, e.g., a reference number, to which a subject's sample may be compared. Any of the references described herein may be used as a reference for monitoring PD activity.

Certain aspects of the present disclosure relate to measurement of the expression level of one or more biomarkers (e.g., gene expression products including mRNAs and proteins) in a sample. In some embodiments, a sample may include cancer cells. In some embodiments, the sample may be a peripheral blood sample (e.g., from a patient having a tumor). In some embodiments, the sample is a tumor sample. A tumor sample may include cancer cells, lymphocytes, leukocytes, stroma, blood vessels, connective tissue, basal lamina, and any other cell type in association with the tumor. In some embodiments, the sample is a tumor tissue sample containing tumor-infiltrating leukocytes. In some embodiments, the sample may be processed to separate or isolate one or more cell types (e.g., leukocytes). In some embodiments, the sample may be used without separating or isolating cell types.

A tumor sample may be obtained from a subject by any method known in the art, including without limitation a biopsy, endoscopy, or surgical procedure. In some embodiments, a tumor sample may be prepared by methods such as freezing, fixation (e.g., by using formalin or a similar fixative), and/or embedding in paraffin wax. In some embodiments, a tumor sample may be sectioned. In some embodiments, a fresh tumor sample (i.e., one that has not been prepared by the methods described above) may be used. In some embodiments, a tumor sample may be prepared by incubation in a solution to preserve mRNA and/or protein integrity.

In some embodiments, the sample may be a peripheral blood sample. A peripheral blood sample may include white blood cells, PBMCs, and the like. Any technique known in the art for isolating leukocytes from a peripheral blood sample may be used. For example, a blood sample may be drawn, red blood cells may be lysed, and a white blood cell pellet may be isolated and used for the sample. In another example, density gradient separation may be used to separate leukocytes (e.g., PBMCs) from red blood cells. In some embodiments, a fresh peripheral blood sample (i.e., one that has not been prepared by the methods described above) may be used. In some embodiments, a peripheral blood sample may be prepared by incubation in a solution to preserve mRNA and/or protein integrity.

In some embodiments, responsiveness to therapy may refer to any one or more of: extending survival (including overall survival and progression free survival); resulting in an objective response (including a complete response or a partial response); or improving signs or symptoms of cancer. In some embodiments, responsiveness may refer to improvement of one or more factors according to the published set of RECIST guidelines for determining the status of a tumor in a cancer patient, i.e., responding, stabilizing, or progressing. For a more detailed discussion of these guidelines, see, Eisenhauer et al. (2009 *Eur J Cancer* 45: 228-47), Topalian et al. (2012 *N Engl J Med* 366:2443-54), Wolchok et al. (2009 *Clin Can Res* 15:7412-20) and Therasse et al. (2000 *J. Natl. Cancer Inst.* 92:205-16). A responsive subject may refer to a subject whose cancer(s) show improvement, e.g., according to one or more factors based on RECIST criteria. A non-responsive subject may refer to a subject whose cancer(s) do not show improvement, e.g., according to one or more factors based on RECIST criteria.

Conventional response criteria may not be adequate to characterize the anti-tumor activity of therapeutic agents of the invention, which can produce delayed responses that may be preceded by initial apparent radiological progression, including the appearance of new lesions. Therefore, modified response criteria have been developed that account for the possible appearance of new lesions and allow radiological progression to be confirmed at a subsequent assessment. Accordingly, in some embodiments, responsiveness may refer to improvement of one or more factors according to immune-related response criteria (irRC). See, e.g., Wolchok et al. (2009, supra). In some embodiments, new lesions are added into the defined tumor burden and followed, e.g., for radiological progression at a subsequent assessment. In some embodiments, presence of non-target lesions is included in assessment of complete response and not included in assessment of radiological progression. In some embodiments, radiological progression may be determined only on the basis of measurable disease and/or may be confirmed by a consecutive assessment weeks from the date first documented.

In some embodiments, responsiveness may include immune activation. In some embodiments, responsiveness may include treatment efficacy. In some embodiments, responsiveness may include immune activation and treatment efficacy.

3. Biomarker Panels

The biomarkers of the present invention can be used in predictive and/or prognostic tests to assess, determine, and/ or qualify (used interchangeably herein) response to therapy signature status in a patient and therefore, direct treatment of the patient. The phrase "response to therapy signature status" includes a high response to therapy signature (RT high) and a low response to therapy signature (RT low). Based on this status, further procedures may be indicated, including additional tests or therapeutic procedures or regimens.

These and other biomarkers are disclosed herein, and it is understood that when combinations, subsets, interactions, groups, etc., of these biomarkers are disclosed that while specific reference of each various individual and collective combinations and permutation of these compounds may not be explicitly disclosed, each is specifically contemplated and described herein. Thus, if a panel of biomarkers A, B, and C are disclosed as well as a class of biomarkers D, E, and F and an example of a combination panel A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of using the disclosed biomarkers. Thus, if there are a variety of additional steps that can be performed, it is understood that each of these additional steps can be performed with any specific embodiment or combination of embodiments of the disclosed methods.

The response to therapy signature panel suitably includes one or more of PD-L1-K263Ac, PD-L1-K263Me, and at least one mesenchymal and/or sternness biomarker, which suitably associates with drug resistance and/or disease burden selected from CD133, ALDH1A, P300, DNMT1, SETDB1 and ABCB5. Non-limiting examples of these signature include one or both of PD-L1-K263Ac and PD-L1-K263me, and at least one mesenchymal and/or sternness biomarker selected from the following biomarker combinations: (a) CD133; (b) CD133:ALDH1A; (c) CD133:ALDH1A:P300; (d) CD133:ALDH1A:P300:DNMT1; (e) CD133:ALDH1A:P300:DNMT1:SETDB1; (f) CD133:ALDH1A:P300:DNMT1:SETDB1:ABCB5; (g) ALDH1A; (h) ALDH1A:P300; (i) ALDH1A:P300:DNMT1; (j) ALDH1A:P300:DNMT1:SETDB1; (k) ALDH1A:P300:DNMT1:SETDB1:ABCB5; (l) P300; (m) P300:DNMT1; (n) P300:DNMT1:SETDB1; (o) P300:DNMT1:SETDB1:ABCB5; (p) DNMT1; (q) DNMT1:SETDB1; (r) DNMT1:SETDB1:ABCB5; (s) SETDB1; (t) SETDB1:ABCB5; and (u) ABCB5.

The power of an assay to correctly predict response to therapy is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. An ROC curve provides the sensitivity of a test as a function of 1-specificity. The greater the area under the ROC curve, the more powerful the predictive value of the test. Other useful measures of the utility of a test are positive predictive value and negative predictive value. Positive predictive value is the percentage of people who test positive that are actually positive. Negative predictive value is the percentage of people who test negative that are actually negative.

In particular embodiments, the biomarker signatures of the present invention may show a statistical difference in different response to therapy statuses of at least $p<0.05$, $p<10^{-2}$, $p<10^{-3}$, $p<10^{-4}$ or $p<10^{-5}$. Predictive or prognostic tests that use these biomarkers may show an ROC of at least 0.6, at least about 0.7, at least about 0.8, or at least about 0.9.

In certain embodiments, the biomarkers are measured in a patient sample using the methods described herein and a response to therapy signature status is calculated. In particular embodiments, the measurement(s) may then be compared with a relevant predictive or prognostic amount(s), cut-off(s), or multivariate model scores that distinguish a high therapy response signature (RT high) status from a low therapy response signature (RT low) status. The predictive or prognostic amount(s) represents a measured amount of a biomarker(s) above which or below which a patient is classified as having a particular therapy response signature status. As is well understood in the art, by adjusting the particular predictive or prognostic cut-off(s) used in an assay, one can increase sensitivity or specificity of the assay depending on the preference of the skilled person. In particular embodiments, the particular predictive or prognostic cut-off can be determined, for example, by measuring the level or amount of biomarkers in a statistically significant number of samples from patients with different response to therapy signature statuses, and drawing the cut-off to suit the desired levels of specificity and sensitivity.

Furthermore, in certain embodiments, the values measured for biomarkers of a biomarker panel are mathematically combined and the combined value is correlated to the underlying predictive or prognostic question of high or low response to therapy signature. Biomarker values may be combined by any appropriate mathematical method known in the art. Well-known mathematical methods for correlating a biomarker combination to a disease status employ methods like discriminant analysis (DA) (e.g., linear-, quadratic-, regularized-DA), Discriminant Functional Analysis (DFA), Kernel Methods (e.g., SVM), Multidimensional Scaling (MDS), Nonparametric Methods (e.g., k-Nearest-Neighbor Classifiers), PLS (Partial Least Squares), Tree-Based Methods (e.g., Logic Regression, CART, Random Forest Methods, Boosting/Bagging Methods), Generalized Linear Models (e.g., Logistic Regression), Principal Components based Methods (e.g., SIMCA), Generalized Additive Models, Fuzzy Logic based Methods, Neural Networks and Genetic Algorithms based Methods. The skilled artisan will have no problem in selecting an appropriate method to evaluate a biomarker combination of the present invention. In one embodiment, the method used in a correlating a biomarker combination of the present invention is selected from DA (e.g., Linear-, Quadratic-, Regularized Discriminant Analysis), DFA, Kernel Methods (e.g., SVM), MDS, Nonparametric Methods (e.g., k-Nearest-Neighbor Classifiers), PLS (Partial Least Squares), Tree-Based Methods (e.g., Logic Regression, CART, Random Forest Methods, Boosting Methods), or Generalized Linear Models (e.g., Logistic Regression), and Principal Components Analysis. Details relating to these statistical methods are found in the following references: Ruczinski et al., 12 J. OF COMPUTATIONAL AND GRAPHICAL STATISTICS 475-511 (2003); Friedman, J. H., 84 J. OF THE AMERICAN STATISTICAL ASSOCIATION 165-75 (1989); Hastie, Trevor, Tibshirani, Robert, Friedman, Jerome, The Elements of Statistical Learning, Springer Series in Statistics (2001); Breiman, L., Friedman, J. H., Olshen, R. A., Stone, C. J. Classification and regression trees, California: Wadsworth (1984); Breiman, L., 45 MACHINE LEARNING 5-32 (2001); Pepe, M. S., The Statistical Evaluation of Medical Tests for Classification and Prediction, Oxford Statistical

4. Generation of Classification Algorithms for Qualifying Response to Therapy Signature Status In some embodiments, data that are generated using samples such as "known samples" can then be used to "train" a classification model. A "known sample" is a sample that has been pre-classified. The data that are used to form the classification model can be referred to as a "training data set". The training data set that is used to form the classification model may comprise raw data or pre-processed data. Once trained, the classification model can recognize patterns in data generated using unknown samples. The classification model can then be used to classify the unknown samples into classes. This can be useful, for example, in predicting whether or not a particular biological sample is associated with a certain biological condition.

Classification models can be formed using any suitable statistical classification or learning method that attempts to segregate bodies of data into classes based on objective parameters present in the data. Classification methods may be either supervised or unsupervised. Examples of supervised and unsupervised classification processes are described in Jain, "Statistical Pattern Recognition: A Review", IEEE Transactions on Pattern Analysis and Machine Intelligence, Vol. 22, No. 1, January 2000, the teachings of which are incorporated by reference.

In supervised classification, training data containing examples of known categories are presented to a learning mechanism, which learns one or more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART), artificial neural networks such as back propagation networks, discriminant analyses (e.g., Bayesian classifier or Fischer analysis), logistic classifiers, and support vector classifiers (support vector machines).

Another supervised classification method is a recursive partitioning process. Recursive partitioning processes use recursive partitioning trees to classify data derived from unknown samples. Further details about recursive partitioning processes are provided in U.S. Patent Application No. 2002 0138208 A1 to Paulse et al., "Method for analyzing mass spectra."

In other embodiments, the classification models that are created can be formed using unsupervised learning methods. Unsupervised classification attempts to learn classifications based on similarities in the training data set, without pre-classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

Learning algorithms asserted for use in classifying biological information are described, for example, in PCT International Publication No. WO 01/31580 (Barnhill et al., "Methods and devices for identifying patterns in biological systems and methods of use thereof"), U.S. Patent Application Publication No. 2002/0193950 (Gavin et al., "Method or analyzing mass spectra"), U.S. Patent Application Publication No. 2003/0004402 (Hitt et al., "Process for discriminating between biological states based on hidden patterns from biological data"), and U.S. Patent Application Publication No. 2003/0055615 (Zhang and Zhang, "Systems and methods for processing biological expression data").

The classification models can be formed on and used on any suitable digital computer. Suitable digital computers include micro, mini, or large computers using any standard or specialized operating system, such as a Unix, Windows® or Linux™ based operating system. In embodiments utilizing a mass spectrometer, the digital computer that is used may be physically separate from the mass spectrometer that is used to create the spectra of interest, or it may be coupled to the mass spectrometer.

The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including R, C, $C^{++}$, visual basic, etc.

The learning algorithms described above are useful both for developing classification algorithms for the biomarkers already discovered, and for finding new biomarker biomarkers. The classification algorithms, in turn, form the base for diagnostic tests by providing diagnostic values (e.g., cut-off points) for biomarkers used singly or in combination.

In some embodiments any of the classification methods disclosed herein may be performed at least in part by one or more computers and/or may be stored in a database on a non-transitory computer medium. In some embodiments any of the classification methods disclosed herein may be embodied or stored at least in part on a computer-readable medium having computer-executable instructions thereon. In some embodiments a computer-readable medium comprises any non-transitory and/or tangible computer-readable medium.

5. Antibodies and Cell Lines

The present invention discloses the localization, detection and quantitation of PTM biomarkers, particularly PD-L1-K263Ac and PD-L1-K263Me, using antigen-binding molecules that bind specifically to these biomarkers. Such antigen-binding molecules are typically isolated acetylation or methylation site-specific antigen-biding molecules that bind specifically to PD-L1 only when K263 is acetylated or methylated, respectively. Such antigen-binding molecules may be produced by standard antibody production methods, such as anti-peptide antibody methods, using the acetylation and methylation site sequence information provided herein, and as described for example in the examples. For example, an antibody that binds specifically to PD-L1-K263Ac or PD-L1-K263Me can be produced by immunizing an animal with a peptide antigen comprising all or part of the amino acid sequence encompassing the respective acetylated or methylated residue (e.g., a peptide antigen comprising the sequence set forth in SEQ ID NO: 3 or 4 (which encompasses the acetylated or methylated lysine (suitably, trimethyl lysine) at position 263 of PD-L1), to produce an antibody that only binds PD-L1 when acetylated or methylated at that site.

Polyclonal antibodies of the invention may be produced according to standard techniques by immunizing a suitable animal (e.g., rabbit, goat, etc.) with a peptide antigen corresponding to the protein acetylation or methylation site of interest, collecting immune serum from the animal, and separating the polyclonal antibodies from the immune serum, in accordance with standard procedures. If an antibody that only binds PD-L1 when acetylated or methylated at 263K is desired, the peptide antigen includes the acetylated or methylated form of lysine (e.g., K(Ac) or K(Me$_3$), respectively). Conversely, if an antibody that only binds PD-L1 when not acetylated or methylated at 263K is desired, the peptide antigen includes the non-acetylated form or non-methylated, conventional form of lysine.

Peptide antigens suitable for producing antibodies of the invention may be designed, constructed and employed in accordance with well-known techniques. See, e.g., ANTIBODIES: A LABORATORY MANUAL, Chapter 5, p. 75-76, Harlow & Lane Eds., Cold Spring Harbor Laboratory (1988); Czernik, Methods In Enzymology, 201: 264-283 (1991); Merrifield, J. Am. Chem. Soc. 85:21-49 (1962)).

It will be appreciated by those of skill in the art that longer or shorter acetylpeptide or methylpeptide antigens may be employed. For example, a peptide antigen may comprise an amino acid sequence set forth in SEQ ID NO: 3 or 4, or it may comprise additional amino acids flanking that sequence, or may comprise only a portion of the disclosed sequence immediately flanking the acetylatable or methylatable lysine. Typically, a desirable peptide antigen will comprise four or more amino acids flanking each side of the acetylatable or methylatable amino acid and encompassing it. Polyclonal antibodies produced as described herein may be screened as further described below.

Monoclonal antibodies of the invention may be produced in a hybridoma cell line according to the well-known technique of Kohler and Milstein. See Nature 265:495-97 (1975); Kohler and Milstein, Eur. J. Immunol. 6: 511 (1976); see also, CURRENT PROTOCOLS IN MOLECULAR BIOLOGY, Ausubel et al. Eds. (1989). Monoclonal antibodies so produced are highly specific, and improve the selectivity and specificity of diagnostic assay methods provided by the invention. For example, a solution containing the appropriate antigen may be injected into a mouse or other species and, after a sufficient time (in keeping with conventional techniques), the animal is sacrificed and spleen cells obtained. The spleen cells are then immortalized by fusing them with myeloma cells, typically in the presence of polyethylene glycol, to produce hybridoma cells. Rabbit fusion hybridomas, for example, may be produced as described in U.S. Pat. No. 5,675,063, C. Knight, Issued Oct. 7, 1997. The hybridoma cells are then grown in a suitable selection media, such as hypoxanthine-aminopterin-thymidine (HAT), and the supernatant screened for monoclonal antibodies having the desired specificity, as described below. The secreted antibody may be recovered from tissue culture supernatant by conventional methods such as precipitation, ion exchange or affinity chromatography, or the like.

Monoclonal Fab fragments may also be produced in *Escherichia coli* by recombinant techniques known to those skilled in the art. See, e.g., W. Huse, Science 246:1275-81 (1989); Mullinax et al., *Proc. Nat'l Acad. Sci.* 87: 8095 (1990). If monoclonal antibodies of one isotype are preferred for a particular application, particular isotypes can be prepared directly, by selecting from the initial fusion, or prepared secondarily, from a parental hybridoma secreting a monoclonal antibody of different isotype by using the sib selection technique to isolate class-switch variants (Steplewski, et al., *Proc. Nat'l. Acad. Sd.,* 82: 8653 (1985); Spira et al., *J. Immunol. Methods,* 74: 307 (1984)).

The preferred epitope of an acetylation-site specific antibody or methylation-site specific antibody of the invention is a peptide fragment consisting essentially of about 8 to 17 amino acids including the acetylatable or methylatable lysine, wherein about 3 to 8 amino acids are positioned on each side of the acetylatable lysine, and antibodies of the invention thus specifically bind to a post-translationally modified PD-L1 polypeptide comprising such epitopic sequence. Particularly preferred epitopes bound by the antibodies of the invention comprise all or part of an acetylatable or methylatable site sequence, including the acetylatable or methylatable amino acid.

Included within the scope of the present invention are equivalent non-antibody molecules, such as antigen-binding fragments, which bind, in a acetyl- or methyl-specific manner, to essentially the same acetylatable or methylatable epitope to which the acetyl- or methyl-specific antigen-binding molecules of the invention bind. See, e.g., Neuberger et al., *Nature* 312: 604 (1984). Such equivalent non-antibody reagents may be suitably employed in the methods of the invention further described below.

Antigen-binding molecules contemplated by the invention may be any type of antibody including immunoglobulins, including IgG, IgM, IgA, IgD, and IgE, and antigen-binding fragments thereof. The antibodies may be monoclonal or polyclonal and may be of any species of origin, including (for example) mouse, rat, rabbit, horse, or human, or may be chimeric antibodies. See, e.g., M. Walker et al., *Molec. Immunol.* 26: 403-11 (1989); Morrision et al., *Proc. Nat'l. Acad. Sci.* 81: 6851 (1984); Neuberger et al., *Nature* 312:604 (1984)). The antibodies may be recombinant monoclonal antibodies produced according to the methods disclosed in U.S. Pat. No. 4,474,893 (Reading) or U.S. Pat. No. 4,816,567 (Cabilly et al.) The antibodies may also be chemically constructed by specific antibodies made according to the method disclosed in U.S. Pat. No. 4,676,980 (Segel et al.).

The invention also provides immortalized cell lines that produce an antibody of the invention. For example, hybridoma clones, constructed as described above, that produce monoclonal antibodies to the PD-L1 acetylation or methylation sties disclosed herein are also provided. Similarly, the invention includes recombinant cells producing an antibody of the invention, which cells may be constructed by well-known techniques; for example the antigen combining site of the monoclonal antibody can be cloned by PCR and single-chain antibodies produced as phage-displayed recombinant antibodies or soluble antibodies in *E. coli* (see, e.g., ANTIBODY ENGINEERING PROTOCOLS, 1995, Humana Press, Sudhir Paul editor.)

Acetylation or methylation site-specific antibodies of the invention, whether polyclonal or monoclonal, may be screened for epitope and acetyl- or methyl-specificity according to standard techniques. See, e.g. Czemik et al., *Methods in Enzymology,* 201: 264-283 (1991). For example, the antibodies may be screened against the acetyl and non-acetyl peptide library by ELISA to ensure specificity for both the desired antigen and for reactivity only with the acetylated or methylated (or non-acetylated, non-methylated) form of the antigen. Peptide competition assays may be carried out to confirm lack of reactivity with other acetyl-epitopes on the given protein acetylation signaling protein.

The antibodies may also be tested by Western blotting against cell preparations containing the signaling protein, e.g. cell lines over-expressing the target protein, to confirm reactivity with the desired acetylated epitope/target.

Specificity against the desired acetylated or methylated epitope may also be examined by constructing mutants lacking acetylatable or methylatable residues at positions outside the desired epitope that are known to be acetylated, or by mutating the desired acetyl- or methyl epitope and confirming lack of reactivity. Acetylation- or methylation-site specific antigen-binding molecules of the invention may exhibit some limited cross-reactivity to related epitopes in non-target proteins. This is not unexpected as most antigen-binding molecules exhibit some degree of cross-reactivity, and anti-peptide antibodies will often cross-react with epitopes having high homology to the immunizing peptide. See, e.g., Czemik, supra. Cross-reactivity with non-target proteins is readily characterized by Western blotting alongside markers of known molecular weight. Amino acid sequences of cross-reacting proteins may be examined to identify sites highly homologous to the PD-L1-263K for which the antigen-binding molecules of the invention are specific.

In certain cases, polyclonal antisera may exhibit some undesirable general cross-reactivity to acetyl-lysine or methyl-lysine (suitably, trimethyl lysine) itself, which may be removed by further purification of antisera, e.g., over an acetyltyramine or methyltyramine column. Antigen-binding molecules of the invention specifically bind PD-L1 only when acetylated or only when methylated (or only when not acetylated and not methylated, as the case may be) at 263K, and do not (substantially) bind to the other form (as compared to the form for which the antigen-binding molecule is specific).

Antigen-binding molecules may be further characterized via IHC staining using normal and diseased cells or tissues to examine PD-L1 acetylation or methylation and response to therapy of diseased cells or tissue. IHC may be carried out according to well-known techniques. See, e.g., ANTIBODIES: A LABORATORY MANUAL, Chapter 10, Harlow & Lane Eds., Cold Spring Harbor Laboratory (1988). Briefly, paraffin-embedded tissue (e.g., tumor tissue) is prepared for immunohistochemical staining by deparaffinizing tissue sections with xylene followed by ethanol; hydrating in water then PBS; unmasking antigen by heating slide in sodium citrate buffer; incubating sections in hydrogen peroxide; blocking in blocking solution; incubating slide in primary antibody and secondary antibody; and finally detecting using ABC avidin/biotin method according to manufacturer's instructions.

Antigen-binding molecules may be further characterized by flow cytometry carried out according to standard methods. See Chow et al., Cytometry (Communications in Clinical Cytometry) 46: 7205-238 (2001). Briefly and by way of example, the following protocol for cytometric analysis may be employed: samples may be centrifuged on Ficoll gradients to remove erythrocytes, and cells may then be fixed with 2% paraformaldehyde for 10 minutes at 37.degree. C. followed by permeabilization in 90% methanol for 30 minutes on ice. Cells may then be stained with the primary acetylation- or methylation-site specific antigen-binding molecule of the invention (which detects PD-L1-K263Ac or PD-L1-K263Me, respectively), washed and labeled with a fluorescent-labeled secondary antibody. Additional fluorochrome-conjugated biomarker antibodies (e.g., CD133, ALDH1A, P300, DNMT1, SETDB1 and ABCB5) may also be added at this time to aid in the identification of the mesenchymal and/or sternness status of the cells. The cells may then be analyzed on a flow cytometer (e.g. a Beckman Coulter FC500) according to the specific protocols of the instrument used.

Antigen-binding molecules may be advantageously conjugated to fluorescent dyes (e.g., Alexa Fluor 488) for use in multi-parametric analyses along with anti-mesenchymal and/or sternness biomarker antibodies.

Acetylation- or methylation-site specific antigen-binding molecules of the invention specifically bind to human PD-L1 polypeptide, only when acetylated or methylated at the disclosed site (263K), but are not limited only to binding the human species, per se. The invention includes antigen-binding molecules that also bind conserved and highly homologous or identical acetylation or methylation sites in respective PTM PD-L1 proteins from other species (e.g., mouse, rat, monkey, yeast), in addition to binding the human acetylation or methylation site. Highly homologous or identical sites conserved in other species can readily be identified by standard sequence comparisons, such as using BLAST, with the human PD-L1 acetylation and methylation sites disclosed herein.

6. Kits

The present invention also extends to kits for determining expression of biomarkers, including the response to therapy and optionally mesenchymal and/or sternness biomarkers disclosed herein, which include reagents that allow detection and/or quantification of the biomarkers. Such reagents include, for example, compounds or materials, or sets of compounds or materials, which allow quantification of the biomarkers. In specific embodiments, the compounds, materials or sets of compounds or materials permit determining the expression level of a gene (e.g., a mesenchymal and/or sternness biomarker gene), including without limitation the extraction of RNA material, the determination of the level of a corresponding RNA, etc., primers for the synthesis of a corresponding cDNA, primers for amplification of DNA, and/or probes capable of specifically hybridizing with the RNAs (or the corresponding cDNAs) encoded by the genes, TaqMan probes, proximity assay probes, ligases, antibodies etc.

The kits may also optionally include appropriate reagents for detection of labels, positive and negative controls, washing solutions, blotting membranes, microtiter plates, dilution buffers and the like. For example, a nucleic acid-based detection kit may include (i) a mesenchymal and/or sternness biomarker polynucleotide (which may be used as a positive control), (ii) a primer or probe that specifically hybridizes to a mesenchymal and/or sternness biomarker polynucleotide. Also included may be enzymes suitable for amplifying nucleic acids including various polymerases (reverse transcriptase, Taq, Sequenase™, DNA ligase etc. depending on the nucleic acid amplification technique employed), deoxynucleotides and buffers to provide the necessary reaction mixture for amplification. Such kits also generally will comprise, in suitable means, distinct containers for each individual reagent and enzyme as well as for each primer or probe. Alternatively, a protein-based detection kit may include (i) at least one PD-L1 polypeptide, which is suitably selected from PD-L1-K263Ac, PD-L1-K263Me, a fragment of PD-L1-K263Ac comprising K263Ac or a fragment of PD-L1-K263me comprising K263Me, and a PD-L1 polypeptide that is not acetylated or methylated (which may be used as a positive control), (ii) one or more antigen-binding molecules that bind specifically to a PD-L1 polypeptide, which is suitably selected from PD-L1-K263Ac, PD-L1-K263Me, and a PD-L1 polypeptide that is not acetylated or methylated, (iii) at least one mesenchymal and/or stemness biomarker polypeptide selected from CD133, ALDH1A, P300, DNMT1, SETDB1 and ABCB5 or fragments thereof; and/or (iv) one or more antigen-binding molecules that bind specifically to a mesenchymal and/or stemness biomarker polypeptide selected from CD133, ALDH1A, P300, DNMT1, SETDB1 and ABCB5. The antigen-binding molecules are suitably detectably labeled. The kit can also feature various devices (e.g., one or more) and reagents (e.g., one or more) for performing one of the assays described herein; and/or printed instructional material for using the kit to quantify the expression of a T-cell function biomarker gene. The reagents described herein, which may be optionally associated with detectable labels, can be presented in the format of a microfluidics card, a chip or chamber, a microarray or a kit adapted for use with the assays described in the examples or below, e.g., RT-PCR or Q PCR techniques described herein.

Materials suitable for packing the components of the diagnostic kits may include crystal, plastic (polyethylene, polypropylene, polycarbonate and the like), bottles, vials, paper, envelopes and the like. Additionally, the kits of the invention can contain instructional material for the simultaneous, sequential or separate use of the different components contained in the kit. The instructional material can be in the form of printed material or in the form of an electronic support capable of storing instructions such that they can be read by a subject, such as electronic storage media (magnetic disks, tapes and the like), optical media (CD-ROM, DVD) and the like. Alternatively or in addition, the media can contain Internet addresses that provide the instructional material.

7. Patient Classification and Treatment Management

The present invention extends to methods of selecting or identifying individuals who are appropriate candidates for treatment with a therapy (e.g., a cytotoxic therapy, an immunotherapy, etc.) for treatment of cancer. Such individuals include patients that are predicted to be responsive to the therapy and thus have an increased likelihood of benefiting from administration of the therapy relative to other patients having different characteristic(s) (e.g., non-responsiveness to the therapy). In certain embodiments an appropriate candidate is one who is reasonably likely to benefit from treatment or at least sufficiently likely to benefit as to justify administering the treatment in view of its risks and side effects. The invention also encompasses methods of selecting or identifying individuals who are not appropriate candidates for treatment with a therapy (e.g., a cytotoxic therapy, an immunotherapy, etc.) for treatment of cancer. Such individuals include patients that are predicted to be non-responsive or weakly responsive to the therapy and thus have a decreased likelihood of benefiting from administration of the therapy relative to other patients having different characteristic(s) (e.g., responsiveness to the therapy), or a low or substantially no likelihood of benefiting from such treatment, such that it may be desirable to use a different or additional treatment. In some embodiments, whether a subject is an appropriate candidate for therapy with a therapy is determined based on an assay of at least one response to therapy biomarker and optionally at least one mesenchymal and/or stemness biomarker in the subject or in a sample obtained from the subject.

In some aspects described herein are methods of determining, for example based on an assay of at least one response to therapy biomarker and optionally at least one mesenchymal and/or stemness biomarker, the likelihood that a subject in need of treatment for cancer will respond to treatment with a therapy (e.g., a cytotoxic therapy, an immunotherapy, etc.) and/or of identifying and/or selecting a subject to receive such treatment. In specific embodiments, the therapy is an immunotherapy, suitably with an anti-immune checkpoint inhibitor. The phrase "treatment with an immune checkpoint inhibitor", also referred to as "immune checkpoint inhibitor treatment", "therapy with an immune checkpoint inhibitor", or "immune checkpoint inhibitor therapy", encompasses embodiments pertaining to treatment with a single immune checkpoint inhibitor and embodiments pertaining to treatment with two or more immune checkpoint inhibitors in combination. In some embodiments immune checkpoint inhibitor treatment comprises inhibiting two or more different immune checkpoint pathways using a single agent or using two or more separate agents.

In order that the invention may be readily understood and put into practical effect, particular preferred embodiments will now be described by way of the following non-limiting examples.

EXAMPLES

Example 1

Nuclear PD-L1 Localizes with Key Active Histone Marks

Using a commercially available antibody for PD-L1, the present inventors determined that nuclear PD-L1 is prevalent in mesenchymal CTCs isolated from metastatic colorectal cancer, metastatic prostate cancer and metastatic breast cancer patient samples and in drug-resistant cancer cells (i.e., chemotherapeutic and immunotherapeutic drugs) as well as in several breast cancer cell lines, as shown in FIG. 1A, B. They also investigated whether nuclear PD-L1 associates with chromatin and found that it strongly co-localized with active marks H3k27ac and H3k4me3 but not repressive mark H3k9me3 (FIG. 1C).

Next, the present inventors studied whether post-translational modification (PTM) played a role in localizing PD-L1 into the nucleus (also referred to herein as nuclear PD-L1) and in particular, examined PD-L1 for acetylation/methylation motifs. This analysis revealed the presence of a significant high score acetylation/methylation motif at residue lysine-263 (K263), which contained a canonical nuclear localization sequence (NLS).

Based on this analysis, individual plasmids were designed for expression of LSD1 with a wild-type (WT) version of the NLS region, and two mutant forms of the NLS: Mut1, comprising an acetylation mimic in which glutamine is substituted for lysine (K263Q); and Mutt, comprising a residue that is unable to be acetylated or methylated, in which arginine is substituted for lysine (K263R). Of interest, the Mut1-expressing plasmid biased localization of PD-L1 to the nucleus over that of the WT PD-L1-expressing plasmid (FIG. 2A).

Example 2

Nuclear PD-L1 Drives Mesenchymal, Stemness Marker Expression

Figure 2:
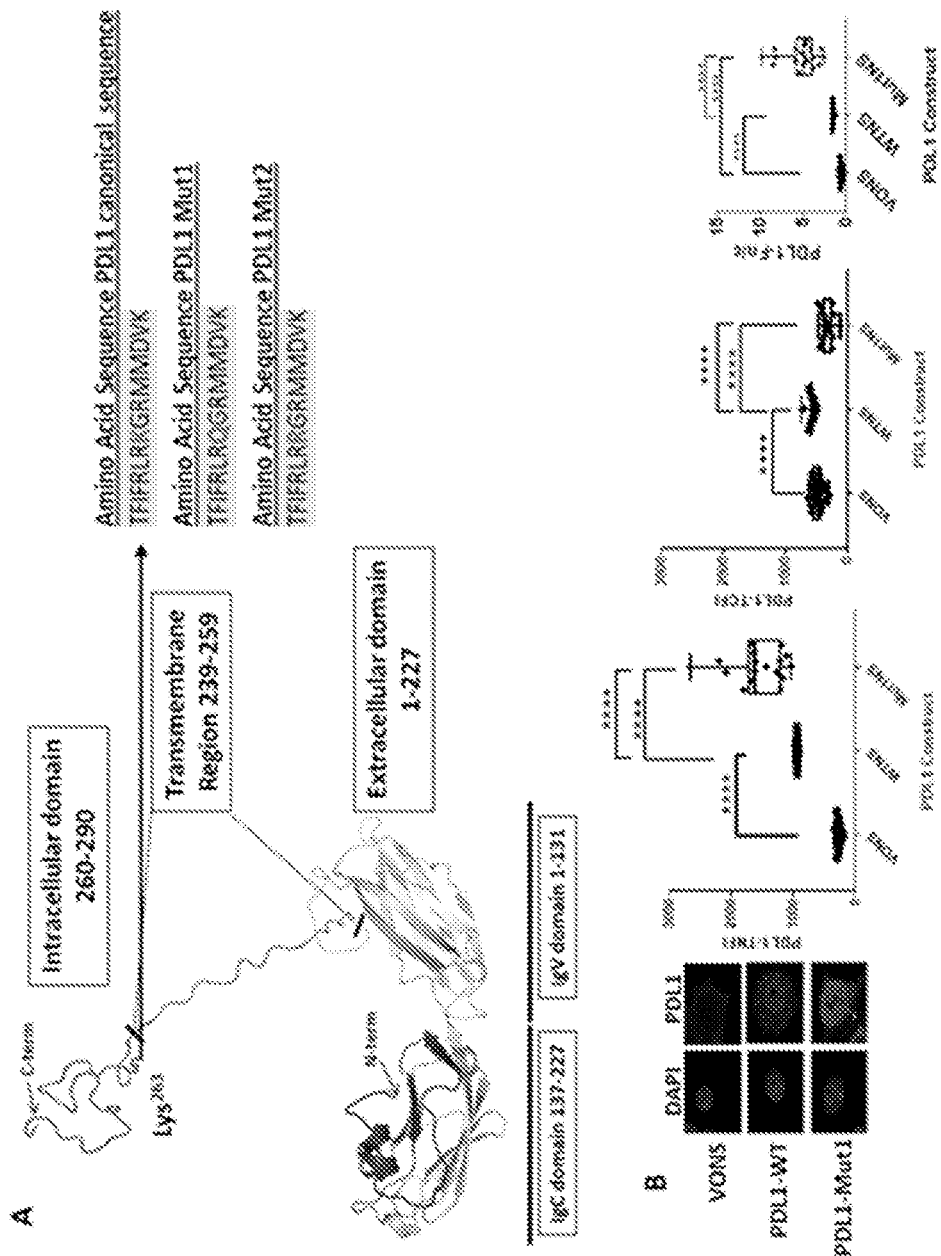
FIG. 2 is a schematic, photographic and graphical representation showing wild-type and mutant versions of a predicted acetylation/methylation motif of PD-L1 and their effect on localization of PD-L1 in epithelial cancer cells. (A) 3D schematic of PD-L1 showing the PD-L1 wild-type sequence and a significant, conserved motif for methylation and acetylation surrounding the target residue K263. This region is part of a flexible C-terminal region that overlaps with or is contained in a putative NLS domain. Three PD-L1 plasmids were constructed: one with the wild-type canonical sequence and 2 mutants, mutant 1 (Mut1), which has a lysine to glutamine substitution at position 263, and which was designed to mimic an acetylated form of PD-L1, and mutant 2 (Mut2), which has a lysine to arginine substitution at the same position, and which was designed to mimic a non-acetylated form of PD-L1. These plasmids were designed to test the importance of this predicted acetylation/methylation motif on nuclear localization of PD-L1. (B) Analysis of PD-L1 localization in MCF7 epithelial breast cancer cell line transfected with the plasmid constructs. Immunofluorescence microscopy was performed on cells that were fixed and probed with primary antibodies to PD-L1. Graphs represent the TNFI, TCFI and nuclear/cytoplasmic fluorescence ratio (Fn/c) of PD-L1 in transfected cells measured using ImageJ to select the nucleus minus background (n>20 cells/sample).

Transfection of WT-PD-L1—and Mut1-PDL1-expressing plasmids into the MCF7 breast cancer cell line increased drug-resistance, sternness, mesenchymal and aggressive cancer signatures and pushed the epithelial line to a more basal, triple negative phenotype (MDA-MB-231) with decreased proliferation (FIG. 2B). Drug resistant cancer stem cells have a decreased, almost dormant cell cycle which is present in multiple resistant cancer types (Ebinger et al., 2016, Cancer Cell 30, 849-862). This demonstrates the importance of PD-L1 in regulating a dormant, therapy resistant phenotype in sternness, mesenchymal tumor cells.

Figure 3:
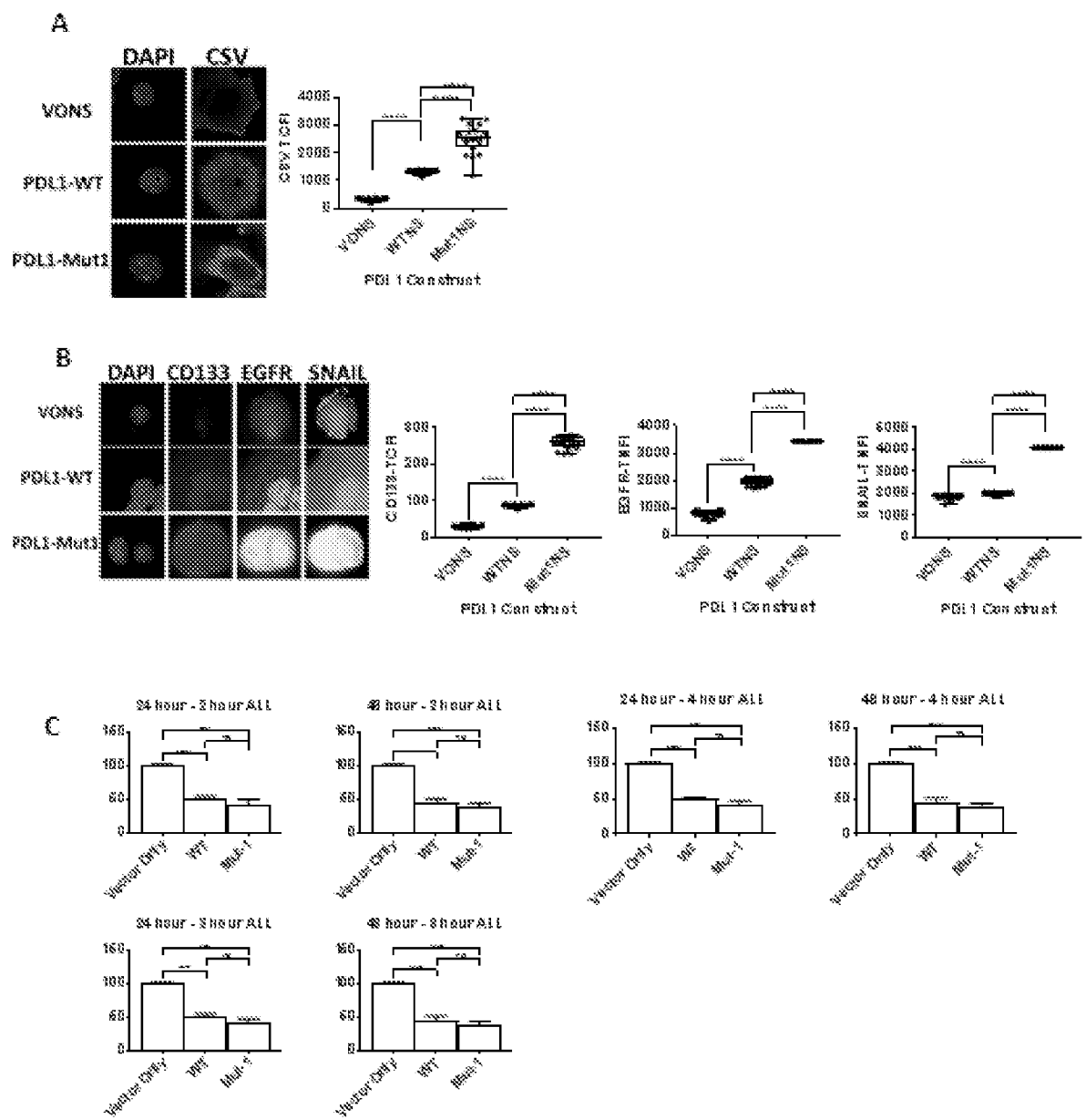
FIG. 3 is a photographic and graphical representation showing that Mut1 leads to increased expression of mesenchymal, chemo-resistance and/or stemness biomarkers. (A) Analysis of CSV (EMT biomarker) expression in MCF7 epithelial breast cancer cell line transfected with plasmid constructs shown in FIG. 2. Cells were fixed and immunofluorescence microscopy was performed on these and probed with primary antibodies to CSV. Graph represents the TCFI in transfected cells measured using ImageJ to select the nucleus minus background (n>20 cells/sample). (B) Analysis of CD133, EGFR and SNAIL (Sternness and/or mesenchymal biomarkers) expression in MCF7 epithelial breast cancer cell line transfected with the same constructs. Cells were fixed and immunofluorescence microscopy was performed on these and probed with primary antibodies to CD133, EGFR and SNAIL. Graphs represent the TCFI or TNFI in transfected cells measured using ImageJ to select the nucleus minus background (n>2 0 cells/sample). (C) WTS-1 proliferation assay was used to examine the effect of transfection of MCF7 epithelial breast cancer cell line with plasmid constructs shown in FIG. 2, on cell proliferation at 24 hr and 48 hr post incubation with WST-1 for 2, 3 and 4 hr, respectively.
Figure 4:
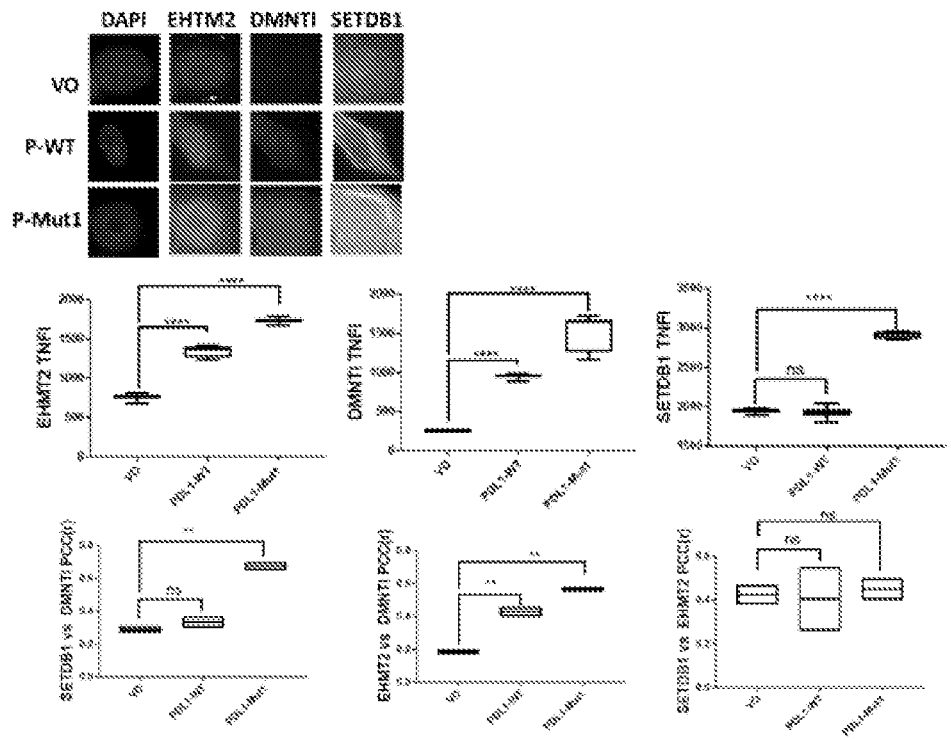
FIG. 4 is a photographic and graphical representation showing that the acetylated form of PD-L1 (nuclear PD-L1) co-localizes with epigenetic enzymes SETDB1 and DMNT1 in the nucleus. (A) Analysis of EHTM2, DMNT1 and SETDB1 (epigenetic enzymes) expression in MCF7 epithelial breast cancer cell line transfected with plasmid constructs shown in FIG. 2. Cells were fixed and immunofluorescence microscopy was performed on these and probed with primary antibodies to EHTM2, DMNT1 and SETDB1. Graphs represent the TCFI or TNFI in transfected cells measured using ImageJ to select the nucleus minus background (n>20 cells/sample). ImageJ software with automatic thresholding and manual selection of regions of interest (ROIs) specific for cell nuclei was used to calculate the PCC for each pair of antibodies in order to quantify co-localization of PD-L1 and the epigenetic enzymes. (B) Analysis of EHTM2, DMNT1 and SETDB1 (epigenetic enzymes) expression in a 4T1 metastatic mouse cancer model (Group A=Control, Group B=Abraxane treated). Cells were fixed and immunofluorescence microscopy was performed on these and probed with primary antibodies to EHTM2, DMNT1 and SETDB1. Graphs represent the TCFI or TNFI in transfected cells measured using ImageJ to select the nucleus minus background (n>20 cells/sample). ImageJ software with automatic thresholding and manual selection of regions of interest (ROIs) specific for cell nuclei was used to calculate the PCC for each pair of antibodies.
Figure 4:
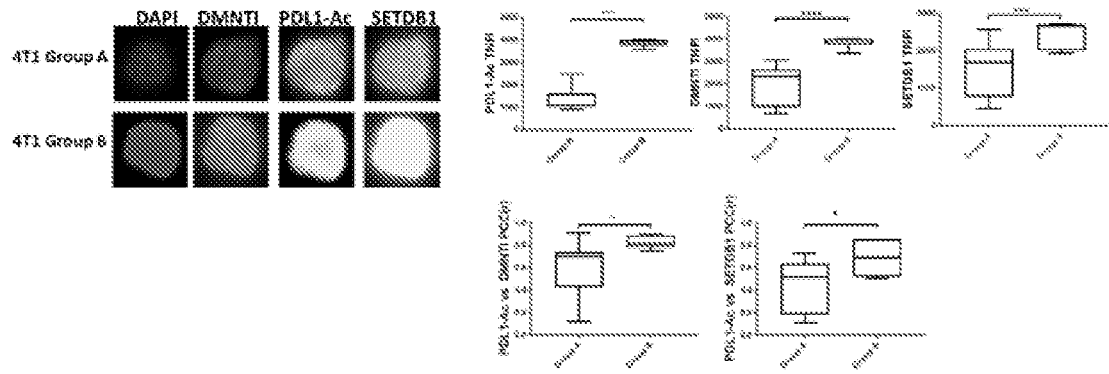
Figure 5:
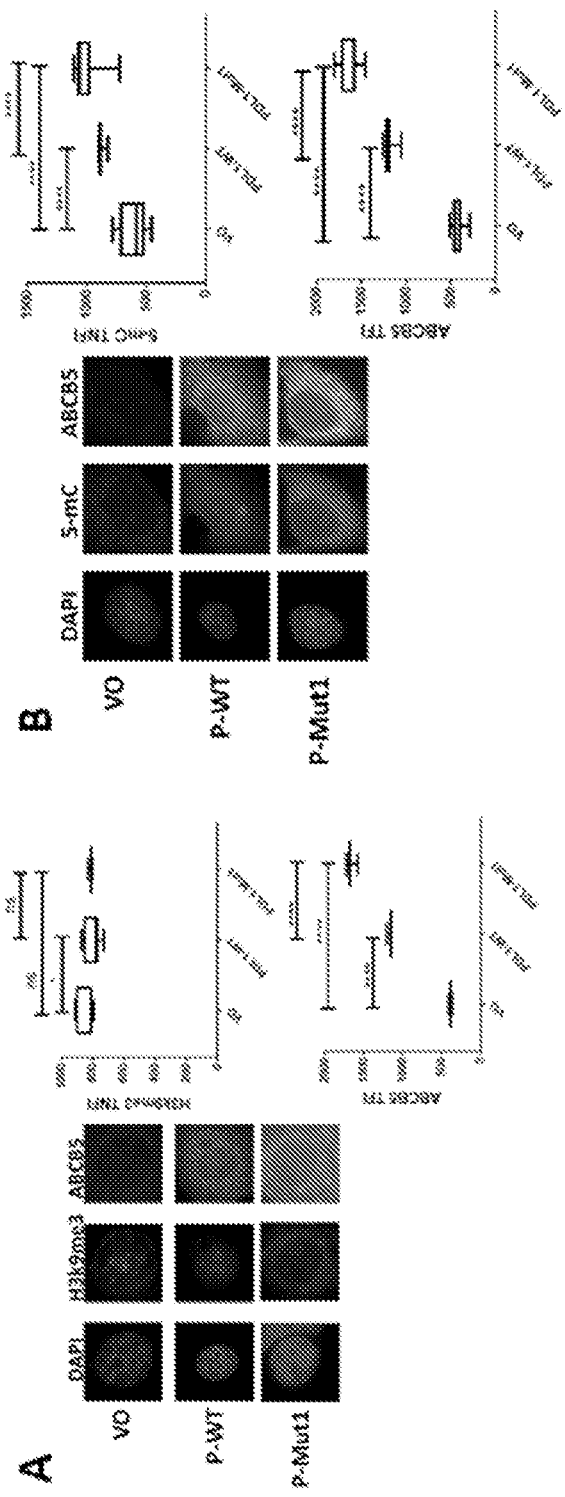
FIG. 5 is a photographic and graphical representation showing that nuclear PD-L1 increases DNA methylation (5-mC) and drug resistance biomarker ABCB5 in epithelial breast cancer cells. (A) The MCF7 epithelial breast cancer cell line was transfected with plasmid constructs shown in FIG. 2. Cells were fixed and immunofluorescence microscopy was performed on these and probed with primary antibodies to H3k9me3 and ABCB5. Graphs represent the TFI or TNFI in transfected cells measured using ImageJ to select the nucleus minus background (n>20 cells/sample). (B) The MCF7 epithelial breast cancer cell line was transfected with plasmid constructs shown in FIG. 2. Cells were fixed and immunofluorescence microscopy was performed on these and probed with primary antibodies to 5-mC and ABCB5. Graphs represent the TFI or TNFI in transfected cells measured using ImageJ to select the nucleus minus background (n>20 cells/sample).

Since increased expression of mesenchymal markers (such as CSV, EGFR, SNAIL and ABCB5) are hall-marks of a mesenchymal, drug-resistant, stem like-signature (Wang et al., 2016, Genes & Diseases (2016) 3, 3e6; van der Toom et al., 2016, Oncotarget. 7(38): 62754-62766), the expression of these markers was examined in the inventors' PD-L1 plasmid transfection model. This study revealed that expression of the Mut1 construct, which restricts localization of PD-L1 to the nucleus, significantly increases expression of each of CSV, CD133, EGFR and SNAIL (FIG. 3A, 3B). It was also found that expression of nuclear PD-L1 increased expression of epigenetic enzymes such as the methyl transferases SETDB1, EHTM2 and DNMT1 (FIGS. 4A and 4B). Given the effect of nuclear PD-L1 on SETDB1 and DNMT1 expression, it was decided to examine the effect on the read out of the enzymes for SETDB1, the histone PTM H3k9me3 and DNA-methylation in general (5-mC). Surprisingly, it was found that nuclear PD-L1 in the MCF7 cell line, had minimal to no effect on H3k9me3 expression suggesting a protein-protein interaction role for SETDB1. By contrast, 5-mC and resistance marker ABCB5 were both dramatically increased suggesting that nuclear PDL1 can regulate these epigenetic enzymes in aggressive cancer and therefore play a role in DNA methylation (FIG. 5).

Example 3

Anti-PD-L1 Antibodies Target the Critical Lysine-NLS Motif

Figure 6:
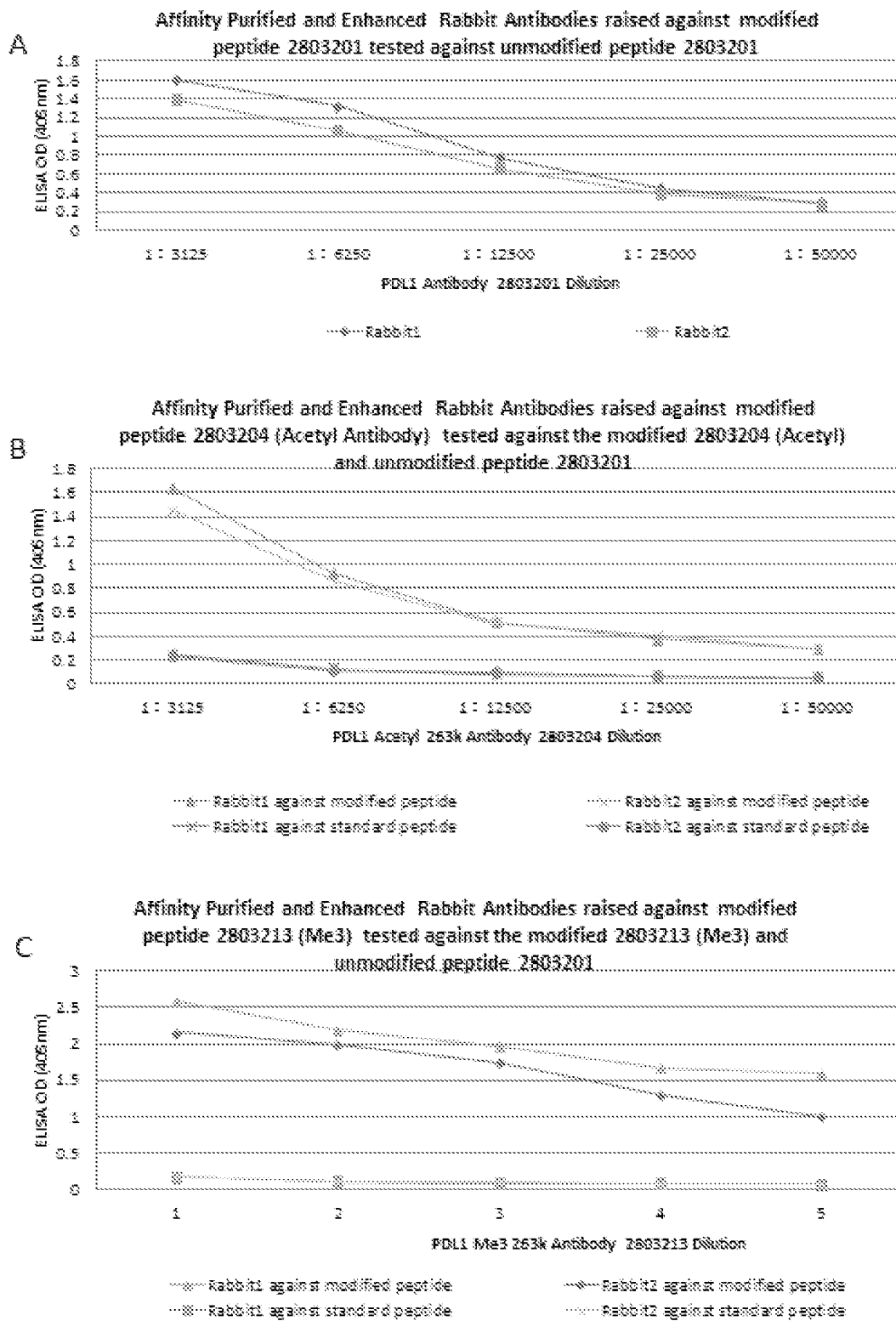
FIG. 6 is a graphical representation showing ELISA analysis of rabbit polyclonal antibody specificity to PD-L1-K263Ac or PD-L1-K263Me. (A) PD-L1 with unmodified K263, (B) PD-L1 with acetyl at K263 (B) and (C) PD-L1 with methyl (particularly trimethyl, Me3) at K263.

Next custom antibodies were designed and raised against the NLS motif comprising unmodified, tri-methylated (me3) or acetylated forms of K263 to test the nuclear targeting role of acetylation and methylation. FIG. 6 depicts ELISA affinity binding assays indicating that the custom antibodies are specific for the corresponding antibody target, i.e., unmodified (FIG. 6A), acetylated (FIG. 66) or methylated K263 (FIG. 6C).

Figure 7:
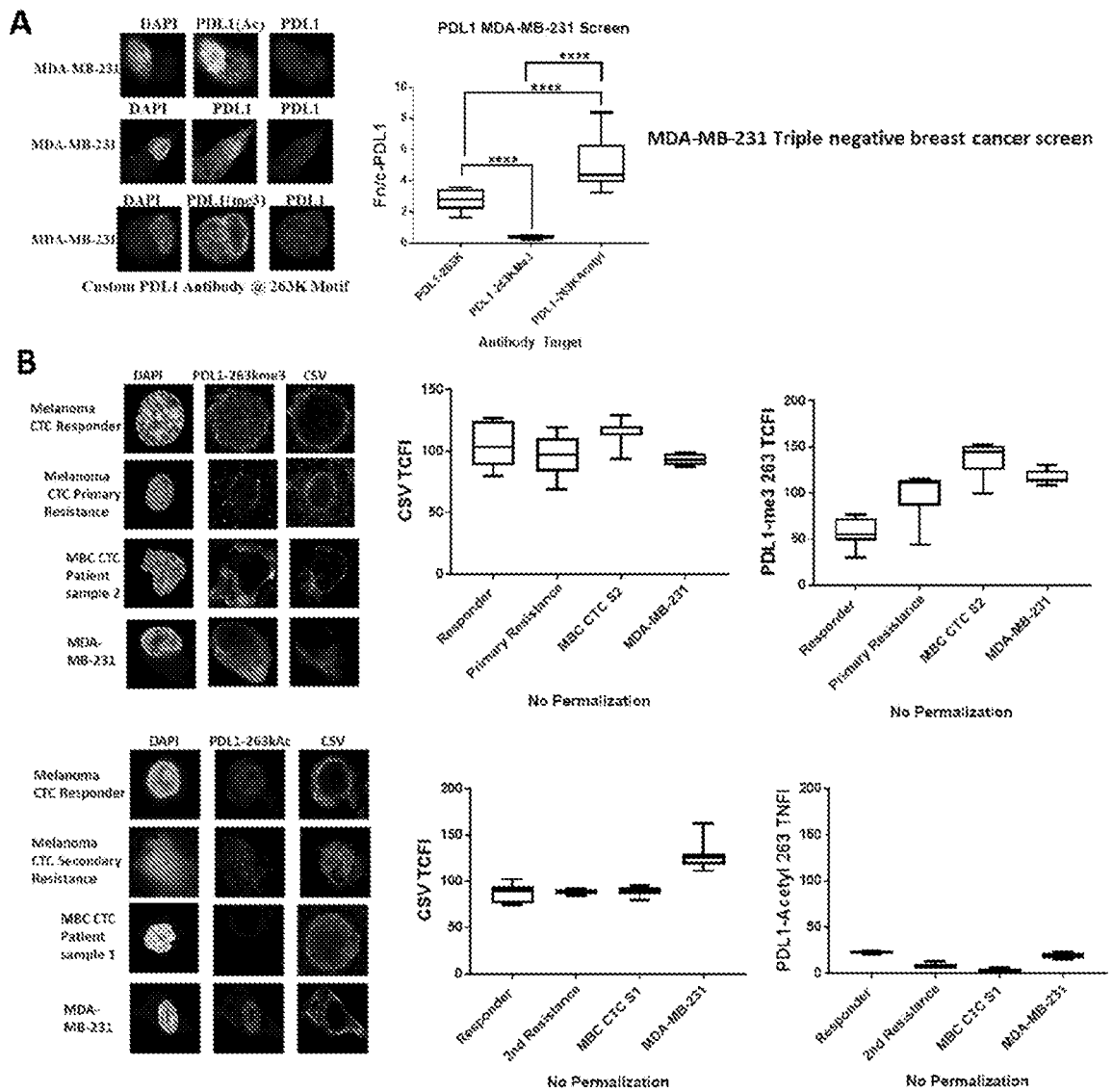
FIG. 7 is a photographic and graphical representation showing that PD-L1-K263-Ac (PDL1Ac) is retained in and restricted to the nucleus whereas PD-L1-K263-Me (PDL1Me3) is restricted to the cytoplasm/cell membrane in MDA-MB-231 cells. (A) Fixed MDA-MB-231s cells were permeabilized and immunofluorescence microscopy was performed on these cells probed with rabbit anti-PD-L1-WT, rabbit anti-PD-L1-K263-Ac, rabbit anti-PD-L1-K263-Me and a commercial PD-L1 antibody as a control. Graph represents the Fn/c using the equation: Fn/c=(Fn−Fb)/(Fc−Fb), where Fn is nuclear fluorescence, Fc is cytoplasmic fluorescence, and Fb is background fluorescence using ImageJ to select the nucleus minus background (n=>20 cells/sample. (B) Fixed MDA-MB-231s cells, melanoma CTCs (from responders to immunotherapy and non-responders to immunotherapy) were not permeabilized and immunofluorescence microscopy was performed on these cells probed with rabbit anti-PD-L1-WT, rabbit anti-PD-L1-K263-Ac, rabbit anti-PD-L1-K263-Me and an anti-CSV antibody. Graph represents the TCFI or TNFI using ImageJ to select the nucleus minus background (n>20 cells/sample).

This study revealed that acetylated PD-L1 at 263K is retained in and restricted to the nucleus whereas methylated PD-L1 at 263k is restricted to the cytoplasm/cell surface in MDA-MB-231 cells (FIG. 7A). The inventors also examined the expression of the acetylation targeted antibody and the me3 targeted antibody in both melanoma samples and metastatic breast cancer (MBC) samples that had not been permeabilized. They found that while the PD-L1-K263me3 antibody was able to label the cytoplasm of the cells successfully, the PD-L1-K263Ac antibody was not, indicating the nuclear preference for this PTM of PD-L1 (FIG. 7B).

Figure 8:
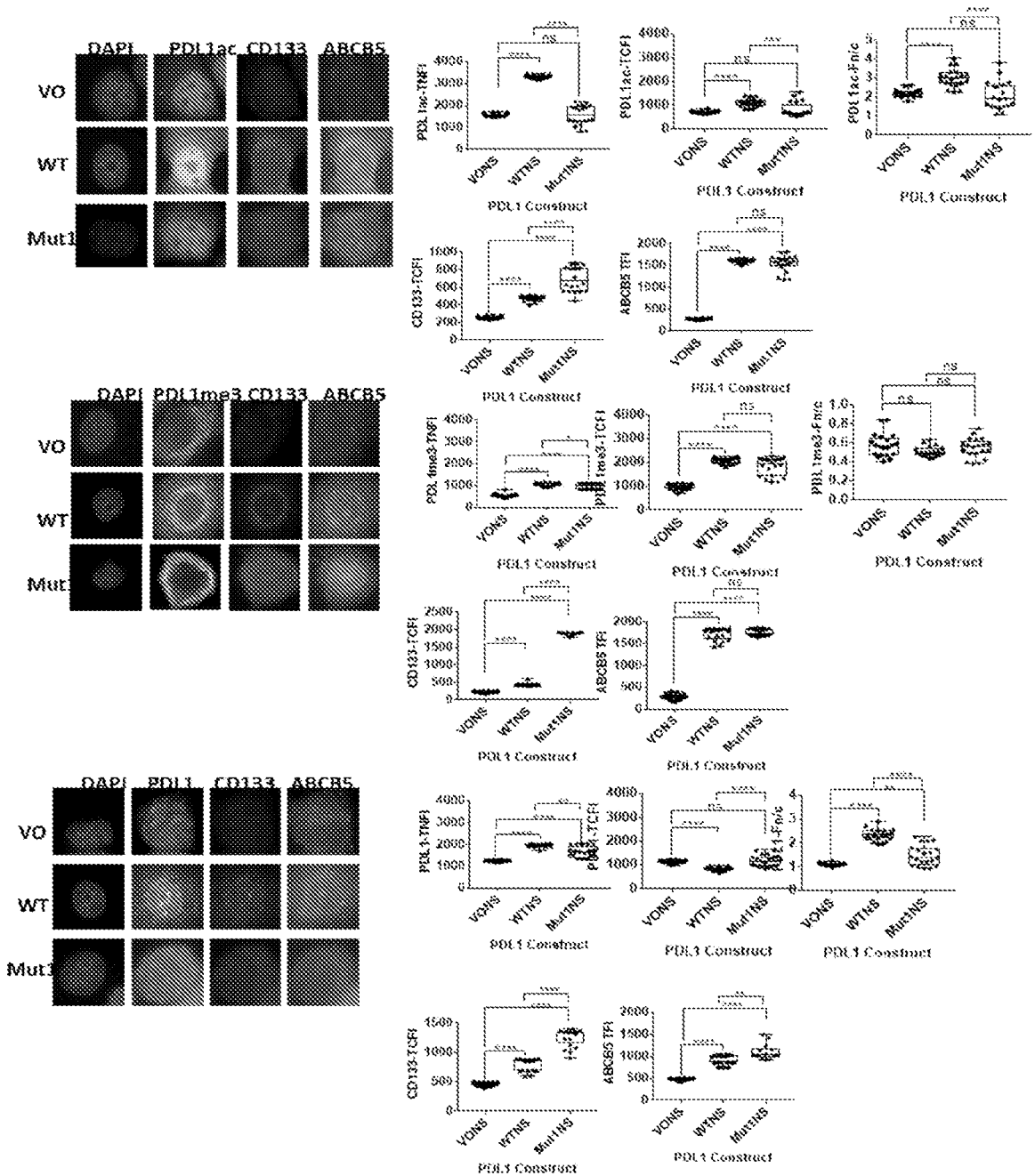
FIG. 8 is a photographic and graphical representation showing analysis of sternness and drug resistance biomarkers (CD133, ABCB5) in MCF7 epithelial breast cancer cell line transfected with the plasmid constructs shown in FIG. 2 and co-labelled with rabbit anti-PD-L1-WT, rabbit anti-PD-L1-K263-Ac, rabbit anti-PD-L1-K263-Me. The cells were fixed and Immunofluorescence microscopy was performed on these and probed with primary antibodies to CD133, ABCB5, PD-L1-WT, PD-L1-K263-Ac and PD-L1-K263-Me. Graphs represents the TCFI in transfected cells measured using ImageJ to select the nucleus minus background (n>20 cells/sample).

The specificity of these antibodies was also confirmed against the WT and Mutt plasmid constructs, as shown in FIG. 8.

Example 4

PD-L1 K263Ac is Increased in Higher Disease Burden

A panel of antibodies specific for a drug-resistant, sternness (DRS) signature (i.e., anti-CD133, anti-PDL1-K263Ac and anti-ABCB5) was used to explore whether they could be used to stratify different melanoma patients according to whether they had complete responses (CR) or partial responses (PR) to therapy and whether they had stable disease (SD) or progressive disease (PR). This study revealed that increased expression of nuclear PDL1-K263Ac correlated with increased disease burden, and that the PD cohort showed the highest expression of PD-L1-K263Ac (FIG. 9A).

Figure 9:
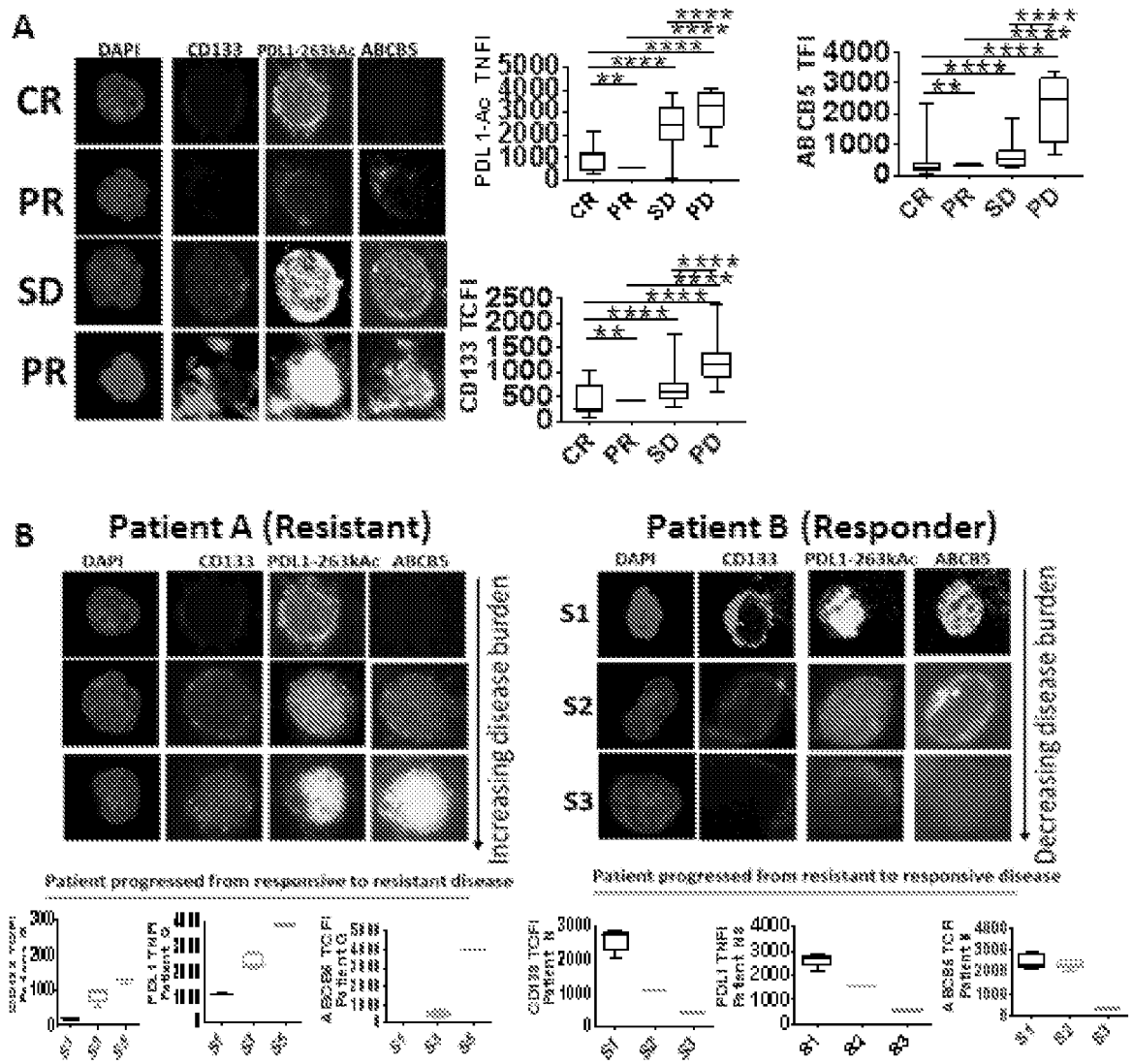
FIG. 9 is a photographic and graphical representation showing that PD-L1 K263-Ac is increased in higher disease burden. (A) CTCs isolated from melanoma bloods from complete response (CR), partial response (PR), stable disease (SD) or progressive disease (PD) as per RECIST 1.1 were screened with antibodies specific for PD-L1 K263-Ac and for mesenchymal/drug resistant biomarkers CD133 and ABCB5. Cells were fixed and immunofluorescence microscopy was performed, probing with primary antibodies to CD133, PD-L1 K263-Ac and ABCB5, and with DAPI, which is a fluorescent stain that binds strongly to A-T rich regions in DNA. Representative images for each dataset are shown. Graphs represent the TCFI values for CD133, TNFI for PDL1 and TFI for ABCB5 measured using ImageJ minus background (n=5 patients per a group). (B) CTCs isolated from two patients: Patient A (Resistant to immunotherapy) and Patient B (responder to immunotherapy) were tracked over multiple time points (1 sample every 3 months) with the same panel of antibodies as described in (A). Cells were fixed and immunofluorescence microscopy was performed probing with primary antibodies to CD133, PD-L1-K263-Ac (T53p) and ABCB5, and with DAPI. Representative images for each dataset are shown. Graphs represent the TCFI values for CD133, TNFI for PDL1 and TFI for ABCB5 measured using ImageJ minus background.
Figure 10:
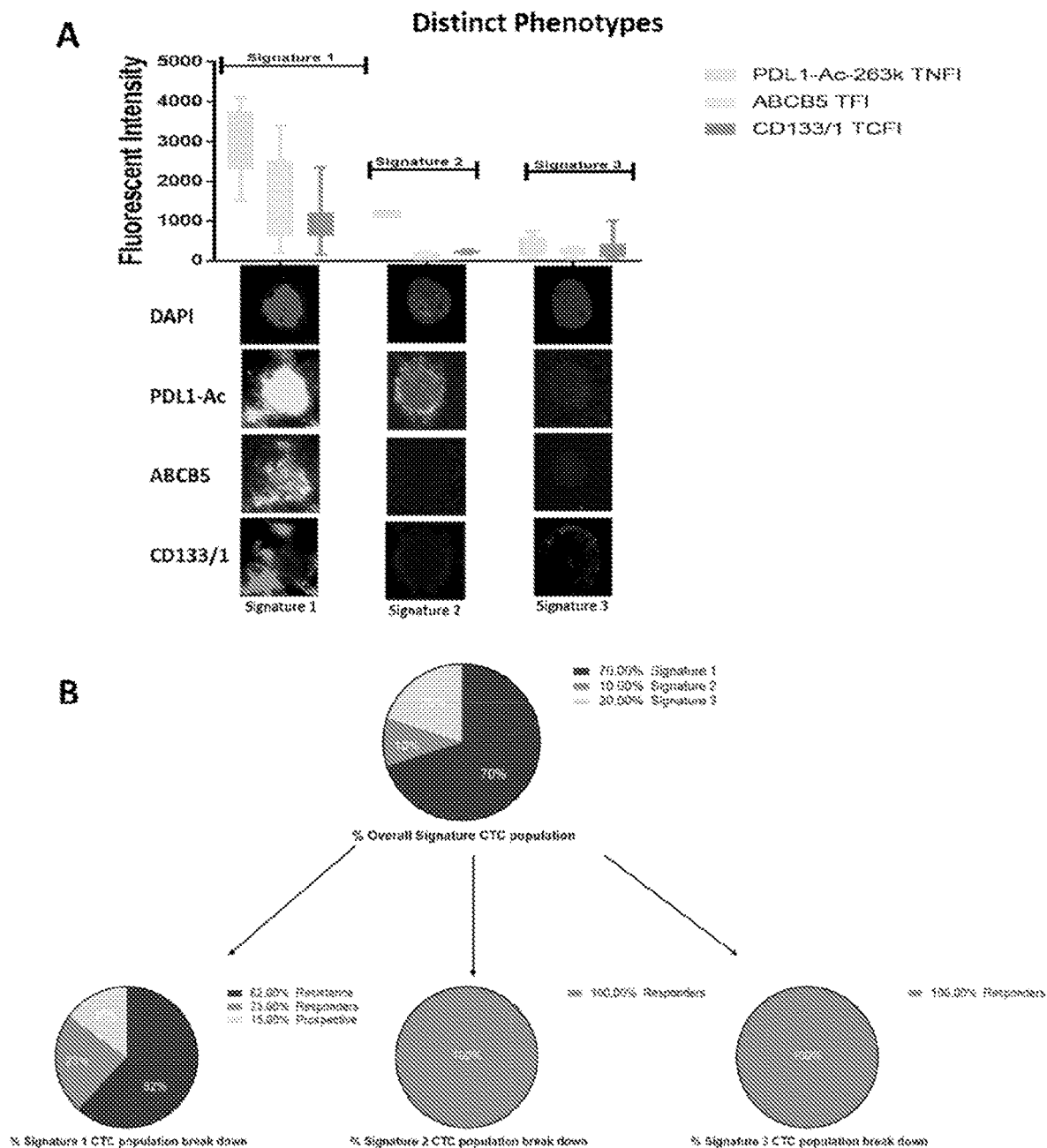
FIG. 10 is a graphical and photographic representation showing that low level expression of PD-L1-263KAc in CTCs correlated with a responsive phenotype but high-level expression of PD-L1-263KAc correlated with a non-responsive or resistant CTC phenotype. (A) CTCs isolated from melanoma bloods from either a resistant cohort or a responder cohort defined as per RECIST 1.1 were screened with a panel antibodies specific for PD-L1 K263-Ac and for mesenchymal/drug resistant biomarkers CD133 and ABCB5. Cells were fixed and immunofluorescence microscopy was performed, probing with primary antibodies to CD133, PD-L1-K263-Ac and ABCB5, and with DAPI. Representative images for each dataset are shown. Graphs represent the TCFI values for CD133, TNFI for PD-L1-K263-Ac and TFI for ABCB5 measured using ImageJ minus background (n=5 patients per a group). Melanoma CTCs derived from liquid biopsies were divided into 3 signatures based on PD-L1-Ac expression. Signature 3 is low expression: under 750, Signature 2 is mid-range expression under 1500 and signature 1 is high expression which is over 1500. (B) Percentage population of total cells counted of each of the 3 signatures found in melanoma CTCs derived from liquid biopsies. The % population for each signature was then further divided into Resistance, Responder and prospective as determined by RECIST 1.1.

The inventors also examined two patients in detail and determined that the DRS signature could also predict responsiveness to drug or resistant, refractory disease (FIG. 9B). Notably, the results also showed that low level expression of PD-L1-K263Ac in CTCs was tied to a responsive phenotype but high-level expression of PD-L1-K263Ac exhibited strong correlation with resistant CTC phenotypes (FIG. 10).

Figure 11:
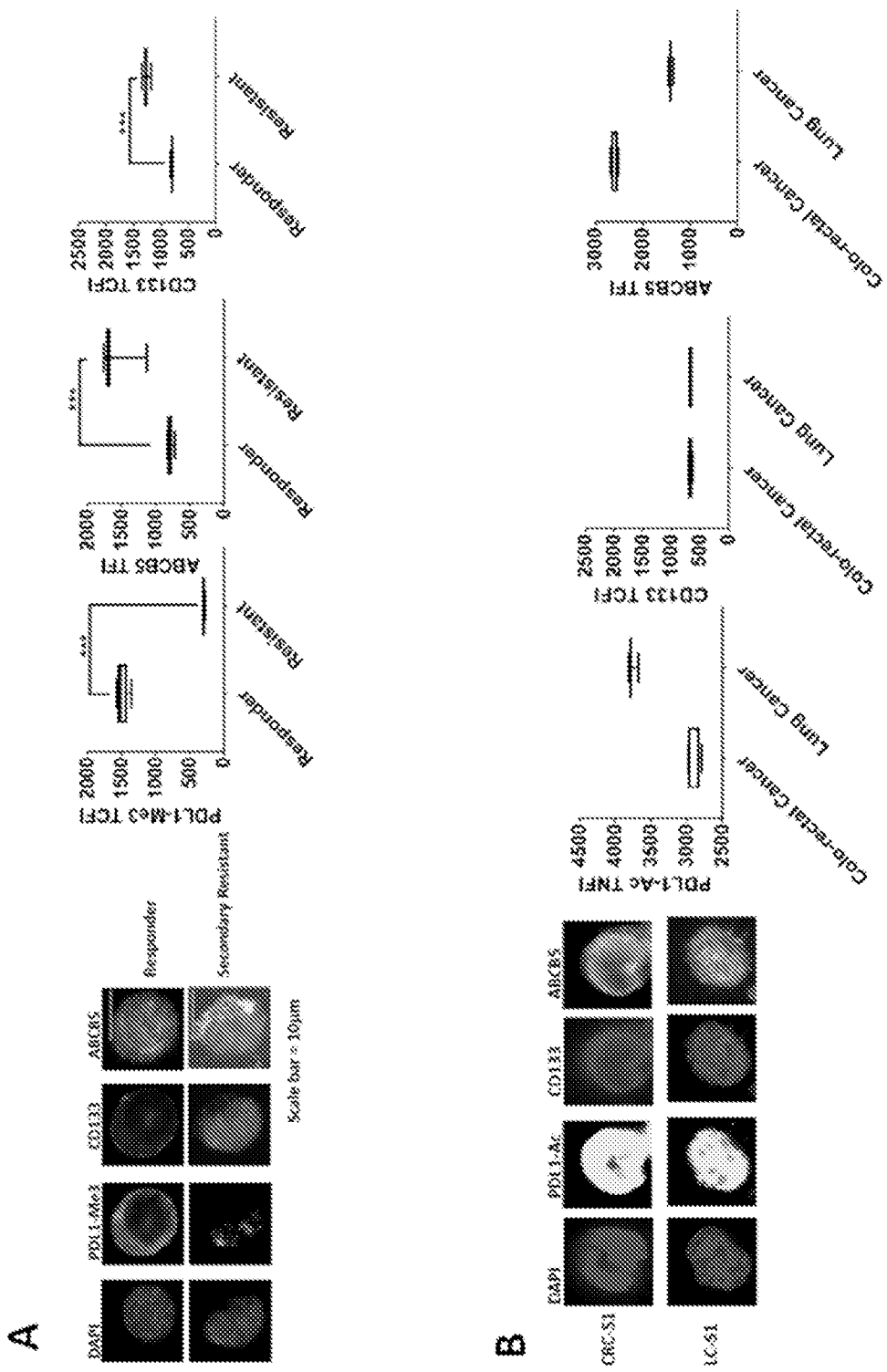
FIG. 11 is a photographic and graphical representation showing that PD-L1 K263-Me is decreased in non-responder or resistant CTC samples in comparison to responder CTC samples. (A) CTCs isolated from melanoma bloods from either responder or resistant cohorts to immunotherapy as per RECIST 1.1 were screened with antibodies specific for PD-L1 K263-Me and for mesenchymal/drug resistant biomarkers CD133 and ABCB5. Cells were fixed and immunofluorescence microscopy was performed, probing with primary antibodies to CD133, PD-L1 K263-Me and ABCB5, and with DAPI. Representative images for each dataset are shown. Graphs represent the TCFI values for CD133, TCFI for PD-L1 K263-Me and TFI for ABCB5 measured using ImageJ minus background (n=5 patients per a group). (B) CTCs isolated from late stage colorectal cancer (CRC) or lung cancer bloods were screened with a panel antibodies specific for PD-L1 K263-Ac and for mesenchymal/drug resistant biomarkers CD133 and ABCB5. Cells were fixed and immunofluorescence microscopy was performed, probing with primary antibodies to CD133, PDL1-263k-me3 and ABCB5, and with DAPI. Representative images for each dataset are shown. Graphs represent the TCFI values for CD133, TCFI for PD-L1 K263-Ac and TFI for ABCB5 measured using ImageJ minus background (n=5 patients per a group).

In addition, it was found that expression of PD-L1-K263Me3 was significantly decreased in resistant CTC samples as compared to responder CTC samples (FIG. 11A).

The DRS signature antibody panel was also used to explore advanced end stage colo-rectal and lung cancer patient CTC samples, and it was found that in both cases there was high expression of PD-L1-K263Ac (FIG. 11B).

Example 5

PD-L1 K263Ac Expression is Increased in Drug-Resistant MBC Cell Lines

Figure 12:
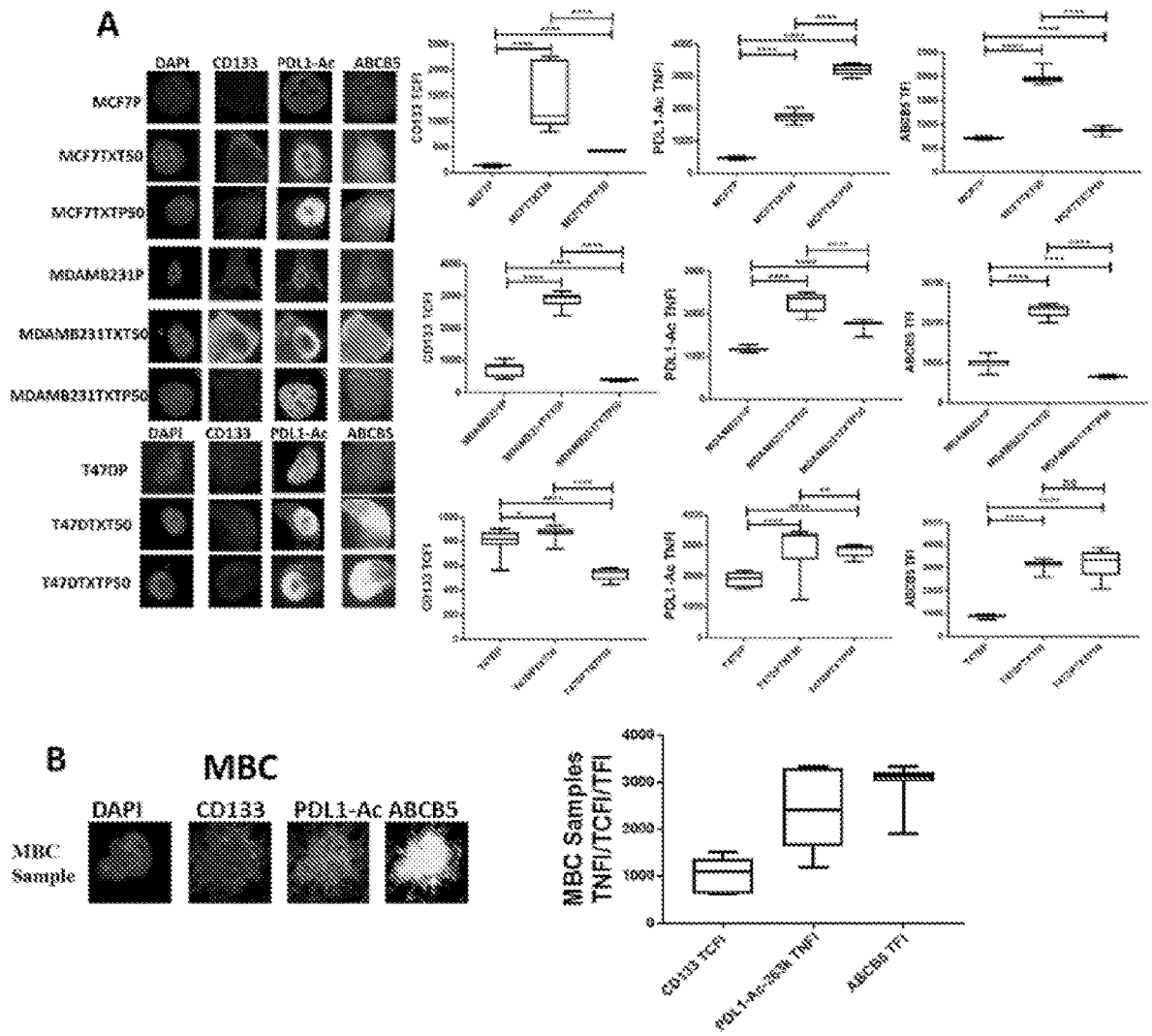
FIG. 12 is a photographic and graphical representation showing PD-L1-K236-Ac is upregulated in drug resistant metastatic breast cancer (MBC) cell lines and MBC patient samples. (A) Drug resistant MBC cell lines were screened with a panel of antibodies specific for PD-L1 K263-Ac and for mesenchymal/drug resistant biomarkers CD133 and ABCB5. Cells were fixed and immunofluorescence microscopy was performed, probing with primary antibodies to CD133, PD-L1 K263-Ac and ABCB5, and with DAPI. Representative images for each dataset are shown. Graphs represent the TCFI values for CD133, TNFI for PD-L1 K263-Ac and TFI for ABCB5 measured using ImageJ minus background (n=20 cells). (B) CTCs isolated from stage IV MBC patients were fixed and immunofluorescence microscopy was performed, probing with primary antibodies to CD133, PD-L1 K263-Ac (T53p) and ABCB5, and with DAPI. Representative images for each dataset are shown. Graphs represent the TCFI values for CD133, TNFI for PD-L1 K263-Ac and TFI for ABCB5 measured using ImageJ minus background.

Three drug-resistant breast cancer cell lines and naïve controls treated with a drug targeting the P-glycoprotein pump mechanism were probed with the DRS signature antibody panel and it was found that PD-L1-K263Ac was upregulated in both the drug-resistant cell lines and the P-glycoprotein pump mechanism treated cells. These results suggest that PD-L1 plays a role in drug-evasion (FIG. 12A). Significant expression of the DRS signature was also found in stage IV MBC patient derived CTCs using the same antibody panel (FIG. 12B).

Example 6

PD-L1 K263Ac Co-Localizes with P300 with Increased Disease Burden

Figure 13:
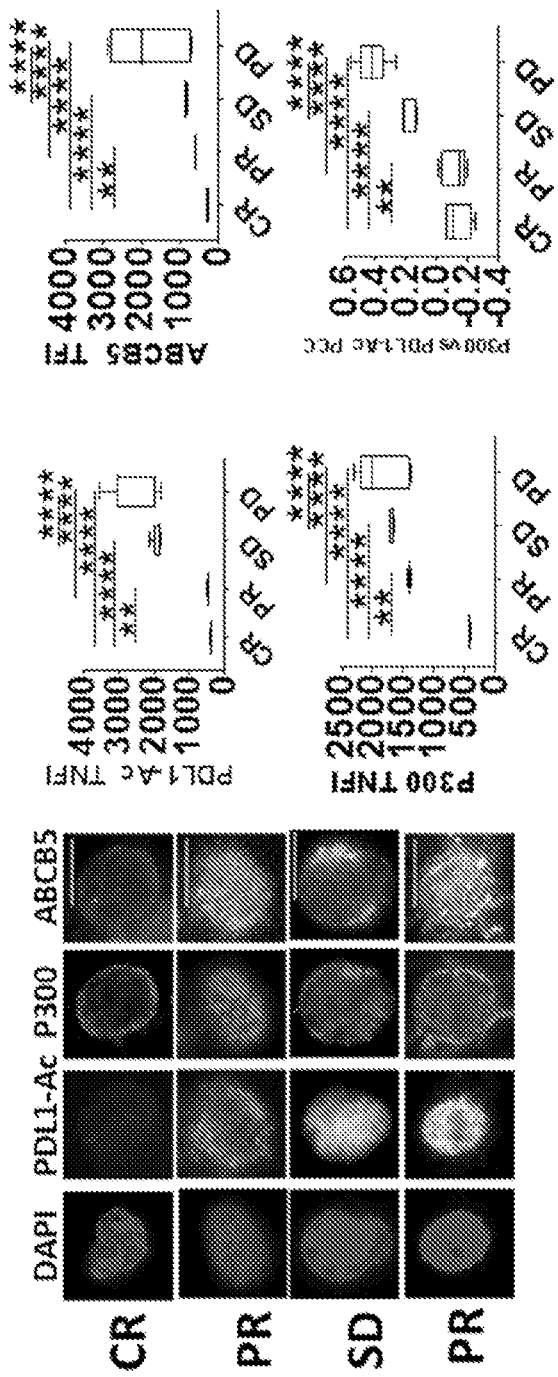
FIG. 13 is a photographic and graphical representation showing that PD-L1-236KAc was upregulated in both chemo-resistant cell lines and in a stage IV MBC patient derived CTCs. (A) CTCs isolated from melanoma bloods from complete response (CR), partial response (PR), stable disease (SD) or progressive disease (PD) as per RECIST 1.1 were screened with a panel of antibodies specific for PD-L1 K263-Ac and for mesenchymal/drug resistant biomarkers P300 and ABCB5. Cells were fixed and immunofluorescence microscopy was performed, probing with primary antibodies to P300, PDL1-263k-Ac and ABCB5, and with DAPI. Representative images for each dataset are shown. Graphs represent the TNFI values for P300, TNFI for PD-L1 K263-Ac and TFI for ABCB5 measured using ImageJ minus background (n=5 patients per a group). The PCC was determined for P300 versus PD-L1 K263-Ac. PCC indicates the strength of relation between the two fluorochrome signals for at least 20 individual cells ±SE.
Figure 14:
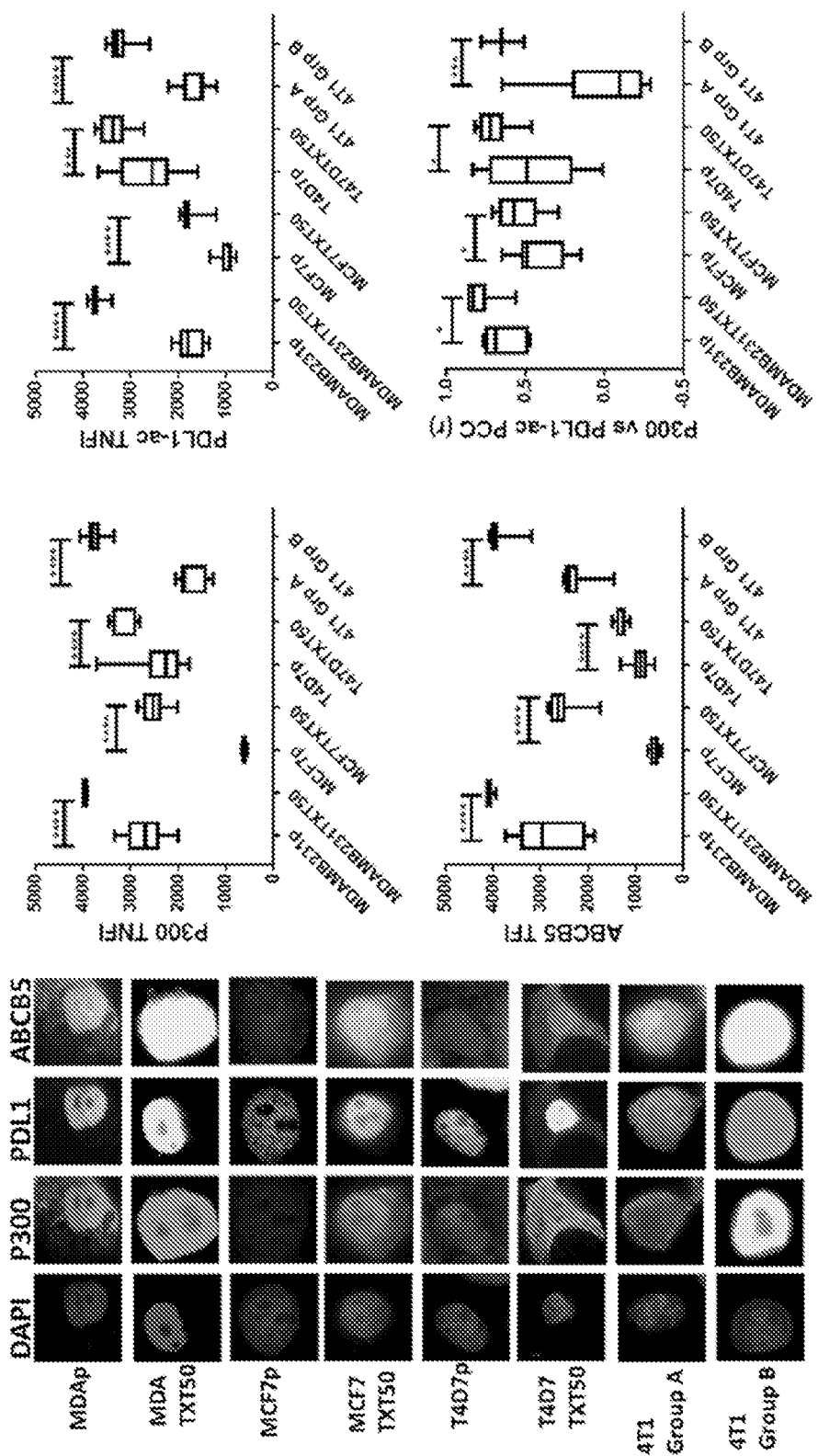
FIG. 14 is a photographic and graphical representation depicting strong co-localization of P300 with PD-L1-236KAc and high expression of both in drug-resistant MBC cell lines. Drug resistant MBC cell lines were fixed and immunofluorescence microscopy was performed, probing with primary antibodies to P300, PD-L1-236KAc and anti-ABCB5, and with DAPI. Representative images for each dataset are shown. Graphs represent the TNFI values for P300, TNFI for PD-L1-236KAc and TFI for ABCB5 measured using ImageJ minus background (n=5 patients per a group). the PCC was determined for P300 versus PD-L1-236KAc. PCC indicates the strength of relation between the two fluorochrome signals for at least 20 individual cells ±SE.
Figure 15:
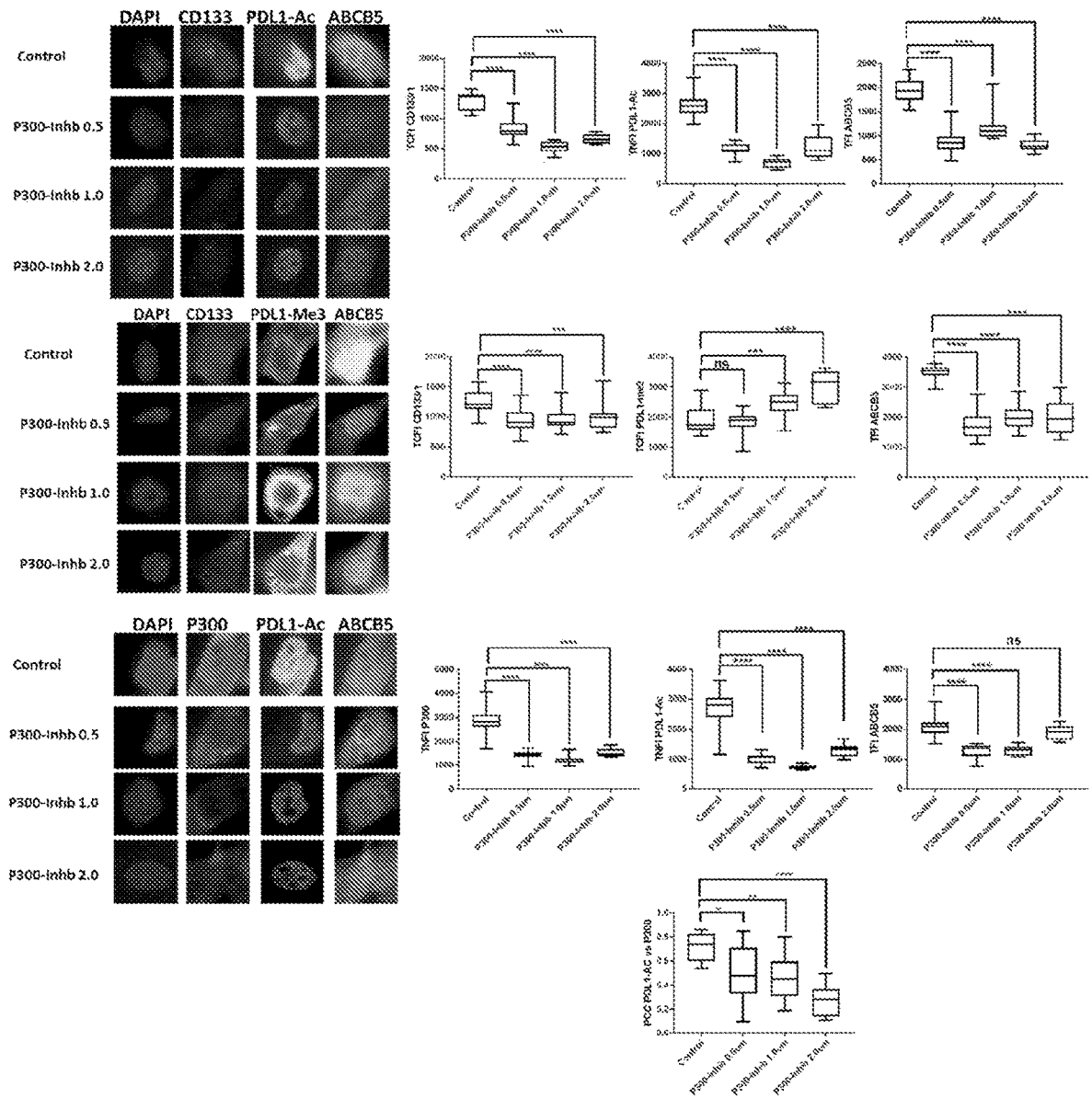
FIG. 15 is a photographic and graphical representation showing that treatment of MDA-MB-231 triple negative MBC cells with a P300 inhibitor reduces PD-L1 K263-Ac and increases PD-L1 K263-Me. MDA-MB-231 triple negative cell line was treated with increasing P300 inhibitor concentration and were screened with an antibody panel for a mesenchymal, resistant signature consisting of P300, PD-L1-K263-Ac and ABCB5. Cells were fixed and immunofluorescence microscopy was performed, probing with primary antibodies to P300, PD-L1-K263-Ac and ABCB5, and with DAPI. Representative images for each dataset are shown. Graphs represent the TNFI values for P300, TNFI for PD-L1 K263-Ac and TFI for ABCB5 measured using ImageJ minus background (n=20 cells). The PCC was determined for P300 versus PD-L1 K263-Ac. PCC indicates the strength of relation between the two fluorochrome signals for at least 20 individual cells ±SE.

Due to the importance of protein acetylation PTMs in control of protein nuclear localization and interaction, the interplay between P300 and PD-L1-K263Ac was also investigated and strong association was found between these proteins in drug resistant samples (FIG. 13). The interaction between P300 and PD-L1-K263Ac was also tested in MBC drug-resistant lines and it was found that P300 strongly co-localized with PD-L1-K263Ac with high expression in the resistant lines (FIG. 14). To further examine the importance of P300, MDA-MB-231 cells treated with a P300 inhibitor were probed with the DRS signature antibody panel, and it was found that as the concentration of the P300 inhibitor increased PD-L1-K263Ac went down and PD-L1-K263Me3 went up (FIG. 15).

Example 7

Nuclear PD-L1 Promotes an Aggressive, Drug-Resistant, Mesenchymal Transcriptome Signature The plasmid constructs described in Example 1 were transfected into an epithelial breast cancer cell line (MCF7)

to examine the nuclear and epigenetic role of PD-L1. This study revealed that the WT-PD-L1 construct displayed both cytoplasmic and nuclear effects, whereas the Mut1-PD-L1 construct demonstrated only nuclear effects. These differences were examined by Nanostring analysis of the transcriptome using a Pan Cancer immune chip that analyzes 700 genes associated with the immune system and cancer, to identify which transcripts are significantly upregulated by the mutant and WT constructs, respectively. Genes significantly upregulated by nuclear PD-L1 expression are shown in FIG. 16.

Figure 17:
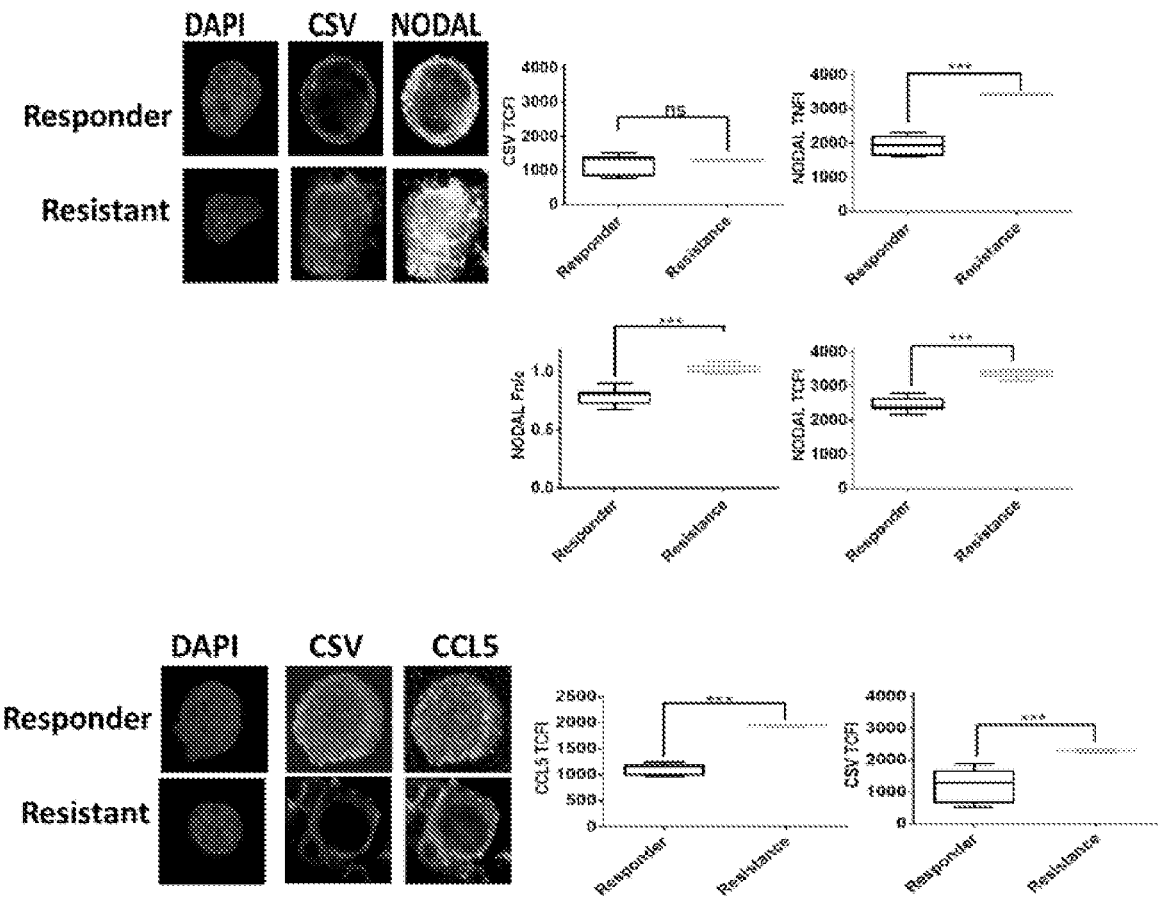
FIG. 17 is a photographic and graphical representation showing that overexpression of PD-L1 leads to upregulation of chemo-resistance, sternness and/or disease progression biomarkers NODAL and CCL5. CTCs isolated from melanoma bloods from either responder or resistant (non-responder) cohorts to immunotherapy as per RECIST 1.1 were screened with a panel for a mesenchymal, resistant signature consisting of CSV, NODAL or CSV and CCL5. Cells were fixed and immunofluorescence microscopy was performed, probing with primary antibodies to CSV, NODAL or CSV and CCL5, and with DAPI. Representative images for each dataset are shown. Graphs represent the TCFI values for CSV, TCFI for CCL5 and TNFI, TCFI for NODAL) or the nuclear/cytoplasmic fluorescence ratio (Fn/c) using the equation: $Fn/c = (Fn-Fb)/(Fc-Fb)$, where Fn is nuclear fluorescence, Fc is cytoplasmic fluorescence, and Fb is background fluorescence. measured using ImageJ minus background.

Next, CTCs isolated from melanoma bloods from either immunotherapy responder or resistant cohorts as per RECIST 1.1 were screened with an antibody panel specific for a mesenchymal, immunotherapy resistant signature consisting of CSV, NODAL or CSV and CCL5. Of note, NODAL and CCL5 were both highly upregulated by overexpression of PD-L1 and the results presented in FIG. 17 show that these proteins were also significantly upregulated in the immunotherapy resistant patient cohort. CSV was included as a maker for CTCs. This indicates a strong correlation between the transcriptome effects of the PD-L1 constructs and the mechanism present in immunotherapy resistant melanoma patient derived CTCs.

Proposed Mechanism for Nuclear PD-L1 Model

Figure 18:
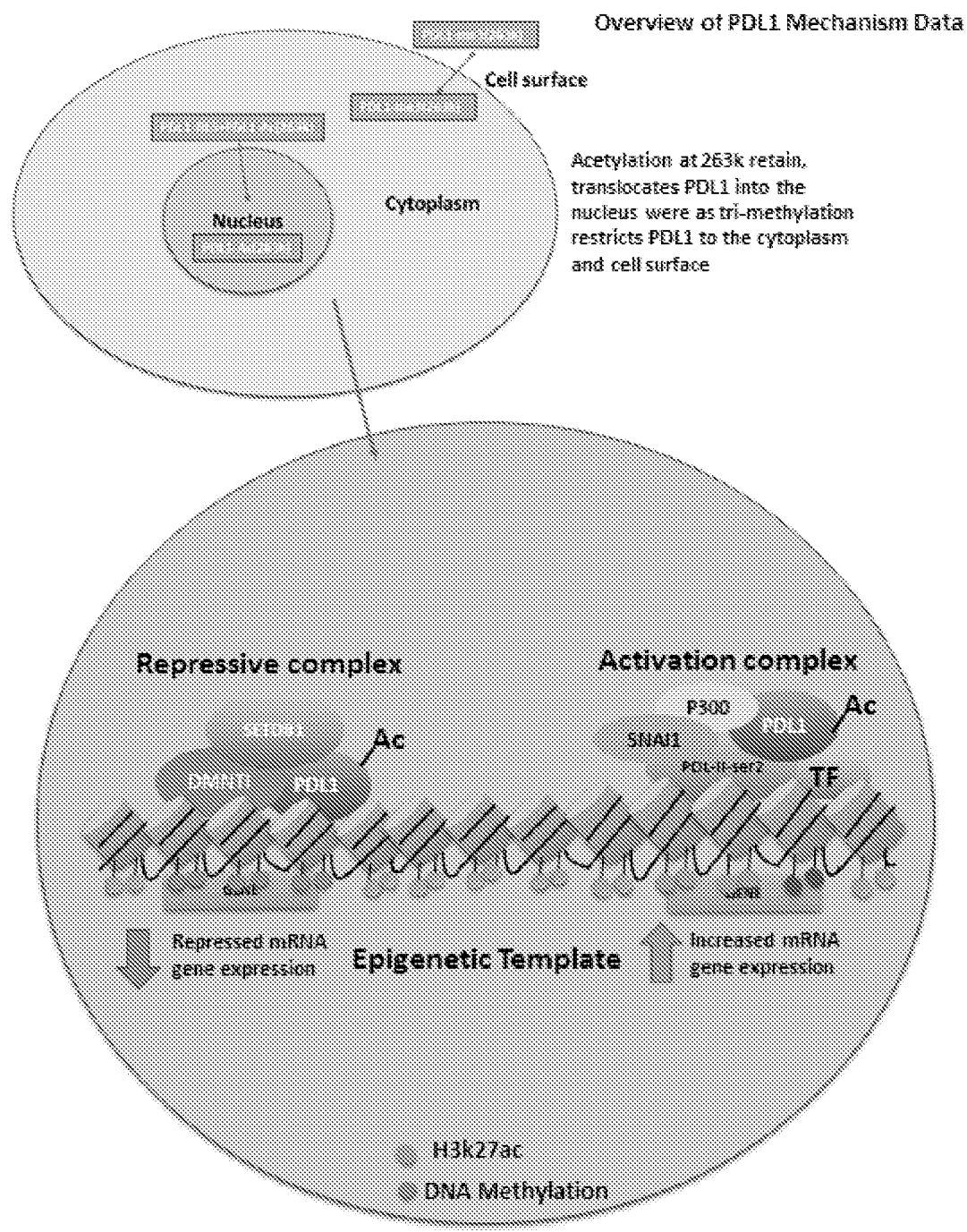
FIG. 18 is a graphical representation showing a proposed mechanism for nuclear PD-L1. In this mechanism, PD-L1-K263-Ac has both a repressive role and activation role in the nucleus, in which PD-L1-K263-Ac forms part of a repressive complex with markers such as DMNT1 and SETDB1. In addition to this, PD-L1-K263-Ac also forms a strong complex with enhancer/activation histone PTMs such as H3k27ac as well as mesenchymal transcription factors like SNAI1 and HAT proteins like P300 which also acetylates PD-L1.

Without wishing to be bound by any particular theory or mode of operation, the present inventors propose that PD-L1 associates with chromatin in the nucleus of a cancer cell and forms both repressive complexes of transcription and complexes which activate transcription. This is backed up by Nanostring analysis discussed in Example 7, which shows upregulation of mesenchymal, stem-like resistance proteins and downregulation of anti-tumor genes (see, FIG. 18).

Example 8

Figure 19:
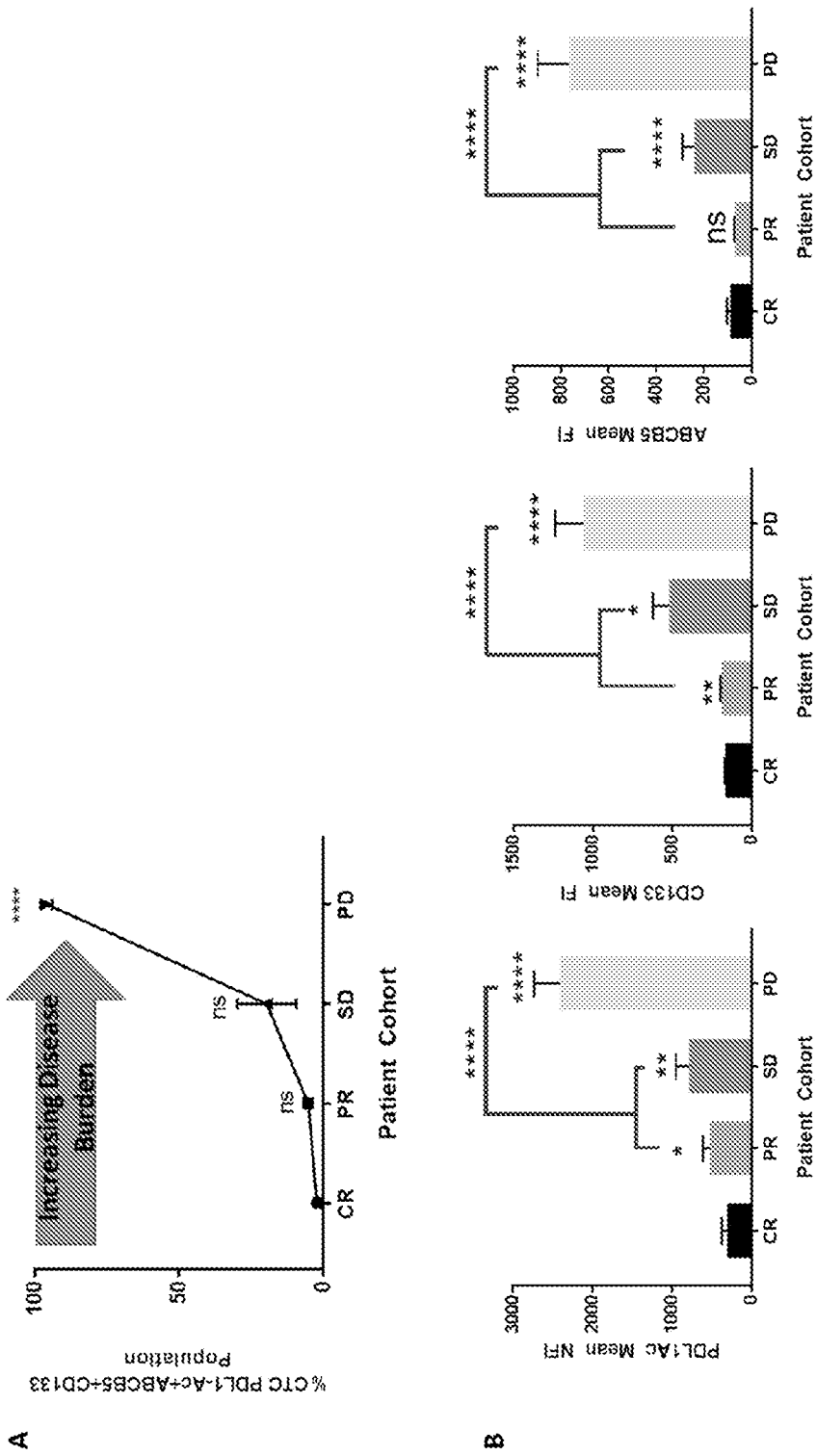
FIG. 19 is a graphical representation showing that the expression of PD-L1-K263Ac, CD133 and ABCB5 increases with increased disease burden. (A) CTCs isolated from melanoma bloods from either complete response (CR), partial response (PR), stable disease (SD) or progressive disease (PD) as per RECIST 1.1 were screened with a panel for a mesenchymal, resistant signature consisting of CSV, PDL1-263k-Ac and ABCB5. Cells were fixed and samples labelled with primary antibodies to anti-CD133, anti-PDL1-263k-Ac and anti-ABCB5 with DAPI. Total % population change of labelled CTCs was quantified using the ASI's mIF system generic scan and analysis system for multiplexed Immuno-fluorescent samples for high through-put IF microscopy to quantify cell number and IF signal intensity. Graph plot represents the total change of PDL1+CTCs with CD133 and ABCB5 markers for mesenchymal, chemoresistance signatures. Graph represents % population (n=40 patient samples per a group). (B) Intensity expression was calculated from the same samples as (A) and Graphs plots represent the mean FI values for CD133, mean NFI for PDL1 and mean FI for ABCB5 (n=40 patient samples per a group) and were measured using ASI's mIF system generic scan and analysis system for multiplexed Immuno-fluorescent samples for high through-put IF microscopy quantify cell number and IF signal intensity.

High Through-Put Microscopy Revealed PD-L1 K263-Ac Positive CTCs are Significantly Increased in Melanoma in Higher Disease Burden Patient Cohorts Using an ASI mIF digital pathology system (Applied Spectral Imaging 5315, Avenida Encinas, Suite 150 Carlsbad, CA 92008, USA), the present inventors tested their key chemo-resistant, stem like-signature with PDL1-Ac in melanoma patient samples. Notably, they found that the expression of these biomarkers increased with increased disease burden (FIG. 19A) and that the PD cohort had the highest expression of PD-L1-K263Ac along with stem-like marker CD133 and chemoresistance stem-like marker ABCB5 (FIG. 19B). The CR cohort was found to have ~2% of all CTCs expressing PD-L1-K263Ac+/CD133+/ABCB5+. This increased to ~5% for PR and 19% for SD, however the increase was not significant. Strikingly the CTC population % in PD patients with the highest disease burden was revealed to increase to ~96%, which was markedly higher than all other cohorts. Therefore, the % population of PD-L1-K263Ac+/CD133+/ABCB5 reveals both an increased and progressive disease and can also show if the patient is responding or resistant to the specific therapy being employed based on overall CTC population numbers.

Materials and Methods

Isolation of Circulating Tumor Cells

Metastatic Melanoma Biopsies were pre-enriched using the RosetteSep™ method to isolate CTCs by employing the RosetteSep™ Human CD45 Depletion Kit (15162, Stemcell Technologies) to remove CD45+ cells and red blood cells, using density gradient centrifugation with SepMate™-15 (IVD) density gradient tubes (85420, Stemcell Technologies) and Lymphoprep™ density gradient medium (07861, Stemcell Technologies). Enriched cells where then cytospun onto a coverslip pre-treated with poly-1-lysine and fixed then stored in PBS for staining.

Immunofluorescent Microscopy

Cells for microscopy were permeabilized by incubation with 1% Triton X-100 for 20 min. Cells were probed with a variety of antibodies including:

Rabbit or Goat anti-PDL1, mouse-anti H3K27ac, H3k4me3 or H3k9me3. Mouse anti-CSV, rabbit anti-EGFR, goat anti-SNAIL. Rabbit-EHTM2, mouse anti-DMNT1, goat anti-SETDB1. Our custom-rabbit host PDL1-263k-Ac, PDL1-263k-me3 or PDL1-263k. Mouse anti-5-mC, mouse anti-CD133, goat-anti-ABCB5 or mouse anti-P300. As well as macrophage markers goat anti-F4/80 or mouse anti-CD38 or CD206. Markers for aggressive, metastatic signatures also included goat anti-Nodal and goat anti-CCL5. Primary antibodies were visualized with a donkey anti-rabbit secondary antibody conjugated to Alexa Fluor 488, anti-mouse secondary 568 or anti-goat secondary 647. Cover slips were mounted on glass microscope slides with ProLong Diamond Antifade reagent (Life Technologies). Protein targets were localized by confocal laser scanning microscopy. Single 0.5 μm sections were obtained using a Leica DMI8 microscope using 100× oil immersion lens running LAX software. The final image was obtained by averaging four sequential images of the same section. Digital images were analyzed using ImageJ software (ImageJ, NIH, Bethesda, MD, USA) to determine either the Total Nuclear Fluorescent Intensity (TNFI), the Total Cytoplasmic Fluorescent Intensity (TCFI). The Mann-Whitney nonparametric test (GraphPad Prism, GraphPad Software, San Diego, CA) was used to determine significant differences between datasets.

Co-Localization

ImageJ software with automatic thresholding and manual selection of regions of interest (ROIs) specific for cell nuclei was used to calculate the Pearson's co-efficient correlation (PCC) for each pair of antibodies. PCC values range from: −1=inverse of co-localization, 0=no co-localization, +1=perfect co-localization. Total nuclear florescence intensity was also measured in a minimum of n=20 cells for each sample set. Nuclear intensity was analysed using ImageJ software, with the nucleus of each cell and total nuclear fluorescence computed by the software minus background. The Mann-Whitney nonparametric test (GraphPad Prism, GraphPad Software, San Diego, CA) was used to determine significant differences between datasets.

Cell Culture

All breast cancer cell lines used were sourced from ATCC, except the docetaxel resistant lines which were kind gift of Dr Sikic (Standford University). Cell lines were maintained and cultured in DMEM (Invitrogen) supplemented with 10% FBS, 2 mM L-glutamine, and 1% PSN. MCF-7 cells were stimulated with 1.29 ng/ml phorbol 12-myristate 13-acetate (PMA) (Sigma-Aldrich) or 5 ng/ml recombinant TGF-β1 (R&D Systems) for 60 hours 38.

Generation of PD-L1-WT, PD-L1-K263Ac and PD-L1-K263Me3 Antibodies

Antibodies were generated against peptides 2803201, 2803204 and 2803213 (Table 1). As short peptides are generally not immunogenic in their own right, it is often necessary to couple them to immunogenic carrier proteins. To facilitate this coupling, a cysteine was incorporated at the C-terminus of the peptide and reacted to conjugate the peptide to an immunogenic carrier protein, Keyhole Limpet Hemocyanin (KLH). No special immunization protocols were required to generate anti-trimethylated or anti-acetylated peptide antibodies. Two rabbits for each peptide sequence were immunized several weeks apart. The first immunization is with an emulsion of the peptide conjugate with Complete Freund's adjuvant, the second using Incomplete Freund's adjuvant. Potent anti-peptide sera are obtained after several weeks (refer to Palfreyman, et al. (1984) *J Immunol Meth*, 75:383).

TABLE 1

Peptide sequences used for antibody generation

| Peptide | Sequence | Molecular Weight (Da) |
|---|---|---|
| 2803201 | FRLRKGRMMDVKKC-OH [SEQ ID NO: 2] | 1768.25 |
| 2803204 | FRLRK(Ac)GRMMDVKKC-OH [SEQ ID NO: 3] | 1810.29 |
| 2803213 | FRLRK(Me$_3$)GRMMDVKKC-OH [SEQ ID NO: 4] | 1811.34 |

The testing of trimethylated and acetylated peptide antisera is performed using an enzyme linked immunosorbent assay (ELISA) where the sera are titrated on microtiter plates coated with non-trimethylated peptide and trimethylated peptide, or non-acetylated and acetylated peptide.

Antibody enhancement is performed by coupling the non-trimethylated, non-acetylated analogue of the peptide used for the immunization to a gel Sulfo Link Coupling Resin (Thermo Scientific, Catalogue number 20401) using the available cysteine residue, following the manufacturer's instructions. The resultant gel is incubated with aliquots of the antisera to absorb antibodies specific to the non-trimethylated, non-acetylated peptide. The resultant antiserum will have an enhanced specificity for the trimethylated peptide or acetylated peptide sequence.

To produce affinity purified antibodies that are specific to the trimethylated or acetylated peptide only, it is necessary to first perform the enhancement procedure to remove antibodies from the serum that are specific to the non-tri methylated and non-acetylated peptide. Specificity of the affinity purified antibodies are tested by ELISA back onto both the non-trimethylated and the trimethylated peptides, or non-acetylated and acetylated peptides coated onto the plate. Generated antibodies showed high specificity for trimethylated PD-L1 and acetylated PD-L1 at residue 263.

4T1 Mouse Model

A total of $2\times10^5$ cells were injected per mouse into mammary gland in 50 μL of PBS. Treatments were started on mice after 15 days post-inoculation of 4T1 cells. Treatment groups are as follows: A—Control, B—30 mg/kg Abraxane. Tumors were measured using calipers and the tumor volumes (mm$^3$) were calculated using the formula (length×width$^2$). Tumors were measured using external calipers and calculated using the modified ellipsoidal formula: ½ (a/b2), where a=longest diameter and b=shortest diameter. Tumors were allowed to grow to around 50 mm$^3$ before commencing treatments (around 15 days). All treatments were given by IP injections of Abraxane (30 mg/kg). Tumors were excised and collected in DMEM supplemented with 2.5% FCS. Tumors were then finely minced using a surgical blade and incubated at 37° C. for 1 hour in DMEM 2.5% FCS and collagenase type 4 (Worthington-Biochem) (1 mg of collagenase/1 g of tumor). Digested tumors were spun and resuspended in DMEM 2.5% FCS before being passed through a 0.2 μM filter and used for fluorescence microscopy.

ASI System Method (High Through Put, High Resolution Microscopy)

ASI's mIF system is a generic scan and analysis system for multiplexed immunofluorescent samples. It was designed to scan a slide stained with DAPI and up to 6 antibody stains, remove auto fluorescent, resolve unmixing between filters and perform cell-based analysis on the acquired data. Touching cells are automatically segmented, signal expression is quantitatively measured and results per cell and over entire scanned region are displayed. Various automated and semi-automated scanning modes are supported including:

1. Efficient Density-based scan for suspension samples—scanning the sample based on cell population for fastest cell scoring;
2. Scanning selective regions/areas; and
3. Interactive scanning of specific locations of interest.

In all modes, integrated statistics for thousands and tens of thousands of cells with co-localization of antibodies can be derived in minutes. 3D stacking, auto exposure, auto focus and other imaging parameters are inherent part of each scan. The images was used to determine the either the mean Nuclear Fluorescent Intensity (NFI) or overall Fluorescent Intensity (FI). Total number of cells were counted in a defined area using an automated stage and ASI software used to automatically select cells and measure fluorescent intensities. Resulting data was then employed to calculate CTC population dynamics expressed as a % of total cell population The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

What is claimed is:

1. A method for determining increased likelihood of resistance of a cancer cell to a cytotoxic therapy or immunotherapy, wherein the increased likelihood of resistance is relative to a response to the therapy of a control cancer cell, and wherein the immunotherapy is a PD-1 directed immunotherapy or a PD-L1 directed immunotherapy, the method comprising detecting the presence of PD-L1-K263Ac in the cancer cell, to thereby determine that the cancer cell has increased likelihood of resistance to the therapy.

2. The method of claim 1, comprising detecting an elevated level of PD-L1-K263 Ac in the cancer cell relative to a suitable control, which indicates that the cancer cell has increased likelihood of resistance to the therapy.

3. The method of claim 1, comprising contacting a sample comprising the cancer cell with an antigen-binding molecule that binds specifically to PD-L1-K263Ac, and detecting in the sample a complex that comprises the antigen-binding molecule and PD-L1-K263Ac, to thereby determine that the cancer cell has increased likelihood of resistance to the therapy.

4. A method for determining increased likelihood of sensitivity of a cancer cell to a cytotoxic therapy or immunotherapy, wherein the increased likelihood of sensitivity is relative to a response to the therapy of a control cancer cell, and wherein the immunotherapy is a PD-1 directed immunotherapy or a PD-L1 directed immunotherapy, the method comprising detecting the presence of PD-L1-K263Me in the cancer cell, to thereby determine that the cancer cell has increased likelihood of sensitivity to the therapy.

5. The method of claim 4, comprising detecting an elevated level of PD-L1-K263Me in the cancer cell relative to a suitable control, which indicates that the cancer cell has increased likelihood of sensitivity to the therapy.

6. The method of claim 4, comprising contacting a sample comprising the cancer cell with an antigen-binding molecule that binds specifically to PD-L1-K263Me, and detecting in the sample a complex that comprises the antigen-binding molecule and the PD-L1-K263Me, to thereby determine that the cancer cell has increased likelihood of sensitivity to the therapy.

7. A method for predicting a likelihood of response of a cancer cell to a cytotoxic therapy or immunotherapy, wherein the likelihood of response to the therapy is relative to a response to the therapy of a control cancer cell, and wherein the immunotherapy is a PD-1 directed immunotherapy or a PD-L1 directed immunotherapy, the method comprising: measuring the level of PD-L1-K263Ac in the cancer cell, measuring the level of PD-L1-K263Me in the cancer cell; comparing the level of PD-L1-K263Ac and PD-L1-K263Me in the cancer cell; and predicting the response of the cancer cell to the therapy based on a comparison of the level of PD-L1-K263 Ac and the level of PD-L1-K263Me, wherein a higher level of PD-L1-K263Ac than PD-L1-K263Me in the cancer cell indicates that the cancer cell has increased likelihood of resistance to the therapy and wherein a higher level of PD-L1-K263Me than PD-L1-K263Ac in the cancer cell indicates that the cancer cell has increased likelihood of sensitivity to the therapy.

8. The method of claim 7, comprising: contacting a sample comprising the cancer cell with a first antigen-binding molecule that binds specifically to PD-L1-K263Ac and a second antigen-binding molecule that binds specifically to PD-L1-K263Me; measuring in the sample the level of a first complex that comprises the first antigen-binding molecule and the PD-L1-K263Ac, and the level of a second complex that comprises the second antigen-binding molecule and the PD-L1-K263Me; and predicting likelihood of response of the cancer cell to the therapy based on a comparison of the level of the first complex and the level of the second complex, wherein a higher level of the first complex than the second complex in the sample indicates that the cancer cell has increased likelihood of resistance to the therapy and wherein a higher level of the second complex than the first complex in the sample indicates that the cancer cell has increased likelihood of sensitivity to the therapy.

9. A method for stratifying a cancer patient as a likely responder or non-responder to a cytotoxic therapy or immunotherapy, wherein the immunotherapy is a PD-1 directed immunotherapy or a PD-L1 directed immunotherapy, the method comprising detecting in a sample taken from the patient a cancer cell that comprises a post-translational modification in the nuclear localization sequence of PD-L1, wherein the post-translational modification is PD-L1-K263Ac or PD-L1-K263Me, wherein if PD-L1-K263Ac is detected in the cancer cell, the patient is stratified as a likely non-responder to the therapy, and wherein if PD-L1-K263Me is detected in the cancer cell, the patient is stratified as a likely responder to the therapy.

10. The method of claim 9, comprising contacting the sample with an antigen-binding molecule that binds specifically to PD-L1-K263Ac, and detecting in the sample a complex that comprises the antigen-binding molecule and the PD-L1-K263 Ac, to thereby stratify the patient as a likely non-responder to the therapy.

11. The method of claim 9, comprising contacting the sample with an antigen-binding molecule that binds specifically to PD-L1-K263Me, and detecting in the sample a complex that comprises the antigen-binding molecule and the PD-L1-K263Me, to thereby stratify the patient as a likely responder to the therapy.

12. A method for stratifying a cancer patient as a likely responder or non-responder to a cytotoxic therapy or immunotherapy, wherein the immunotherapy is a PD-1 directed immunotherapy or a PD-L1 directed immunotherapy, the method comprising: contacting a sample comprising a cancer cell taken from the patient with a first antigen-binding molecule that binds specifically to PD-L1-K263Ac and a second antigen-binding molecule that binds specifically to PD-L1-K263Me; measuring in the sample the level of a first complex that comprises the first antigen-binding molecule and PD-L1-K263Ac, and the level of a second complex that comprises the second antigen-binding molecule and PD-L1-K263Me; and stratifying the patient as a likely responder or non-responder based on a comparison of the level of the first complex and the level of the second complex, wherein the patient is stratified as a likely non-responder if the level of the first complex is higher than the second complex in the sample and wherein the patient is stratified as a likely responder if the level of the second complex is higher than the first complex in the sample.

13. A method for managing treatment of a cancer patient with a cytotoxic therapy or immunotherapy, wherein the immunotherapy is a PD-1 directed immunotherapy or a PD-L1 directed immunotherapy, the method comprising selecting a cancer patient for treatment with the therapy on the basis that the patient is a likely responder to the therapy, or selecting a cancer patient for not treating with the therapy on the basis that the patient is a likely non-responder to the therapy and treating or not treating the patient with the therapy based on the selection, wherein the selection is based on a stratification method that comprises detecting in a sample taken from the patient a cancer cell that comprises a post-translational modification in the nuclear localization sequence of PD-L1, to thereby stratify the patient as a likely responder or non-responder to the therapy, wherein if PD-L1-K263Me is detected in the cancer cell, the patient is stratified as a likely responder to the therapy, and wherein if PD-L1-K263 Ac is detected in the cancer cell, the patient is stratified as a likely non-responder to the therapy.

14. The method of claim 13, comprising contacting the sample with an antigen-binding molecule that binds specifically to PD-L1-K263Me, and detecting in the sample a complex that comprises the antigen-binding molecule and the PD-L1-K263Me, to thereby stratify the patient as a likely responder to the therapy.

15. The method of claim 13, comprising contacting the sample with an antigen-binding molecule that binds specifically to PD-L1-K263Ac, and detecting in the sample a complex that comprises the antigen-binding molecule and the PD-L1-K263Ac, to thereby stratify the patient as a likely non-responder to the therapy.

16. A method for managing treatment of a cancer patient with a cytotoxic therapy or immunotherapy, wherein the immunotherapy is a PD-1 directed immunotherapy or a PD-L1 directed immunotherapy, the method comprising selecting a cancer patient for treatment with the therapy on the basis that the patient is a likely responder to the therapy, or selecting a cancer patient for not treating with the therapy on the basis that the patient is a likely non-responder to the therapy and treating or not treating the patient with the therapy based on the selection, wherein the selection is based on a stratification method that comprises: contacting the sample with a first antigen-binding molecule that binds specifically to PD-L1-K263Ac and a second antigen-binding molecule that binds specifically to PD-L1-K263Me; measuring in the sample the level of a first complex that comprises the first antigen-binding molecule and PD-L1-K263Ac, and the level of a second complex that comprises the second antigen-binding molecule and PD-L1-K263Me; and stratifying the patient as a likely responder or non-responder based on a comparison of the level of the first complex and the level of the second complex, wherein the patient is stratified as a likely non-responder if the level of the first complex is higher than the second complex in the sample and wherein the patient is stratified as a likely responder if the level of the second complex is higher than the first complex in the sample.

* * * * *